(12) United States Patent
Mollard et al.

(10) Patent No.: US 11,938,101 B2
(45) Date of Patent: *Mar. 26, 2024

(54) POLYMORPHIC FORMS OF (R)-2-HYDROXY-2-METHYL-4-(2,4,5-TRIMETHYL-3,6-DIOXOCYCLOHEXA-1,4-DIENYL) BUTANAMIDE

(71) Applicant: PTC Therapeutics, Inc., South Plainfield, NJ (US)

(72) Inventors: Paul Mollard, Mountain View, CA (US); Peter Giannousis, Mountain View, CA (US); Shazad Suchit, Devens, MA (US); Mahmoud Mirmehrabi, Halifax (CA); Christopher R. Cornell, Mountain View, CA (US); Kieron E. Wesson, Mountain View, CA (US)

(73) Assignee: PTC THERAPEUTICS, INC., South Plainfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/692,133

(22) Filed: Mar. 10, 2022

(65) Prior Publication Data

US 2022/0265578 A1 Aug. 25, 2022

Related U.S. Application Data

(63) Continuation of application No. 16/919,044, filed on Jul. 1, 2020, now Pat. No. 11,304,914, which is a continuation of application No. 16/354,070, filed on Mar. 14, 2019, now Pat. No. 10,751,302, which is a continuation of application No. 15/536,603, filed as application No. PCT/US2015/066211 on Dec. 16, 2015, now Pat. No. 10,251,847.

(60) Provisional application No. 62/133,276, filed on Mar. 13, 2015, provisional application No. 62/092,743, filed on Dec. 16, 2014.

(51) Int. Cl.

| | | |
|---|---|---|
| *C07C 235/78* | (2006.01) | |
| *A61K 31/122* | (2006.01) | |
| *A61K 31/164* | (2006.01) | |
| *C07B 57/00* | (2006.01) | |
| *C07C 215/08* | (2006.01) | |
| *C07C 215/28* | (2006.01) | |
| *C07C 215/30* | (2006.01) | |
| *C07C 231/12* | (2006.01) | |
| *C07D 215/28* | (2006.01) | |

(52) U.S. Cl.
CPC .......... *A61K 31/122* (2013.01); *A61K 31/164* (2013.01); *C07B 57/00* (2013.01); *C07C 215/08* (2013.01); *C07C 215/28* (2013.01); *C07C 215/30* (2013.01); *C07C 231/12* (2013.01); *C07C 235/78* (2013.01); *C07B 2200/13* (2013.01); *C07C 2601/16* (2017.05)

(58) Field of Classification Search
CPC ... C07C 215/08; C07C 215/28; C07C 215/30; C07C 231/12; C07C 235/78
See application file for complete search history.

(56) References Cited

U.S. PATENT DOCUMENTS

| | | |
|---|---|---|
| 4,018,799 A | 4/1977 | William et al. |
| 4,026,907 A | 5/1977 | Scott et al. |
| 4,388,312 A | 6/1983 | Terao et al. |
| 5,272,180 A | 12/1993 | Hashimoto et al. |
| 5,348,973 A | 9/1994 | Muppala et al. |
| 5,801,159 A | 9/1998 | Miller et al. |
| 5,821,247 A | 10/1998 | Isobe et al. |
| 5,874,461 A | 2/1999 | De Chaffoy de Courcelles et al. |
| 6,011,046 A | 1/2000 | Ohkawa et al. |
| 6,083,982 A | 7/2000 | Wechter et al. |
| 6,150,402 A | 11/2000 | Wechter et al. |
| 6,232,060 B1 | 5/2001 | Miller et al. |
| 6,271,266 B1 | 8/2001 | Miyamoto et al. |
| 6,426,362 B1 | 7/2002 | Miller et al. |
| 6,528,042 B1 | 3/2003 | Brown et al. |
| 6,608,196 B2 | 8/2003 | Wang et al. |
| 6,653,312 B1 | 11/2003 | Auvin et al. |
| 6,653,346 B1 | 11/2003 | Wang et al. |

(Continued)

FOREIGN PATENT DOCUMENTS

| | | |
|---|---|---|
| EP | 0 831 092 A2 | 3/1998 |
| EP | 0 831 092 A3 | 3/1998 |

(Continued)

OTHER PUBLICATIONS

American Academy of Neurology (2008). "Kids with Autism may have Gene that Causes Muscle Weakness," study conducted by John Shoffner, MD, owner of Medical Neurogenetics, LLC in Atlanta, GA and member of the American Academy of Neurology, to be presented at the American Academy of Neurology 60th Anniversary Annual Meeting in Chicago on Apr. 12-19, 2008, press release on Apr. 13, 2008 located at <http://www.aan.com/PressRoom/Home/PressRelease/588>, last visited on Jul. 22, 2013; 2 pages.

(Continued)

*Primary Examiner* — Rebecca L Anderson
(74) *Attorney, Agent, or Firm* — Squire Patton Boggs (US) LLP

(57) ABSTRACT

Disclosed herein are polymorphic and amorphous forms of anhydrate, hydrate, and solvates of (R)-2-hydroxy-2-methyl-4-(2,4,5-trimethyl-3,6-dioxocyclohexa-1,4-dienyl) butanamide and methods of using such compositions for treating or suppressing oxidative stress disorders, including mitochondrial disorders, impaired energy processing disorders, neurodegenerative diseases and diseases of aging. Further disclosed are methods of making such polymorphic and amorphous forms.

13 Claims, 45 Drawing Sheets

(56) References Cited

U.S. PATENT DOCUMENTS

| | | | |
|---|---|---|---|
| 7,034,054 B2 | 4/2006 | Miller et al. | |
| 7,078,541 B2 | 7/2006 | Boddupalli et al. | |
| 7,119,117 B2 | 10/2006 | Beinlich et al. | |
| 7,179,928 B2 | 2/2007 | Smith et al. | |
| 7,393,662 B2 | 7/2008 | Heavner et al. | |
| 7,432,305 B2 | 10/2008 | Miller et al. | |
| 7,470,798 B2 | 12/2008 | Wang et al. | |
| 7,473,779 B2 | 1/2009 | Auvin et al. | |
| 7,491,312 B2 | 2/2009 | Gilat et al. | |
| 7,514,461 B2 | 4/2009 | Wang et al. | |
| 7,576,241 B2 | 8/2009 | Auvin et al. | |
| 7,718,176 B2 | 5/2010 | Heavner et al. | |
| 7,875,607 B2 | 1/2011 | Wang et al. | |
| 8,044,097 B2 | 10/2011 | Wang et al. | |
| 8,106,223 B2 | 1/2012 | Wesson et al. | |
| 8,314,153 B2 | 11/2012 | Miller et al. | |
| 8,519,001 B2 | 8/2013 | Jankowski et al. | |
| 8,575,369 B2 | 11/2013 | Wesson et al. | |
| 8,653,144 B2 | 2/2014 | Miller et al. | |
| 8,716,486 B2 | 5/2014 | Hinman et al. | |
| 8,716,527 B2 | 5/2014 | Hinman et al. | |
| 8,791,155 B2 | 7/2014 | Wang et al. | |
| 8,952,071 B2 | 2/2015 | Hinman et al. | |
| 8,969,420 B2 | 3/2015 | Miller et al. | |
| 9,162,957 B2 | 10/2015 | Mollard | |
| 9,169,196 B2 | 10/2015 | Jankowski et al. | |
| 9,278,085 B2 | 3/2016 | Miller et al. | |
| 9,370,496 B2 | 6/2016 | Miller | |
| 9,447,006 B2 | 9/2016 | Miller et al. | |
| 9,486,435 B2 | 11/2016 | Hinman et al. | |
| 10,251,847 B2 | 4/2019 | Mollard et al. | |
| 10,751,302 B2 * | 8/2020 | Mollard | A61P 7/06 |
| 11,304,914 B2 * | 4/2022 | Mollard | A61P 3/00 |
| 2002/0132845 A1 | 9/2002 | Miller et al. | |
| 2002/0143049 A1 | 10/2002 | Miller et al. | |
| 2003/0022818 A1 | 1/2003 | Miller et al. | |
| 2003/0144219 A1 | 7/2003 | Phinney et al. | |
| 2004/0105817 A1 | 6/2004 | Gilat et al. | |
| 2005/0065099 A1 | 3/2005 | Walkinshaw et al. | |
| 2005/0065149 A1 | 3/2005 | Wang et al. | |
| 2005/0065150 A1 | 3/2005 | Wang et al. | |
| 2005/0067303 A1 | 3/2005 | Wong et al. | |
| 2006/0051844 A1 | 3/2006 | Heavner et al. | |
| 2006/0258598 A1 | 11/2006 | Herzner et al. | |
| 2006/0281809 A1 | 12/2006 | Miller et al. | |
| 2007/0072943 A1 | 3/2007 | Miller et al. | |
| 2007/0225261 A1 | 9/2007 | Miller et al. | |
| 2007/0281991 A1 | 12/2007 | Adrian et al. | |
| 2009/0118257 A1 | 5/2009 | Jankowski et al. | |
| 2009/0162890 A1 | 6/2009 | Gilat et al. | |
| 2009/0163529 A1 | 6/2009 | Gilat et al. | |
| 2009/0291092 A1 | 11/2009 | Miller et al. | |
| 2010/0010100 A1 | 1/2010 | Hinman et al. | |
| 2010/0029706 A1 | 2/2010 | Miller et al. | |
| 2010/0029784 A1 | 2/2010 | Hinman et al. | |
| 2010/0056429 A1 | 3/2010 | Miller et al. | |
| 2010/0063161 A1 | 3/2010 | Miller et al. | |
| 2010/0063305 A1 | 3/2010 | Iida et al. | |
| 2010/0105930 A1 | 4/2010 | Wesson et al. | |
| 2010/0222436 A1 | 9/2010 | Miller et al. | |
| 2010/0249032 A1 | 9/2010 | Heavner et al. | |
| 2010/0266591 A1 | 10/2010 | Bugelski et al. | |
| 2010/0273892 A1 | 10/2010 | Miller et al. | |
| 2010/0273894 A1 | 10/2010 | Miller | |
| 2011/0046156 A1 | 2/2011 | Miller | |
| 2011/0046219 A1 | 2/2011 | Hinman et al. | |
| 2011/0124679 A1 | 5/2011 | Hinman et al. | |
| 2011/0142834 A1 | 6/2011 | Miller | |
| 2011/0172312 A1 | 7/2011 | Miller et al. | |
| 2011/0207828 A1 | 8/2011 | Miller et al. | |
| 2011/0214679 A1 | 9/2011 | Chua | |
| 2011/0218208 A1 | 9/2011 | Hinman et al. | |
| 2011/0263720 A1 | 10/2011 | Paisley et al. | |
| 2011/0269776 A1 | 11/2011 | Miller | |
| 2012/0101169 A1 | 4/2012 | Hawi | |
| 2012/0122934 A1 | 5/2012 | Jankowski et al. |
| 2012/0122969 A1 | 5/2012 | Miller |
| 2012/0136048 A1 | 5/2012 | Miller et al. |
| 2012/0295985 A1 | 11/2012 | Miller et al. |
| 2013/0109759 A1 | 5/2013 | Miller |
| 2013/0116336 A1 | 5/2013 | Shrader |
| 2013/0267538 A1 | 10/2013 | Walkinshaw et al. |
| 2013/0345312 A1 | 12/2013 | Jankowski et al. |
| 2014/0031432 A1 | 1/2014 | Jankowski et al. |
| 2014/0031433 A1 | 1/2014 | Miller et al. |
| 2014/0221674 A1 | 8/2014 | Wesson et al. |
| 2014/0243424 A1 | 8/2014 | Mollard et al. |
| 2014/0249332 A1 | 9/2014 | Mollard |
| 2014/0256830 A1 | 9/2014 | Hinman et al. |
| 2014/0275045 A1 | 9/2014 | Hinman et al. |
| 2014/0275054 A1 | 9/2014 | Hinman et al. |
| 2015/0057363 A1 | 2/2015 | Miller et al. |
| 2015/0216820 A1 | 8/2015 | Miller et al. |
| 2015/0218079 A1 | 8/2015 | Shrader et al. |
| 2016/0024085 A1 | 1/2016 | Hinman et al. |
| 2016/0039776 A1 | 2/2016 | Hinman et al. |
| 2016/0115141 A1 | 4/2016 | Hinman et al. |
| 2017/0313649 A1 | 11/2017 | Jankowski et al. |
| 2018/0000749 A1 | 1/2018 | Mollard et al. |
| 2018/0002247 A1 | 1/2018 | Mollard et al. |
| 2018/0333389 A1 | 11/2018 | Miller |
| 2018/0362492 A1 | 12/2018 | Giannousis et al. |
| 2018/0370892 A1 | 12/2018 | Hinman et al. |
| 2019/0029975 A1 | 1/2019 | Shrader |
| 2019/0241497 A1 | 8/2019 | Hinman |
| 2019/0330159 A1 | 10/2019 | Kitano et al. |

FOREIGN PATENT DOCUMENTS

| | | |
|---|---|---|
| EP | 0 831 092 B1 | 3/1998 |
| EP | 1 454 627 A1 | 9/2004 |
| JP | 10-147575 A | 6/1998 |
| JP | H11 80149 A | 3/1999 |
| JP | 2009 278930 A | 12/2009 |
| WO | WO 00/17190 A2 | 3/2000 |
| WO | WO 00/17190 A3 | 3/2000 |
| WO | WO 00/78296 A2 | 12/2000 |
| WO | WO 00/78296 A3 | 12/2000 |
| WO | WO 02/12221 A1 | 2/2002 |
| WO | WO 02/47680 A2 | 6/2002 |
| WO | WO 02/47680 A3 | 6/2002 |
| WO | WO 02/47680 A9 | 6/2002 |
| WO | WO 03/016323 A1 | 2/2003 |
| WO | WO 03/064403 A1 | 8/2003 |
| WO | WO 2004/003565 A2 | 1/2004 |
| WO | WO 2007/095630 A2 | 8/2007 |
| WO | WO 2007/095630 A3 | 8/2007 |
| WO | WO 2009/111543 A2 | 9/2009 |
| WO | WO 2011/041452 A2 | 4/2011 |
| WO | WO 2011/113018 A1 | 9/2011 |
| WO | WO 2012/019029 A2 | 2/2012 |
| WO | WO 2012/019029 A3 | 2/2012 |
| WO | WO 2012/019032 A1 | 2/2012 |
| WO | WO 2012/154613 A1 | 11/2012 |
| WO | WO 2012/170773 A1 | 12/2012 |
| WO | WO 2013/006736 A1 | 1/2013 |
| WO | WO 2016/100576 | 6/2016 |
| WO | WO 2016/100579 | 6/2016 |
| WO | WO 2016/114860 | 7/2016 |
| WO | WO 2017/106803 | 6/2017 |
| WO | WO 2017/123823 | 6/2017 |
| WO | WO 2017/123820 | 7/2017 |
| WO | WO 2017/123822 | 7/2017 |
| WO | WO 2018/081644 A1 | 5/2018 |
| WO | WO 2018/093957 A1 | 5/2018 |
| WO | WO 2018/129411 A1 | 7/2018 |
| WO | WO 2018/191732 A1 | 10/2018 |

OTHER PUBLICATIONS

Barbiroli et al. (1995). "Lipoic (Thioctic) Acid Increases Brain Energy Availability and Skeletal Muscle Performance as Shown by

(56) References Cited

OTHER PUBLICATIONS

In Vivo 31P-MRS in a Patient with Mitochondrial Cytopathy," J Neurol. 242(7):472-477.
Braga et al., "Crystal Polymorphism and Multiple Crystal Forms", Struct Bond, 2009, vol. 132, pp. 25-50; D01:10.1007/4302008_7.
Cadenas et al., "The Lag Phase", (1997), Free Radic. Res, vol. 28, pp. 601-609.
Caira, "Crystalline Polymorphism of Organic Compounds", Topics In Current Chemistry, Springer, Berlin, DE, vol. 198, Jan. 1998, pp. 163-208.
Carey, F. Fourth Edition Organic Chemistry McGraw-Hill 2000, pp. 286-288.
Chariot et al. (Apr. 1994). "Determination of the Blood Lactate: Pyruvate Ratio As a Noninvasive Test for the Diagnosis of Zidovudine Myopathy," Arthritis & Rheumatism 37(4):583-586.
Chariot et al. (Jul. 1994). "Optimal Handling of Blood Samples for Routine Measurement of Lactate and Pyruvate," Arch. Pathol. Lab. Med. 118(7):695-697.
Chugani et al. (May 1999). "Evidence of Altered Energy Metabolism in Autistic Children," Progress in Neuro-Psychopharmacology & Biological Psychiatry 23(4):635-641.
Cohen et al., "Studies on the total synthesis of (2R, 4'R, 8'R)-.alpha.-tocopherol (vitamin E). Stereospecific cyclizations leading to optically active chromans", The Journal Of Organic Chemistry, American Chemical Society, J. Org. Chem. 1981, vol. 46, No. 12, Jun. 1981, pp. 2445-2450, XP002638190.
Coleman et al., (Mar. 1985), "Autism and Lactic Acidosis," Journal of Autism and Developmental Disorders, 15(1):1-8.
Deschauer et al., (2005) "A Novel ANT1 Gene Mutation with Probable Germline Mosaicism in Autosomal Dominant Progressive External Ophthalmoplegia," Neuromuscular Disorders 15:311-315.
Erhola et al., (1997) "Biomarker Evidence of DNA Oxidation in Lung Cancer Patients: Association of Urinary 8-Hydroxy-2'-Deoxyguanosine Excretion with Radiotherapy, Chemotherapy, and Response to Treatment," FEBS Letters 409(2):287-291.
Fabrizi et al., (1996) "Autosomal Dominant Limb Girdle Myopathy with Ragged-Red Fibers and Cardiomyopathy. A Pedigree Study by In Vivo 31P-MR Spectroscopy Indicating a Multisystem Mitochondrial Defect," Journal of the Neurological Sciences 137(1):20-27.
Filipek et al., (Dec. 2004). "Relative Carnitine Deficiency in Autism," Journal of Autism and Developmental Disorders 34(6):615-623.
G. Patrick Stahly, "Diversity in Single- and Multiple-Component Crystals. The Search for and Prevalence of Polymorphs and Cocrystals", Crystal Growth & Design, 2007, vol. 7, No. 6, pp. 1007-1026.
Gempel et al. (2007) "The Myopathic Form of Coenzyme Q10 Deficiency is Caused by Mutations in the Electron-Transferring-Flavoprotein Dehydrogenase (ETFDH) Gene," Brain 130(8):2037-2044.
Harman D., "Aging: A theory based on free-radical and radiation chemistry," (1956), J. Gerontolology, pp. 298-300.
Hilfiker et al., "Relevance of Solid-state Properties for Pharmaceutical Products", 2006, pp. 1-19.
Honda, M. et al. (2000). "Correlation of Urinary 8-Hydroxy-2'-Deoxyguanosine (8-OHdG), a Biomarker of Oxidative DNA Damage, and Clinical Features of Hematological Disorders: A Pilot Study," Leukemia Research 24(6):461-468.
International search report and written opinion of PCT/US2015/066211 dated Mar. 21, 2016, 14 pages.
Ishikawa et al. (May 2, 2008). "ROS-Generating Mitochondrial DNA Mutations Can Regulate Tumor Cell Metastasis," Science 320:661-664.
Isobe et al., (2002) "Synthesis and Activity of a Metabolite of (S)-6-Amino-5-(6-Hydroxy-2,5,7,8-Tetramethylchroman-2-Carboxamido)-3-Methyl-1-Phenyl-2,4-(1H,3H)-Pyrimidinedione (CX-659S)," Chem. Pharm. Bull., 50(10):1418-1420.
Jauslin et al., "A Cellular Model for Friedreich Ataxia Reveals Small-Molecule Glutathione Peroxidase Mimetics as Novel Treatment Strategy," Human Molecular Genetics, (2002), 11(24):3055-3063.
Jauslin et al., (Oct. 2003, e-pub. Aug. 15, 2003), "Mitochondria-Targeted Antioxidants Protect Friedreich Ataxia Fibroblasts from Endogenous Oxidative Stress More Effectively Than Untargeted Antioxidants", The FASEB Journal express article 10.1096/fj.03-0240fje, 10 pages.
Kaufmann et al., (Apr. 27, 2004). "Cerebral Lactic Acidosis Correlates with Neurological Impairment in MELAS," Neurology 62, pp. 1297-1302.
Kim et al., (May 2004). "Urinary 8-Hydroxy-2'-Deoxyguanosine as a Biomarker of Oxidative DNA Damage in Workers Exposed to Fine Particulates," Environmental Health Perspectives 112(6):666-671.
Koufaki et al., "Chroman/Catechol Hybrids: Synthesis and Evaluation of Their Activity against Oxidative Stress Induced Cellular Damage", Journal of Medicinal Chemistry, 2006, vol. 49, No. 1, pp. 300-306.
Kozma, "CRC Handbook of Optical Resolutions via Diasteriomeric Salt Formation", CRC Press 2002, Excerpt, 19 pages.
Lamperti et al., "Cerebellar Ataxia and Coenzyme Q10 Deficiency," Neurology 60, Apr. 2003, pp. 1206:1208.
László et al. (1994) "Serum Serotonin, Lactate and Pyruvate Levels in Infantile Autistic Children," Clinica Chimica Acta 229:205-207.
Lee, (1992) "Diffusion-Controlled Matrix Systems," Chapters in Treatise on Controlled Dug Delivery, Kydonieus, A. ed., Marcel Dekker, Inc., New York, NY, pp. 155-197.
Luft, (Sep. 1994), "The Development of Mitochondrial Medicine," PNAS USA 91:8731-8738.
Lynch et al. (May 2002, e-pub. Feb. 25, 2002), "Near Infrared Muscle Spectroscopy in Patients with Friedreich's Ataxia," Muscle and Nerve 25(5):664-673.
Matthews et al. (Apr. 1991). "In Vivo Magnetic Resonance Spectroscopy of Brain and Muscle in a Type of Mitochondrial Encephalomyopathy (MERRF)," Annals of Neurology 29(4):435-438.
Medline Plus (Nov. 12, 2012). "Friedreich's Ataxia," updated by K. Sheth, MD, Department of Neurology, University of Maryland School of Medicine, Baltimore, MD, located at <http://www.nlm.nih.gov/medlineplus/ency/article/001411.htm>, last visited on Jul. 18, 2013, three pages.
Munnich et al. (1992). "Clinical Aspects of Mitochondrial Disorders," Journal of Inherited Metabolic Disease 15(4):448-455.
Musumeci et al., "Familial Cerebellar Ataxia with Muscle Coenzyme Q10 Deficiency," Neurology, (2001), vol. 56, pp. 849-855.
Nie et al. (2007, e-pub. Jun. 15, 2007). "Enhanced Radical Scavenging Activity by Antioxidant-Functionalized Gold Nanoparticles: A Novel Inspiration for Development of New Artificial Antioxidants," Free Radical Biology and Medicine 43:1243-1254.
Oliveira et al. (2005). "Mitochondrial Dysfunction in Autism Spectrum Disorders: a Population-Based Study," Developmental Medicine & Child Neurology 47:185-189.
Pich et al. (2002). "Ubiquinol and a Coenzyme Q Reducing System Protect Platelet Mitochondrial Function of Transfusional Buffy Coats from Oxidative Stress", Free Radical Research 36(4):429-436.
Pilger et al. (2001). "Longitudinal Study of Urinary 8-Hydroxy-2'-Deoxyguanosine Excretion in Healthy Adults," Free Radical Research 35(3):273-280.
Piña et al. (2003). "Exercise and Heart Failure: A Statement from the American Heart Association Committee on Exercise, Rehabilitation, and Prevention," Circulation 107:1210-1225.
Poling et al. (Feb. 2006). "Developmental Regression and Mitochondrial Dysfunction in a Child with Autism," J. Child Neurol. 21(2):170-172.
Rolfe, "In Vivo Near-Infrared Spectroscopy," Annual Review of Biomedical Engineering, 2000, vol. 2, pp. 715-754.
Rossignol et al., "Evidence of Mitochondrial Dysfunction in Autism and Implications for Treatment," American Journal of Biochemistry and Biotechnology, 2008, 4(2):208-217.
Strangman et al., (2002) "Non-Invasive Neuroimaging Using Near-Infrared Light," Biol. Psychiatry 52:679-693.

(56) References Cited

OTHER PUBLICATIONS

Taivassalo et al. (Jan. 2002, e-pub. Nov. 15, 2001). "Venous Oxygen Levels During Aerobic Forearm Exercise: An Index of Impaired Oxidative Metabolism in Mitochondrial Myopathy," Ann. Neurol. 51(1):38-44.

Taivassalo et al., "The Spectrum of Exercise Tolerance in Mitochondrial Myopathies: A Study of 40 Patients," Brain, 2003, 126:413-423.

Takashi Kojima, "Aiming toward the improvement of efficiency of the crystal form selection in medical supply developing", Journal of Pharmaceutical Science and Technology, Japan, Sep. 2008, vol. 68, No. 5, pp. 344-349 with the English mashine translation.

Ueda et al. (Feb. 1997). "Evaluation of Changes in Hepatic Energy Metabolism During Exercise by Ketone Body Ratio in Humans," J. Cardiol. 29(2):95-102. (Translation of Abstract Only).

UMC-Cares (May 3, 2007). "Friedreich's Ataxia," previously located at <http://www.umccares.org/health_info/ADAM/Articles/001411.asp>, now located at <http://web.archive.org/web/20070503123643/http://www.umc-cares.org/health_info/ADAM/Articles/001411.asp>, last visited on Jul. 19, 2013, three pages.

Valko et al, "Role of oxygen radicals in DNA damage and cancer incidence," (2004), Mol. and Cell. Biochemistry, vol. 266, pp. 37-56.

Van Beekvelt, M.C.P. et al. (Oct. 1999). "Quantitative Near-Infrared Spectroscopy Discriminates Between Mitochondrial Myopathies and Normal Muscle," Annals of Neurology 46(4):667-670.

West, "Solid State Chemistry and its Applications", Wiley, New York, Mar. 3, 1988, p. 358.

First Examination report for an Australian Patent Application No. 2022202949 dated Apr. 19, 2023.

Balbach et al., "Pharmaceutical evaluation of early development candidates the 100 mg-approach", International Journal of Pharmaceutics 275 (2004) 1-12; doi:10.1016/j.ijpharm.2004.01.034.

Singhal et al., "Drug polymorphism and dosage form design: a practical perspective", Advanced Drug Delivery Reviews 56 (2004) 335-347; doi:10.1016/j.addr.2003.10.008.

\* cited by examiner

POLYMORPHIC FORMS OF (R)-2-HYDROXY-2-METHYL-4-(2,4,5-TRIMETHYL-3,6-DIOXOCYCLOHEXA-1,4-DIENYL) BUTANAMIDE

The application is a continuation of U.S. patent application Ser. No. 16/919,044, filed Jul. 1, 2020, entitled POLYMORPHIC AND AMORPHOUS FORMS OF (R)-2-HYDROXY-2-METHYL-4-(2,4,5-TRIMETHYL-3,6-DIOXOCYCLOHEXA-1,4-DIENYL)BUTANAMIDE, which is a continuation of U.S. patent application Ser. No. 16/354,070, filed Mar. 14, 2019, entitled POLYMORPHIC AND AMORPHOUS FORMS OF (R)-2-HYDROXY-2-METHYL-4-(2,4,5-TRIMETHYL-3,6-DIOXOCYCLOHEXA-1,4-DIENYL)BUTANAMIDE, which is a continuation of U.S. patent application Ser. No. 15/536,603, filed Jun. 15, 2017, entitled POLYMORPHIC AND AMORPHOUS FORMS OF (R)-2-HYDROXY-2-METHYL-4-(2,4,5-TRIMETHYL-3,6-DIOXOCYCLOHEXA-1,4-DIENYL)BUTANAMIDE, which is a national-stage filing under 35 U.S.C. 371 of PCT/US2015/066211, filed Dec. 16, 2015, entitled POLYMORPHIC AND AMORPHOUS FORMS OF (R)-2-HYDROXY-2-METHYL-4-(2,4,5-TRIMETHYL-3,6-DIOXOCYCLOHEXA-1,4-DIENYL)BUTANAMIDE, which claims priority to, and the benefit of, U.S. Provisional Patent Application No. 62/092,743, filed Dec. 16, 2014, entitled POLYMORPHIC AND AMORPHOUS FORMS OF (R)-2-HYDROXY-2-METHYL-4-(2,4,5-TRIMETHYL-3,6-DIOXOCYCLOHEXA-1,4-DIENYL)BUTANAMIDE, and U.S. Provisional Patent Application No. 62/133,276, filed Mar. 13, 2015, entitled POLYMORPHIC AND AMORPHOUS FORMS OF (R)-2-HYDROXY-2-METHYL-4-(2,4,5-TRIMETHYL-3,6-DIOXOCYCLOHEXA-1,4-DIENYL)BUTANAMIDE, the contents of each of these applications are herein incorporated by reference in their entirety for all purposes.

TECHNICAL FIELD

The application discloses compositions and methods useful for treatment or suppression of diseases, developmental delays and symptoms related to oxidative stress disorders. Examples of such disorders include mitochondrial disorders, impaired energy processing disorders, neurodegenerative diseases and diseases of aging. The application further discloses methods of making such compositions.

BACKGROUND

Oxidative stress is caused by disturbances to the normal redox state within cells. An imbalance between routine production and detoxification of reactive oxygen species such as peroxides and free radicals can result in oxidative damage to the cellular structure and machinery. The most important source of reactive oxygen species under normal conditions in aerobic organisms is probably the leakage of activated oxygen from mitochondria during normal oxidative respiration. Impairments associated with this process are suspected to contribute to mitochondrial disease, neurodegenerative disease, and diseases of aging.

Mitochondria are organelles in eukaryotic cells, popularly referred to as the "powerhouse" of the cell. One of their primary functions is oxidative phosphorylation. The molecule adenosine triphosphate (ATP) functions as an energy "currency" or energy carrier in the cell, and eukaryotic cells derive the majority of their ATP from biochemical processes carried out by mitochondria. These biochemical processes include the citric acid cycle (the tricarboxylic acid cycle, or Krebs cycle), which generates reduced nicotinamide adenine dinucleotide (NADH+H+) from oxidized nicotinamide adenine dinucleotide (NAD+), and oxidative phosphorylation, during which NADH+H+ is oxidized back to NAD+. The citric acid cycle also reduces flavin adenine dinucleotide, or FAD, to FADH2; FADH2 also participates in oxidative phosphorylation.

The electrons released by oxidation of NADH+H+ are shuttled down a series of protein complexes (Complex I, Complex II, Complex III, and Complex IV) known as the mitochondrial respiratory chain. These complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP.

When cells in an organism are temporarily deprived of oxygen, anaerobic respiration is utilized until oxygen again becomes available or the cell dies. The pyruvate generated during glycolysis is converted to lactate during anaerobic respiration. The buildup of lactic acid is believed to be responsible for muscle fatigue during intense periods of activity, when oxygen cannot be supplied to the muscle cells. When oxygen again becomes available, the lactate is converted back into pyruvate for use in oxidative phosphorylation.

Oxygen poisoning or toxicity is caused by high concentrations of oxygen that may be damaging to the body and increase the formation of free-radicals and other structures such as nitric oxide, peroxynitrite, and trioxidane. Normally, the body has many defense systems against such damage but at higher concentrations of free oxygen, these systems are eventually overwhelmed with time, and the rate of damage to cell membranes exceeds the capacity of systems which control or repair it. Cell damage and cell death then results.

Qualitative and/or quantitative disruptions in the transport of oxygen to tissues result in energy disruption in the function of red cells and contribute to various diseases such as haemoglobinopathies. Haemoglobinopathy is a kind of genetic defect that results in abnormal structure of one of the globin chains of the hemoglobin molecule. Common haemoglobinopathies include thalassemia and sickle-cell disease. Thalassemia is an inherited autosomal recessive blood disease. In thalassemia, the genetic defect results in reduced rate of synthesis of one of the globin chains that make up hemoglobin. While thalassemia is a quantitative problem of too few globins synthesized, sickle-cell disease is a qualitative problem of synthesis of an incorrectly functioning globin. Sickle-cell disease is a blood disorder characterized by red blood cells that assume an abnormal, rigid, and sickle shape. Sickling decreases the cells' flexibility and results in their restricted movement through blood vessels, depriving downstream tissues of oxygen.

Mitochondrial dysfunction contributes to various disease states. Some mitochondrial diseases are due to mutations or deletions in the mitochondrial genome. If a threshold proportion of mitochondria in the cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved. Some examples of mitochondrial diseases are Friedreich's ataxia (FRDA), Leber's Hereditary Optic Neuropathy (LHON), mitochondrial myopathy, encephalopathy, lactacidosis, and stroke (MELAS), Myoclonus Epilepsy Associated with Ragged-Red Fibers (MERRF) syndrome, Leigh's syndrome, and respiratory chain disorders. Most mitochondrial diseases involve children who manifest the signs and symptoms of accelerated aging, including neurodegenerative diseases, stroke, blindness, hearing impairment, vision impairment, diabetes, and heart failure.

Friedreich's ataxia is an autosomal recessive neurodegenerative and cardiodegenerative disorder caused by decreased levels of the protein Frataxin. The disease causes the progressive loss of voluntary motor coordination (ataxia) and cardiac complications. Symptoms typically begin in childhood, and the disease progressively worsens as the patient grows older; patients eventually become wheelchair-bound due to motor disabilities.

Leber's Hereditary Optic Neuropathy (LHON) is a disease characterized by blindness which occurs on average between 27 and 34 years of age. Other symptoms may also occur, such as cardiac abnormalities and neurological complications.

Mitochondrial myopathy, encephalopathy, lactacidosis, and stroke (MELAS) can manifest itself in infants, children, or young adults. Strokes, accompanied by vomiting and seizures, are one of the most serious symptoms; it is postulated that the metabolic impairment of mitochondria in certain areas of the brain is responsible for cell death and neurological lesions, rather than the impairment of blood flow as occurs in ischemic stroke.

Myoclonus Epilepsy Associated with Ragged-Red Fibers (MERRF) syndrome is one of a group of rare muscular disorders that are called mitochondrial encephalomyopathies. Mitochondrial encephalomyopathies are disorders in which a defect in the genetic material arises from a part of the cell structure that releases energy (mitochondria). This can cause a dysfunction of the brain and muscles (encephalomyopathies). The mitochondrial defect as well as "ragged-red fibers" (an abnormality of tissue when viewed under a microscope) are always present. The most characteristic symptom of MERRF syndrome is myoclonic seizures that are usually sudden, brief, jerking, spasms that can affect the limbs or the entire body, difficulty speaking (dysarthria), optic atrophy, short stature, hearing loss, dementia, and involuntary jerking of the eyes (nystagmus) may also occur.

Leigh's syndrome is a rare inherited neurometabolic disorder characterized by degeneration of the central nervous system where the symptoms usually begin between the ages of 3 months to 2 years and progress rapidly. In most children, the first signs may be poor sucking ability and loss of head control and motor skills. These symptoms may be accompanied by loss of appetite, vomiting, irritability, continuous crying, and seizures. As the disorder progresses, symptoms may also include generalized weakness, lack of muscle tone, and episodes of lactic acidosis, which can lead to impairment of respiratory and kidney function. Heart problems may also occur.

Co-Enzyme Q10 Deficiency is a respiratory chain disorder, with syndromes such as myopathy with exercise intolerance and recurrent myoglobin in the urine manifested by ataxia, seizures or mental retardation and leading to renal failure (Di Mauro et al., (2005) *Neuromusc. Disord.*, 15:311-315), "Childhood-onset cerebellar ataxia and cerebellar atrophy," (Masumeci et al., (2001) Neurology 56:849-855 and Lamperti et al., (2003) 60:1206:1208); and infantile encephalomyopathy associated with nephrosis. Biochemical measurement of muscle homogenates of patients with CoQ10 deficiency showed severely decreased activities of respiratory chain complexes I and II+III, while complex IV (COX) was moderately decreased (Gempel et al., (2007) *Brain,* 130(8):2037-2044).

Complex I Deficiency or NADH dehydrogenase NADH-CoQ reductase deficiency is a respiratory chain disorder, with symptoms classified by three major forms: (1) fatal infantile multisystem disorder, characterized by developmental delay, muscle weakness, heart disease, congenital lactic acidosis, and respiratory failure; (2) myopathy beginning in childhood or in adult life, manifesting as exercise intolerance or weakness; and (3) mitochondrial encephalomyopathy (including MELAS), which may begin in childhood or adult life and consists of variable combinations of symptoms and signs, including ophthalmoplegia, seizures, dementia, ataxia, hearing loss, pigmentary retinopathy, sensory neuropathy, and uncontrollable movements.

Complex II Deficiency or Succinate dehydrogenase deficiency is a respiratory chain disorder with symptoms including encephalomyopathy and various manifestations, including failure to thrive, developmental delay, hypotonia, lethargy, respiratory failure, ataxia, myoclonus and lactic acidosis.

Complex III Deficiency or Ubiquinone-cytochrome C oxidoreductase deficiency is a respiratory chain disorder with symptoms categorized in four major forms: (1) fatal infantile encephalomyopathy, congenital lactic acidosis, hypotonia, dystrophic posturing, seizures, and coma; (2) encephalomyopathies of later onset (childhood to adult life): various combinations of weakness, short stature, ataxia, dementia, hearing loss, sensory neuropathy, pigmentary retinopathy, and pyramidal signs; (3) myopathy, with exercise intolerance evolving into fixed weakness; and (4) infantile histiocytoid cardiomyopathy.

Complex IV Deficiency or Cytochrome C oxidase deficiency is a respiratory chain disorder with symptoms categorized in two major forms: (1) encephalomyopathy, where patients typically are normal for the first 6 to 12 months of life and then show developmental regression, ataxia, lactic acidosis, optic atrophy, ophthalmoplegia, nystagmus, dystonia, pyramidal signs, respiratory problems and frequent seizures; and (2) myopathy with two main variants: (a) Fatal infantile myopathy—may begin soon after birth and accompanied by hypotonia, weakness, lactic acidosis, ragged-red fibers, respiratory failure, and kidney problems: and (b) Benign infantile myopathy—may begin soon after birth and accompanied by hypotonia, weakness, lactic acidosis, ragged-red fibers, respiratory problems, but (if the child survives) followed by spontaneous improvement.

Complex V Deficiency or ATP synthase deficiency is a respiratory chain disorder including symptoms such as slow, progressive myopathy.

CPEO or Chronic Progressive External Ophthalmoplegia Syndrome is a respiratory chain disorder including symptoms such as visual myopathy, retinitis pigmentosa, or dysfunction of the central nervous system.

Kearns-Sayre Syndrome (KSS) is a mitochondrial disease characterized by a triad of features including: (1) typical onset in persons younger than age 20 years; (2) chronic, progressive, external ophthalmoplegia; and (3) pigmentary degeneration of the retina. In addition, KSS may include cardiac conduction defects, cerebellar ataxia, and raised cerebrospinal fluid (CSF) protein levels (e.g., >100 mg/dL). Additional features associated with KSS may include myopathy, dystonia, endocrine abnormalities (e.g., diabetes, growth retardation or short stature, and hypoparathyroidism), bilateral sensorineural deafness, dementia, cataracts, and proximal renal tubular acidosis.

Maternally inherited diabetes and deafness (MIDD) is a mitochondrial disorder characterized by maternally transmitted diabetes and sensorineural deafness. In most cases, MIDD is caused by a point mutation in the mitochondrial gene MT-TL1, encoding the mitochondrial tRNA for leucine, and in rare cases in MT-TE and MT-TK genes, encoding the mitochondrial tRNAs for glutamic acid, and lysine, respectively.

In addition to congenital disorders involving inherited defective mitochondria, acquired mitochondrial dysfunction contributes to diseases, particularly neurodegenerative disorders associated with aging like Parkinson's, Alzheimer's, and Huntington's Diseases. The incidence of somatic mutations in mitochondrial DNA rises exponentially with age; diminished respiratory chain activity is found universally in aging people. Mitochondrial dysfunction is also implicated in excitotoxic, neuronal injury, such as that associated with cerebrovascular accidents, seizures and ischemia.

Some of the above diseases appear to be caused by defects in Complex I of the respiratory chain. Electron transfer from Complex I to the remainder of the respiratory chain is mediated by the compound coenzyme Q (also known as Ubiquinone). Oxidized coenzyme Q ($CoQ_{ox}$ or Ubiquinone) is reduced by Complex I to reduced coenzyme Q ($CoQ_{red}$ or Ubiquinol) The reduced coenzyme Q then transfers its electrons to Complex III of the respiratory chain, where it is re-oxidized to $CoQ_{ox}$ (Ubiquinone). $CoQ_{ox}$ can then participate in further iterations of electron transfer.

Very few treatments are available for patients suffering from these mitochondrial diseases. Recently, the compound Idebenone has been proposed for treatment of Friedreich's ataxia. While the clinical effects of Idebenone have been relatively modest, the complications of mitochondrial diseases can be so severe that even marginally useful therapies are preferable to the untreated course of the disease. Another compound, MitoQ, has been proposed for treating mitochondrial disorders (see U.S. Pat. No. 7,179,928); clinical results for MitoQ have not yet been reported. Administration of coenzyme Q10 (CoQ10) and vitamin supplements has shown only transient beneficial effects in individual cases of KSS. CoQ10 supplementation has also been used for the treatment of CoQ10 deficiency with mixed results.

Oxidative stress is suspected to be important in neurodegenerative diseases such as Motor Neuron Disease, Amyotrophic Lateral Sclerosis (ALS), Creutzfeldt-Jakob disease, Machado-Joseph disease, Spino-cerebellar ataxia, Multiple sclerosis (MS), Parkinson's disease, Alzheimer's disease, and Huntington's disease. Oxidative stress is thought to be linked to certain cardiovascular disease and also plays a role in the ischemic cascade due to oxygen reperfusion injury following hypoxia. This cascade includes both strokes and heart attacks.

Damage accumulation theory, also known as the free radical theory of aging, invokes random effects of free radicals produced during aerobic metabolism that cause damage to DNA, lipids and proteins and accumulate over time. The concept of free radicals playing a role in the aging process was first introduced by Himan D (1956), "Aging—A theory based on free-radical and radiation chemistry," *J. Gerontol.* 11, 298-300.

According to the free radical theory of aging, the process of aging begins with oxygen metabolism (Valko et al, (2004), "Role of oxygen radicals in DNA damage and cancer incidence," *Mol. Cell. Biochem.*, 266, 37-56). Even under ideal conditions some electrons "leak" from the electron transport chain. These leaking electrons interact with oxygen to produce superoxide radicals, so that under physiological conditions, about 1-3% of the oxygen molecules in the mitochondria are converted into superoxide. The primary site of radical oxygen damage from superoxide radical is mitochondrial DNA (mtDNA) (Cadenas et al, (2000) Mitochondrial free radical generation, oxidative stress and aging, *Free Radic. Res,* 28, 601-609). The cell repairs much of the damage done to nuclear DNA (nDNA) but mtDNA repair seems to be less efficient. Therefore, extensive mtDNA damage accumulates over time and shuts down mitochondria causing cells to die and the organism to age.

Some of the diseases associated with increasing age are cancer, diabetes mellitus, hypertension, atherosclerosis, ischemia/reperfusion injury, rheumatoid arthritis, neurodegenerative disorders such as dementia, Alzheimer's and Parkinson's. Diseases resulting from the process of aging as a physiological decline include decreases in muscle strength, cardiopulmonary function, vision and hearing as well as wrinkled skin and graying hair.

The ability to adjust biological production of energy has applications beyond the diseases described above. Various other disorders can result in suboptimal levels of energy biomarkers (sometimes also referred to as indicators of energetic function), such as ATP levels. Treatments for these disorders are also needed, in order to modulate one or more energy biomarkers to improve the health of the patient. In other applications, it can be desirable to modulate certain energy biomarkers away from their normal values in an individual that is not suffering from disease. For example, if an individual is undergoing an extremely strenuous undertaking, it can be desirable to raise the level of ATP in that individual.

Certain polymorphic or amorphous forms of a drug can have advantageous characteristics versus other forms; for example, increased stability, increased solubility, better handling properties, lack of associated toxic solvents, and increased purity.

Example 16 of PCT Application No. PCT/US2008/082374, published as WO 2009/061744 on May 14, 2009, describes a synthesis for racemic 2-hydroxy-2-methyl-4-(2,4,5-trimethyl-3,6-dioxocyclohexa-1,4-dienyl)butanamide; this Example does not specifically describe the synthesis of any particular polymorphic or amorphous form for (R)-2-hydroxy-2-methyl-4-(2,4,5-trimethyl-3,6-dioxocyclohexa-1,4-dienyl)butanamide or any particular stereoisomer thereof.

BRIEF SUMMARY OF THE INVENTION

In one aspect of the invention is a polymorph of an anhydrate, a hydrate, or a solvate of (R)-2-hydroxy-2-methyl-4-(2,4,5-trimethyl-3,6-dioxocyclohexa-1,4-dienyl) butanamide, wherein the polymorph is selected from the group consisting of Form I, Form II, Form III, Form IV, Form V, and Form VI as described herein.

In another aspect of the invention is a polymorph of an anhydrate of (R)-2-hydroxy-2-methyl-4-(2,4,5-trimethyl-3,6-dioxocyclohexa-1,4-dienyl)butanamide, wherein the polymorph is Form I as described herein. In some embodiments, the polymorph has a powder x-ray diffraction pattern substantially as shown in FIG. 10. In some embodiments, a powder X-ray diffraction pattern for the polymorph comprises characteristic peaks at the following angular positions, wherein the angular positions may vary by ±0.2: 12.06, 17.03, and 17.26. In some embodiments, a powder X-ray diffraction pattern for the polymorph comprises characteristic peaks at least at the following angular positions, wherein the angular positions may vary by ±0.2: 12.06, 17.03, and 17.26. In some embodiments, a powder X-ray diffraction pattern for the polymorph comprises characteristic peaks at the following angular positions, wherein the angular positions may vary by ±0.2: 12.06, 15.33, 17.03, and 17.26. In some embodiments, a powder X-ray diffraction pattern for the polymorph comprises characteristic peaks at least at the following angular positions, wherein the angular positions may vary by ±0.2: 12.06, 15.33, 17.03, 17.26, and 18,72. In some embodiments, a powder X-ray diffraction pattern for the polymorph comprises characteristic peaks at the following angular positions, where in the angular positions may vary by +0.2: 12.06, 15.33, 17.03, 17.26, and 18.72. In some embodiments, a powder X-ray diffraction pattern for the polymorph comprises characteristic peaks at the following angular positions, wherein the angular positions may vary by ±0.2: 7.67, 10.75, 12.06, 15.33, 16.41, 17.03, 17.26, 18.72, 20.04, and 23.92. In some embodiments, a powder X-ray diffraction pattern for the polymorph comprises characteristic peaks at the following angular positions, wherein the angular positions may vary by ±0.2: 7.67, 10.75, 12.06, 15.33, 16.41, 17.03, 17.26, 18.72, 20.04, 20.64, 20.91, 21.14, 22.58, 23.13, 23.92, 24.19, 24.53, 27.21, and 27.56. In some embodiments, a powder X-ray diffraction pattern for the polymorph comprises characteristic peaks at the following angular positions, wherein the angular positions may vary by ±0.2: 5.48, 7.67, 10.75, 12.06, 15.33, 16.41, 17.03, 17.26, 17.71, 17.94, 18.40, 18.72, 19.51, 20.04, 20.64, 20.91, 21.14, 21.55, 21.91, 22.25, 22.58, 23.13, 23.41, 23.92, 24.19, 24.53, 25.64, 26.13, 26.34, 27.21, 27.56, 28.01, 29.04, and 29.46. In some embodiments, including any of the foregoing embodiments, the angular positions may vary by ±0.1. In some embodiments, including any of the foregoing embodiments, the angular positions may vary by ±0.05. In some embodiments, including any of the foregoing embodiments, the angular positions may vary by ±0.02. In some embodiments, including any of the foregoing embodiments, the polymorph is isolated. In some embodiments, including any of the foregoing embodiments, the polymorph is present in a composition, wherein the composition is essentially free of Forms II-VI, wherein Forms II-VI are described in Table A or Tables 3-7 respectively. In some embodiments, including any of the foregoing embodiments, the polymorph is present in a composition, wherein at least about 95% of the composition is the polymorph, exclusive of any solvents, carriers or excipients.

In another aspect of the invention is a polymorph of an anhydrate of (R)-2-hydroxy-2-methyl-4-(2,4,5-trimethyl-3,6-dioxocyclohexa-1,4-dienyl)butanamide, wherein the polymorph is Form V as described herein. In some embodiments, the polymorph has a powder x-ray diffraction pattern substantially as shown in a) or b) of FIG. 30. In some embodiments, a powder X-ray diffraction pattern for the polymorph comprises characteristic peaks at the following angular positions, wherein the angular positions may vary by ±0.2: 9.61, 11.49, and 15.45. In some embodiments, a powder X-ray diffraction pattern for the polymorph comprises characteristic peaks at least at the following angular positions, wherein the angular positions may vary by ±0.2: 9.61, 11.49, and 15.45. In some embodiments, a powder X-ray diffraction pattern for the polymorph comprises characteristic peaks at least at the following angular positions, wherein the angular positions may vary by ±0.2: 9.61, 11.49, 15.45, and 23.96. In some embodiments, a powder X-ray diffraction pattern for the polymorph comprises characteristic peaks at least at the following angular positions, wherein the angular positions may vary by ±0.2: 9.61, 11.49, 14.80, 15.45, 23.96. In some embodiments, a powder X-ray diffraction pattern for the polymorph comprises characteristic peaks at the following angular positions, wherein the angular positions may vary by ±0.2: 9.61, 11.49, 12.93, 15.45, and 26.05. In some embodiments, a powder X-ray diffraction pattern for the polymorph comprises characteristic peaks at the following angular positions, wherein the angular positions may vary by ±0.2: 9.61, 11.49, 12.93, 14.80, 15.45, 16.53, 23.96, 24.54, and 26.05. In some embodiments, a powder X-ray diffraction pattern for the polymorph comprises characteristic peaks at the following angular positions, wherein the angular positions may vary by ±0.2: 9.61, 11.49, 12.93, 14.80, 15.45, 16.10, 16.34, 16.53, 20.18, 22.52, 22.86, 23.96, 24.54, and 26.05. In some embodiments, a powder X-ray diffraction pattern for the polymorph comprises characteristic peaks at the following angular positions, wherein the angular positions may vary by ±0.2: 6.91, 7.72, 9.61, 11.49, 11.86, 12.93, 13.19, 13.87, 14.80, 15.45, 16.10, 16.34, 16.53, 17.14, 17.85, 19.12, 19.85, 20.18, 21.00, 22.06, 22.52, 22.86, 23.09, 23.96, 24.54, 25.26, 26.05, and 26.90. In some embodiments, including any of the foregoing embodiments, the angular positions may vary by ±0.1. In some embodiments, including any of the foregoing embodiments, the angular positions may vary by ±0.05. In some embodiments, including any of the foregoing embodiments, the angular positions may vary by ±0.02. In some embodiments, including any of the foregoing embodiments, the polymorph is isolated. In some embodiments, including any of the foregoing embodiments, the polymorph is present in a composition, wherein the composition is essentially free of Forms I-IV and -VI, wherein Forms I-IV and -VI are described in Table A or Tables 2, or 4-7 respectively. In some embodiments, including any of the foregoing embodiments, the polymorph is present in a composition, wherein at least about 95% of the composition is the polymorph, exclusive of any solvents, carriers or excipients.

In another aspect of the invention is a polymorph of a hydrate of (R)-2-hydroxy-2-methyl-4-(2,4,5-trimethyl-3,6-dioxocyclohexa-1,4-dienyl)butanamide, wherein the polymorph is Form III as described herein. In some embodiments, the polymorph has a powder x-ray diffraction pattern substantially as shown in a) or b) of FIG. 20. In some embodiments, a powder X-ray diffraction pattern for the polymorph comprises characteristic peaks at the following angular positions, wherein the angular positions may vary by ±0.2: 14.02, 15.23, and 21.10. In some embodiments, a powder X-ray diffraction pattern for the polymorph comprises characteristic peaks at least at the following angular positions, wherein the angular positions may vary by ±0.2: 14.02, 15.23, and 21.10. In some embodiments, a powder X-ray diffraction pattern for the polymorph comprises characteristic peaks at least at the following angular positions, wherein the angular positions may vary by ±0.2: 9.16, 14.02, 15.23, and 21.10. In some embodiments, a powder X-ray diffraction pattern for the polymorph comprises characteristic peaks at least at the following angular positions, wherein the angular positions may vary by ±0.2: 9.16, 13.74, 14.02, 15.23, and 21.10. In some embodiments, a powder X-ray diffraction pattern for the polymorph comprises characteristic peaks at the following angular positions, wherein the angular positions may vary by ±0.2: 9.16, 14.02, 15.23, 21.10, and 22.69. In some embodiments, a powder X-ray diffraction pattern for the polymorph comprises characteristic peaks at the following angular positions, wherein the angular positions may vary by ±0.2: 9.16, 11.81, 13.74, 14.02, 15.23, 21.10, 22.69, and 23.90. In some embodiments, a powder X-ray diffraction pattern for the polymorph comprises characteristic peaks at the following angular positions, wherein the angular positions may vary by ±0.2: 9.16, 11.81, 13.74, 14.02, 15.23, 17.35, 21.10, 22.69, 23.15, 23.90, and 26.10. In some embodiments, a powder X-ray diffraction pattern for the polymorph comprises characteristic peaks at the following angular positions, wherein the angular positions may vary by ±0.2: 9.16, 11.53, 11.81, 12.68, 12.93, 13.74, 14.02, 15.23, 16.53, 17.35, 17.98, 18.54, 19.09, 20.23, 21.10, 21.93, 22.69, 23.15, 23.50, 23.90, 24.65, 25.09, 25.46, 25.79, 26.10, 27.79, 28.22, 28.93, and 29.33. In some embodiments, including any of the foregoing embodiments, the angular positions may vary by ±0.1. In some embodiments, including any of the foregoing embodiments, the angular positions may vary by ±0.05. In some embodiments, including any of the foregoing embodiments, the angular positions may vary by ±0.02. In some embodiments, including any of the foregoing embodiments, the polymorph is isolated. In some embodiments, including any of the foregoing embodiments, the polymorph is present in a composition, wherein the composition is essentially free of Forms I, TI, IV, V, and VI, wherein Forms I, II, IV, V, and VI are described in Table A or Tables 2-3 and 5-7 respectively. In some embodiments, including any of the foregoing embodiments, the polymorph is present in a composition, wherein at least about 95% of the composition is the polymorph, exclusive of any solvents, carriers or excipients.

In another aspect of the invention is a polymorph of a solvate of (R)-2-hydroxy-2-methyl-4-(2,4,5-trimethyl-3,6-dioxocyclohexa-1,4-dienyl)butanamide, wherein the polymorph is Form II as described herein. In some embodiments, the polymorph has a powder x-ray diffraction pattern substantially as shown in a) or b) of FIG. 15. In some embodiments, a powder X-ray diffraction pattern for the polymorph comprises characteristic peaks at the following angular positions, wherein the angular positions may vary by ±0.2: 9.63, 11.33, and 19.33. In some embodiments, a powder X-ray diffraction pattern for the polymorph comprises characteristic peaks at least at the following angular positions, wherein the angular positions may vary by ±0.2: 9.63, 11.33, 19.33. In some embodiments, a powder X-ray diffraction pattern for the polymorph comprises characteristic peaks at least at the following angular positions, wherein the angular positions may vary by ±0.2: 9.63, 11.33, 10.85, and 19.33. In some embodiments, a powder X-ray diffraction pattern for the polymorph comprises characteristic peaks at least at the following angular positions, wherein the angular positions may vary by ±0.2: 9.63, 11.33, 10.85, 19.33, and 17.3. In some embodiments, a powder X-ray diffraction pattern for the polymorph comprises characteristic peaks at the following angular positions, wherein the angular positions may vary by ±0.2: 9.63, 10.85, 11.33, 13.47, and 19.33. In some embodiments, a powder X-ray diffraction pattern for the polymorph comprises characteristic peaks at the following angular positions, wherein the angular positions may vary by ±0.2: 5.76, 8.04, 9.63, 10.85, 11.33, 11.97, 13.47, 14.75, 17.37, 17.71, and 19.33. In some embodiments, a powder X-ray diffraction pattern for the polymorph comprises characteristic peaks at the following angular positions, wherein the angular positions may vary by ±0.2: 5.76, 8.04, 9.63, 10.85, 11.33, 11.97, 13.47, 14.75, 16.42, 16.89, 17.37, 17.71, 19.33, 22.89, and 24.59. In some embodiments, a powder X-ray diffraction pattern for the polymorph comprises characteristic peaks at the following angular positions, wherein the angular positions may vary by ±0.2: 5.76, 6.72, 7.57, 8.04, 9.63, 10.85, 11.33, 11.97, 12.38, 13.13, 13.47, 14.75, 15.28, 16.42, 16.89, 17.37, 17.71, 18.17, 18.66, 19.33, 20.01, 20.29, 20.67, 20.90, 21.36, 21.54, 21.80, 22.55, 22.89, 23.27, 23.54, 23.87, 24.35, 24.59, 24.87, 25.29, 25.55, 25.89, 26.44, 27.49, 28.01, 28.39, and 29.17. In some embodiments, including any of the foregoing embodiments, the angular positions may vary by ±0.1. In some embodiments, including any of the foregoing embodiments, the angular positions may vary by ±0.05. In some embodiments, including any of the foregoing embodiments, the angular positions may vary by +0.02. In some embodiments, including any of the foregoing embodiments, the polymorph is isolated. In some embodiments, including any of the foregoing embodiments, the polymorph is present in a composition, wherein the composition is essentially free of Forms I, and wherein Forms I, and III-VI are described in Table A or Tables 2-4 and 6-7 respectively. In some embodiments, including any of the foregoing embodiments, the polymorph is present in a composition, wherein at least about 95% of the composition is the polymorph, exclusive of any solvents, carriers or excipients. 100391 In another aspect of the invention is a polymorph of a solvate of (R)-2-hydroxy-2-methyl-4-(2,4,5-trimethyl-3,6-dioxocyclohexa-1,4-dienyl)butanamide, wherein the polymorph is Form IV as described herein. In some embodiments, the polymorph has a powder x-ray diffraction pattern substantially as shown in a), b), or c) of FIG. 25. In some embodiments, a powder X-ray diffraction pattern for the polymorph comprises characteristic peaks at the following angular positions, wherein the angular positions may vary by ±0.2: 4.31, 12.97, and 13.20. In some embodiments, a powder X-ray diffraction pattern for the polymorph comprises characteristic peaks at least at the following angular positions, wherein the angular positions may vary by ±0.2: 4.31, 12.97, 13.20. In some embodiments, a powder X-ray diffraction pattern for the polymorph comprises characteristic peaks at least at the following angular positions, wherein the angular positions may vary by ±0.2: 4.31, 8.76, 12.97, and 13.20. In some embodiments, a powder X-ray diffraction pattern for the polymorph comprises characteristic peaks at least at the following angular positions, wherein the angular positions may vary by ±0.2: 0.2: 4.31, 8.76, 12.97, 13.20, 16.66. In some embodiments, a powder X-ray diffraction pattern for the polymorph comprises characteristic peaks at the following angular positions, wherein the angular positions may vary by ±0.2: 4.31, 8.76, 12.97, 13.20, and 16.66. In some embodiments, a powder X-ray diffraction pattern for the polymorph comprises characteristic peaks at the following angular positions, wherein the angular positions may vary by ±0.2: 4.31, 7.94, 8.76, 12.97, 13.20, 16.66, 17.33, and 20.57. In some embodiments, a powder X-ray diffraction pattern for the polymorph comprises characteristic peaks at the following angular positions, wherein the angular positions may vary by ±0.2: 4.31, 7.94, 8.76, 12.97, 13.20, 15.08, 16.66, 17.33, 19.09, 20.57, and 21.58. In some embodiments, a powder X-ray diffraction pattern for the polymorph comprises characteristic peaks at the following angular positions, wherein the angular positions may vary by ±0.2: 4.31, 5.77, 6.28, 7.53, 7.94, 8.76, 9.39, 9.87, 10.54, 11.07, 11.68, 12.02, 12.28, 12.97, 13.20, 13.52, 14.40, 15.08, 15.90, 16.66, 16.96, 17.33, 17.59, 18.77, 19.09, 19.74, 20.27, 20.57, 21.09, 21.58, 22.81, 23.23, 24.01, 24.65, and 25.60. In some embodiments, including any of the foregoing embodiments, the angular positions may vary by ±0.1. In some embodiments, including any of the foregoing embodiments, the angular positions may vary by ±0.05. In some embodiments, including any of the foregoing embodiments, the angular positions may vary by ±0.02. In some embodiments, including any of the foregoing embodiments, the polymorph is isolated. In some embodiments, including any of the foregoing embodiments, the polymorph is present in a composition, wherein the composition is essentially free of Forms I-III and V-VI, wherein Forms I-III and V-VI are described in Table A or Tables 2-5 and 7 respectively. In some embodiments, including any of the foregoing embodiments, the polymorph is present in a composition, wherein at least about 95% of the composition is the polymorph, exclusive of any solvents, carriers or excipients.

In another aspect of the invention is a polymorph of a solvate of (R)-2-hydroxy-2-methyl-4-(2,4,5-trimethyl-3,6-dioxocyclohexa-1,4-dienyl)butanamide, wherein the polymorph is Form VI as described herein. In some embodiments, the polymorph has a powder x-ray diffraction pattern substantially as shown in a) of FIG. 33. In some embodiments, a powder X-ray diffraction pattern for the polymorph comprises characteristic peaks at the following angular positions, wherein the angular positions may vary by ±0.2: 6.27, 9.91, and 12.94. In some embodiments, a powder X-ray diffraction pattern for the polymorph comprises characteristic peaks at least at the following angular positions, wherein the angular positions may vary by ±0.2: 6.27, 9.91, and 12.94. In some embodiments, a powder X-ray diffraction pattern for the polymorph comprises characteristic peaks at least at the following angular positions, wherein the angular positions may vary by ±0.2: 6.27, 9.91, 12.94, and 15.71. In some embodiments, a powder X-ray diffraction pattern for the polymorph comprises characteristic peaks at least at the following angular positions, wherein the angular positions may vary by ±0.2: 6.27, 9.91, 12.94, 15.71, and 19.13. In some embodiments, a powder X-ray diffraction pattern for the polymorph comprises characteristic peaks at the following angular positions, wherein the angular positions may vary by ±0.2: 6.27, 9.41, 9.91, 12.94, and 13.29. In some embodiments, a powder X-ray diffraction pattern for the polymorph comprises characteristic peaks at the following angular positions, wherein the angular positions may vary by ±0.2: 6.27, 8.85, 9.41, 9.91, 12.94, 13.29, 16.67, and 19.13. In some embodiments, a powder X-ray diffraction pattern for the polymorph comprises characteristic peaks at the following angular positions, wherein the angular positions may vary by ±0.2: 4.39, 6.27, 8.85, 9.41, 9.91, 11.32, 12.94, 13.29, 14.03, 16.67, 19.13, 20.76, and 22.06. In some embodiments, a powder X-ray diffraction pattern for the polymorph comprises characteristic peaks at the following angular positions, wherein the angular positions may vary by ±0.2: 4.39, 6.27, 7.00, 8.62, 8.85, 9.41, 9.91, 11.32, 11.50, 12.25, 12.56, 12.94, 13.29, 14.03, 14.82, 15.10, 15.44, 15.71, 16.01, 16.67, 16.91, 17.33, 17.59, 18.33, 18.75, 19.13, 20.25, 20.76, 21.68, 22.06, 22.27, 22.61, 22.94, 24.01, 24.33, 24.65, 25.48, 26.05, 28.63, and 29.18. In some embodiments, including any of the foregoing embodiments, the angular positions may vary by ±0.1. In some embodiments, including any of the foregoing embodiments, the angular positions may vary by ±0.05. In some embodiments, including any of the foregoing embodiments, the angular positions may vary by ±0.02. In some embodiments, including any of the foregoing embodiments, the polymorph is isolated. In some embodiments, including any of the foregoing embodiments, the polymorph is present in a composition, wherein the composition is essentially free of Forms I-V, wherein Forms I-V are described in Table A or Tables 2-6 respectively. In some embodiments, including any of the foregoing embodiments, the polymorph is present in a composition, wherein at least about 95% of the composition is the polymorph, exclusive of any solvents, carriers or excipients.

In another aspect of the invention is a composition comprising amorphous (R)-2-hydroxy-2-methyl-4-(2,4,5-trimethyl-3,6-dioxocyclohexa-1,4-dienyl)butanamide. In some embodiments, the amorphous form is isolated. In some embodiments, the composition is essentially free of Forms I-VI, wherein Forms I-VI are described in Table A or Tables 2-7 respectively. In some embodiments, including any of the foregoing embodiments, at least about 95% of the composition is amorphous (R)-2-hydroxy-2-methyl-4-(2,4,5-trimethyl-3,6-dioxocyclohexa-1,4-dienyl)butanamide, exclusive of any solvents, carriers or excipients.

In another aspect of the invention is a pharmaceutical composition comprising a polymorphic or amorphous form of an anhydrate, a hydrate, or a solvate of (R)-2-hydroxy-2-methyl-4-(2,4,5-trimethyl-3,6-dioxocyclohexa-1,4-dienyl)butanamide, or composition comprising such form, as described herein, including any of the foregoing or hereafter embodiments, and a pharmaceutically acceptable carrier. In some embodiments, the form is polymorph Form I. In some embodiments, the form is polymorph Form II. In some embodiments, the form is polymorph Form III. In some embodiments, the form is polymorph Form IV. In some embodiments, the form is polymorph Form V. In some embodiments, the form is polymorph Form VI. In some embodiments, the form is amorphous. In some embodiments, the pharmaceutical composition has an HPLC purity of more than about 95% for the anhydrate, hydrate, or solvate of (R)-2-hydroxy-2-methyl-4-(2,4,5-trimethyl-3,6-dioxocyclohexa-1,4-dienyl)butanamide, exclusive of any solvents, carriers or excipients. In some embodiments, the pharmaceutical composition has an HPLC purity of more than about 99% for the anhydrate, hydrate, or solvate of (R)-2-hydroxy-2-methyl-4-(2,4,5-trimethyl-3,6-dioxocyclohexa-1,4-dienyl)butanamide, exclusive of any solvents, carriers or excipients. In some embodiments, the pharmaceutical composition has an HPLC purity of more than about 99.9% for the anhydrate, hydrate, or solvate of (R)-2-hydroxy-2-methyl-4-(2,4,5-trimethyl-3,6-dioxocyclohexa-1,4-dienyl)butanamide, exclusive of any solvents, carriers or excipients. HPLC purity % refers to the proportional area of a given compound's HPLC peak with respect to the area of all peaks in a given HPLC spectrum. HPLC % is calculated by dividing the area of a compound peak by the area of all peaks, in a HPLC spectrum, and multiplying this quotient by one-hundred.

In another aspect of the invention is a pharmaceutical composition comprising an active agent and a pharmaceutically acceptable carrier, wherein the active agent consists of, or consists essentially of, a polymorphic or amorphous form of an anhydrate, a hydrate, or a solvate of (R)-2-hydroxy-2-methyl-4-(2,4,5-trimethyl-3,6-dioxocyclohexa-1,4-dienyl)butanamide as described herein. In some embodiments, the form is polymorph Form I. In some embodiments, the form is polymorph Form II. In some embodiments, the form is polymorph Form III. In some embodiments, the form is polymorph Form IV. In some embodiments, the form is polymorph Form V. In some embodiments, the form is polymorph Form VI. In some embodiments, the form is amorphous.

In another aspect of the invention is a method of treating or suppressing an oxidative stress disorder, modulating one or more energy biomarkers, normalizing one or more energy biomarkers, or enhancing one or more energy biomarkers, comprising administering to an individual in need thereof a therapeutically effective amount or effective amount of a polymorphic or amorphous form of an anhydrate, a hydrate, or a solvate of (R)-2-hydroxy-2-methyl-4-(2,4,5-trimethyl-3,6-dioxocyclohexa-1,4-dienyl)butanamide, or composition comprising such form, as described herein, including any of the foregoing or hereafter embodiments. The method can use any individual polymorphic or amorphous form of the invention as described herein, or a combination of such. In some embodiments, the form is polymorph Form I. In some embodiments, the form is polymorph Form II. In some embodiments, the form is polymorph Form III. In some embodiments, the form is polymorph Form IV. In some embodiments, the form is polymorph Form V. In some embodiments, the form is polymorph Form VI. In some embodiments, the form is amorphous. In some embodiments, including any of the foregoing embodiments, the anhydrate, hydrate, or solvate of (R)-2-hydroxy-2-methyl-4-(2,4,5-trimethyl-3,6-dioxocyclohexa-1,4-dienyl)butanamide is administered in a pharmaceutical composition comprising the polymorphic or amorphous form and a pharmaceutically acceptable carrier. In some embodiments, including any of the foregoing embodiments, the pharmaceutical composition comprises an active agent consisting essentially of the polymorphic or amorphous form of the anhydrate, hydrate, or solvate of (R)-2-hydroxy-2-methyl-4-(2,4,5-trimethyl-3,6-dioxocyclohexa-1,4-dienyl)butanamide. In some embodiments, including any of the foregoing embodiments, the method is a method of treating or suppressing an oxidative stress disorder. In some embodiments, including any of the foregoing embodiments, the method is a method of treating an oxidative stress disorder. In some embodiments, including any of the foregoing embodiments, the method is a method of suppressing an oxidative stress disorder. In some embodiments, including any of the foregoing embodiments, the oxidative stress disorder is selected from the group consisting of: a mitochondrial disorder; an inherited mitochondrial disease; Alpers Disease; Barth syndrome; a Beta-oxidation Defect; Carnitine-Acyl-Carnitine Deficiency; Carnitine Deficiency; a Creatine Deficiency Syndrome; Co-Enzyme Q10 Deficiency; Complex I Deficiency; Complex II Deficiency; Complex III Deficiency; Complex IV Deficiency; Complex V Deficiency; COX Deficiency; chronic progressive external ophthalmoplegia (CPEO); CPT I Deficiency; CPT II Deficiency; Friedreich's Ataxia (FA); Glutaric Aciduria Type II; Kearns-Sayre Syndrome (KSS); Lactic Acidosis; Long-Chain Acyl-CoA Dehydrogenase Deficiency (LCAD); LCHAD; Leigh's syndrome; Leigh-like Syndrome; Leber's Hereditary Optic Neuropathy (LHON); Lethal Infantile Cardiomyopathy (LIC); Luft Disease; Multiple Acyl-CoA Dehydrogenase Deficiency (MAD); Medium-Chain Acyl-CoA Dehydrogenase Deficiency (MCAD); Mitochondrial Myopathy, Encephalopathy, Lactacidosis, Stroke (MELAS); Myoclonic Epilepsy with Ragged Red Fibers (MERRF); Mitochondrial Recessive Ataxia Syndrome (MIRAS); Mitochondrial Cytopathy, Mitochondrial DNA Depletion; Mitochondrial Encephalopathy; Mitochondrial Myopathy; Myoneurogastrointestina Disorder and Encephalopathy (MNGIE); Neuropathy, Ataxia, and Retinitis Pigmentosa (NARP); Pearson Syndrome; Pyruvate Carboxylase Deficiency; Pyruvate Dehydrogenase Deficiency; a POLG Mutation; a Respiratory Chain Disorder; Short-Chain Acyl-CoA Dehydrogenase Deficiency (SCAD); SCHAD; Very Long-Chain Acyl-CoA Dehydrogenase Deficiency (VLCAD); a myopathy; cardiomyopathy; encephalomyopathy; a neurodegenerative disease; Parkinson's disease; Alzheimer's disease; amyotrophic lateral sclerosis (ALS); a motor neuron disease; a neurological disease; epilepsy; an age-associated disease; macular degeneration; diabetes; metabolic syndrome; cancer; brain cancer; a genetic disease; Huntington's Disease; a mood disorder; schizophrenia; bipolar disorder; a pervasive developmental disorder; autistic disorder; Asperger's syndrome; childhood disintegrative disorder (CDD); Rett's disorder; PDD—not otherwise specified (PDD-NOS); a cerebrovascular accident; stroke; a vision impairment; optic neuropathy; dominant inherited juvenile optic atrophy; optic neuropathy caused by a toxic agent; glaucoma; Stargardt's macular dystrophy; diabetic retinopathy; diabetic maculopathy; retinopathy of prematurity; ischemic reperfusion-related retinal injury; oxygen poisoning; a haemoglobinopathy; thalassemia; sickle cell anemia; seizures; ischemia; renal tubular acidosis; attention deficit/hyperactivity disorder (ADHD); a neurodegenerative disorder resulting in hearing or balance impairment; Dominant Optic Atrophy (DOA); Maternally inherited diabetes and deafness (MIDD); chronic fatigue; contrast-induced kidney damage; contrast-induced retinopathy damage; Abetalipoproteinemia; retinitis pigmentosum; Wolfram's disease; Tourette syndrome; cobalamin c defect; methylmalonic aciduria; glioblastoma; Down's syndrome; acute tubular necrosis; a muscular dystrophy; a leukodystrophy; Progressive Supranuclear Palsy; spinal muscular atrophy; hearing loss; noise induced hearing loss; traumatic brain injury; Juvenile Huntington's Disease; Multiple Sclerosis; NGLY1; Multiple System Atrophy; Adrenoleukodystrophy; and Adrenomyeloneuropathy. In some embodiments, the oxidative stress disorder is Multiple System Atrophy. In some embodiments, including any of the foregoing embodiments, the oxidative stress disorder is cancer. In some embodiments, including any of the foregoing embodiments, the oxidative stress disorder is bipolar disorder. In some embodiments, the oxidative stress disorder is schizophrenia. In some embodiments, including any of the foregoing embodiments, the oxidative stress disorder is an age-associated disease. In some embodiments, including any of the foregoing embodiments, the oxidative stress disorder is Huntington's Disease. In some embodiments, including any of the foregoing embodiments, the oxidative stress disorder is Alzheimer's disease. In some embodiments, including any of the foregoing embodiments, the oxidative stress disorder is amyotrophic lateral sclerosis (ALS). In some embodiments, including any of the foregoing embodiments, the oxidative stress disorder is epilepsy. In some embodiments, including any of the foregoing embodiments, the oxidative stress disorder is Parkinson's disease. In some embodiments, including any of the foregoing embodiments, the oxidative stress disorder is seizures. In some embodiments, including any of the foregoing embodiments, the oxidative stress disorder is stroke. In some embodiments, including any of the foregoing embodiments, the oxidative stress disorder is a mitochondrial disorder. In some embodiments, including any of the foregoing embodiments, the oxidative stress disorder is an inherited mitochondrial disease. In some embodiments, including any of the foregoing embodiments, the oxidative stress disorder is Friedreich's Ataxia (FA). In some embodiments, including any of the foregoing embodiments, the oxidative stress disorder is Kearns-Sayre Syndrome (KSS). In some embodiments, including any of the foregoing embodiments, the oxidative stress disorder is Leigh Syndrome or Leigh-like Syndrome. In some embodiments, including any of the foregoing embodiments, the oxidative stress disorder is Leber's Hereditary Optic Neuropathy (LHON). In some embodiments, including any of the foregoing embodiments, the oxidative stress disorder is Mitochondrial Myopathy, Encephalopathy, Lactacidosis, Stroke (MELAS). In some embodiments, including any of the foregoing embodiments, the oxidative stress disorder is Myoclonic Epilepsy with Ragged Red Fibers (MERRF). In some embodiments, including any of the foregoing embodiments, the oxidative stress disorder is macular degeneration. In some embodiments, including any of the foregoing embodiments, the oxidative stress disorder is brain cancer. In some embodiments, including any of the foregoing embodiments, the oxidative stress disorder is autistic disorder. In some embodiments, including any of the foregoing embodiments, the oxidative stress disorder is Rett's disorder. In some embodiments, including any of the foregoing embodiments, the oxidative stress disorder is Maternally inherited diabetes and deafness (MIDD). In some embodiments, including any of the foregoing embodiments, the oxidative stress disorder is chronic fatigue. In some embodiments, including any of the foregoing embodiments, the oxidative stress disorder is contrast-induced kidney damage. In some embodiments, including any of the foregoing embodiments, the oxidative stress disorder is contrast-induced retinopathy damage. In some embodiments, including any of the foregoing embodiments, the oxidative stress disorder is cobalamin c defect. In some embodiments, including any of the foregoing embodiments, the method is a method for modulating one or more energy biomarkers, normalizing one or more energy biomarkers, or enhancing one or more energy biomarkers, wherein the one or more energy biomarkers are selected from the group consisting of: lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; total, reduced or oxidized glutathione levels, or reduced/oxidized glutathione ratio either in whole blood, plasma, lymphocytes, cerebrospinal fluid, or cerebral ventricular fluid; total, reduced or oxidized cysteine levels, or reduced/oxidized cysteine ratio either in whole blood, plasma, lymphocytes, cerebrospinal fluid, or cerebral ventricular fluid; phosphocreatine levels, NADH (NADH+ H+) levels; NADPH (NADPH+H+) levels; NAD levels; NADP levels; ATP levels; reduced coenzyme Q ($CoQ_{red}$) levels; oxidized coenzyme Q ($CoQ_{ox}$) levels; total coenzyme Q ($CoQ_{tot}$) levels; oxidized cytochrome C levels; reduced cytochrome C levels; oxidized cytochrome C/reduced cytochrome C ratio; acetoacetate levels, r3 hydroxy butyrate levels, acetoacetate/I3 hydroxy butyrate ratio, 8-hydroxy-2'-deoxyguanosine (8-OHdG) levels; levels of reactive oxygen species; levels of oxygen consumption (VO2); levels of carbon dioxide output (VCO2); respiratory quotient (VCO2/VO2); exercise tolerance; and anaerobic threshold. Energy biomarkers can be measured in whole blood, plasma, cerebrospinal fluid, cerebroventricular fluid, arterial blood, venous blood, or any other body fluid, body gas, or other biological sample useful for such measurement. In some embodiments, including any of the foregoing embodiments, the levels are modulated to a value within about 2 standard deviations of the value in a healthy subject. In some embodiments, including any of the foregoing embodiments, the levels are modulated to a value within about 1 standard deviation of the value in a healthy subject. In some embodiments, including any of the foregoing embodiments, the levels in a subject are changed by at least about 10% above or below the level in the subject prior to modulation. In some embodiments, including any of the foregoing embodiments, the levels are changed by at least about 20% above or below the level in the subject prior to modulation. In some embodiments, including any of the foregoing embodiments, the levels are changed by at least about 30% above or below the level in the subject prior to modulation. In some embodiments, including any of the foregoing embodiments, the levels are changed by at least about 40% above or below the level in the subject prior to modulation. In some embodiments, including any of the foregoing embodiments, the levels are changed by at least about 50% above or below the level in the subject prior to modulation. In some embodiments, including any of the foregoing embodiments, the levels are changed by at least about 75% above or below the level in the subject prior to modulation. In some embodiments, including any of the foregoing embodiments, the levels are changed by at least about 100% above or at least about 90% below the level in the subject prior to modulation. In some embodiments, including any of the foregoing embodiments, the subject or subjects in which a method of treating or suppressing an oxidative stress disorder, modulating one or more energy biomarkers, normalizing one or more energy biomarkers, or enhancing one or more energy biomarkers is performed is/are selected from the group consisting of subjects undergoing strenuous or prolonged physical activity; subjects with chronic energy problems; subjects with chronic respiratory problems; pregnant females; pregnant females in labor; neonates; premature neonates; subjects exposed to extreme environments; subjects exposed to hot environments; subjects exposed to cold environments; subjects exposed to environments with lower-than-average oxygen content; subjects exposed to environments with higher-than-average carbon dioxide content; subjects exposed to environments with higher-than-average levels of air pollution; airline travelers; flight attendants; subjects at elevated altitudes; subjects living in cities with lower-than-average air quality; subjects working in enclosed environments where air quality is degraded; subjects with lung diseases; subjects with lower-than-average lung capacity; tubercular patients; lung cancer patients; emphysema patients; cystic fibrosis patients; subjects recovering from surgery; subjects recovering from illness; elderly subjects; elderly subjects experiencing decreased energy; subjects suffering from chronic fatigue; subjects suffering from chronic fatigue syndrome; subjects undergoing acute trauma; subjects in shock; subjects requiring acute oxygen administration; subjects requiring chronic oxygen administration; subjects requiring organ visualization via contrast solution; or other subjects with acute, chronic, or ongoing energy demands who can benefit from enhancement of energy biomarkers.

In another aspect of the invention is the use of a polymorphic or amorphous form of an anhydrate, a hydrate, or a solvate of (R)-2-hydroxy-2-methyl-4-(2,4,5-trimethyl-3,6-dioxocyclohexa-1,4-dienyl)butanamide as described herein, including any of the foregoing or hereafter described embodiments, for treating or suppressing an oxidative stress disorder. In some embodiments, the form is polymorph Form I. In some embodiments, the form is polymorph Form II. In some embodiments, the form is polymorph Form III. In some embodiments, the form is polymorph Form IV. In some embodiments, the form is polymorph Form V. In some embodiments, the form is polymorph Form VI. In some embodiments, the form is amorphous. In another aspect of the invention is the use of a polymorphic or amorphous form of an anhydrate, a hydrate, or a solvate of (R)-2-hydroxy-2-methyl-4-(2,4,5-trimethyl-3,6-dioxocyclohexa-1,4-dienyl)butanamide as described herein, including any of the foregoing or hereafter described embodiments, in the manufacture of a medicament for use in treating or suppressing an oxidative stress disorder. In some embodiments, the form is polymorph Form I. In some embodiments, the form is polymorph Form II. In some embodiments, the form is polymorph Form III. In some embodiments, the form is polymorph Form IV. In some embodiments, the form is polymorph Form V. In some embodiments, the form is polymorph Form VI. In some embodiments, the form is amorphous.

For all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as 'consisting essentially of' a component, the composition may additionally contain any amount of pharmaceutically acceptable carriers, vehicles, or diluents and other such components which do not substantially affect the condition being treated.

In another aspect of the invention is a process for the preparation of polymorph Form I of an anhydrate of (R)-2-hydroxy-2-methyl-4-(2,4,5-trimethyl-3,6-dioxocyclohexa-1,4-dienyl)butanamide, wherein the process comprises the steps: (a) contacting (R)-2-hydroxy-2-methyl-4-(2,4,5-trimethyl-3,6-dioxocyclohexa-1,4-dienyl)butanamide with a liquid comprising WA; and (b) removing the liquid. In some embodiments, step (a) comprises dissolving the (R)-2-hydroxy-2-methyl-4-(2,4,5-trimethyl-3,6-dioxocyclohexa-1,4-dienyl)butanamide in the liquid. In some embodiments, step (a) comprises slurrying the (R)-2-hydroxy-2-methyl-4-(2,4,5-trimethyl-3,6-dioxocyclohexa-1,4-dienyl)butanamide in the liquid. In some embodiments, the slurrying in step (a) may be performed for at least about 24 hours. In some embodiments, including any of the foregoing embodiments, the liquid is 100% IPA In some embodiments, including any of the foregoing embodiments, the liquid is 98% IPA/2% water (v/v). In some embodiments, including any of the foregoing embodiments, the process further comprises step (a)(i): adding heptane to the liquid. In some embodiments, including any of the foregoing embodiments, step (b) comprises filtering the (R)-2-hydroxy-2-methyl-4-(2,4,5-trimethyl-3,6-dioxocyclohexa-1,4-dienyl)butanamide. In some embodiments, including any of the foregoing embodiments, the mixture in step (a) or step (a)(i) may be seeded with Form I crystals. In some embodiments, including any of the foregoing embodiments, the (R)-2-hydroxy-2-methyl-4-(2,4,5-trimethyl-3,6-dioxocyclohexa-1,4-dienyl)butanamide in step (a) is at least about 95% pure. In various embodiments, including any of the foregoing embodiments, the (R)-2-hydroxy-2-methyl-4-(2,4,5-trimethyl-3,6-dioxocyclohexa-1,4-dienyl)butanamide in step (a) is at least about 96%, at least about 97%, at least about 98%, at least about 99%, at least about 99.5%, at least about 99.9% pure. In another aspect of the invention is an anhydrate of (R)-2-hydroxy-2-methyl-4-(2,4,5-trimethyl-3,6-dioxocyclohexa-1,4-dienyl)butanamide prepared by the above described process.

In another aspect of the invention is a process for the preparation of polymorph Form II of an anhydrate of (R)-2-hydroxy-2-methyl-4-(2,4,5-trimethyl-3,6-dioxocyclohexa-1,4-dienyl)butanamide, wherein the process comprises the steps: (a) dissolving the (R)-2-hydroxy-2-methyl-4-(2,4,5-trimethyl-3,6-dioxocyclohexa-1,4-dienyl)butanamide in EtOAc, (b) rapidly cooling the mixture from (a), and (c) isolating the (R)-2-hydroxy-2-methyl-4-(2,4,5-trimethyl-3,6-dioxocyclohexa-1,4-dienyl)butan am i de In some embodiments, the initial (R)-2-hydroxy-2-methyl-4-(2,4,5-trimethyl-3,6-dioxocyclohexa-1,4-dienyl)butanamide is Form I In some embodiments, including any of the foregoing embodiments, step (a) is at about 60° C. In some embodiments, including any of the foregoing embodiments, step (b) comprises rapidly cooling the mixture in an ice bath. In some embodiments, including any of the foregoing embodiments, the mixture in step (b) may be seeded with Form II crystals. In another aspect of the invention is an anhydrate of (R)-2-hydroxy-2-methyl-4-(2,4,5-trimethyl-3,6-dioxocyclohexa-1,4-dienyl)butanamide prepared by the above described process.

In another aspect of the invention is a process for the preparation of polymorph Form III of a solvate of (R)-2-hydroxy-2-methyl-4-(2,4,5-trimethyl-3,6-dioxocyclohexa-1,4-dienyl)butanamide, wherein the process comprises the steps: (a) combining (R)-2-hydroxy-2-methyl-4-(2,4,5-trimethyl-3,6-dioxocyclohexa-1,4-dienyl)butanamide and 0.5% MC/2% Tween 80 in water to create a slurry; (b) slurrying the mixture from (a), and (c) removing the 0.5% MC/2% Tween 80 in water. As used herein "MC" refers to methyl cellulose and "Tween 80" refers to a commercially available polysorbate nonionic surfactant In some embodiments, the initial (R)-2-hydroxy-2-methyl-4-(2,4,5-trimethyl-3,6-dioxocyclohexa-1,4-dienyl)butanamide is Form I. In some embodiments, including any of the foregoing embodiments, step (b) is performed for at least about 24 hours. In some embodiments, including any of the foregoing embodiments, step (b) is at room temperature. In some embodiments, including any of the foregoing embodiments, the mixture in step (b) may be seeded with Form III crystals. In another aspect of the invention is a solvate of (R)-2-hydroxy-2-methyl-4-(2,4,5-trimethyl-3,6-dioxocyclohexa-1,4-dienyl)butanamide prepared by the above described process.

In another aspect of the invention is a process for the preparation of polymorph Form III of a solvate of (R)-2-hydroxy-2-methyl-4-(2,4,5-trimethyl-3,6-dioxocyclohexa-1,4-dienyl)butanamide, wherein the process comprises the steps: (a) combining (R)-2-hydroxy-2-methyl-4-(2,4,5-trimethyl-3,6-dioxocyclohexa-1,4-dienyl)butanamide and 0.5% MC in water to create a slurry; (b) slurrying the mixture from (a), and (c) removing the 0.5% MC in water. In some embodiments, the initial (R)-2-hydroxy-2-methyl-4-(2,4,5-trimethyl-3,6-dioxocyclohexa-1,4-dienyl)butanamide is Form I, II, IV, V or VI. In some embodiments, including any of the foregoing embodiments, step (b) is performed at room temperature. In some embodiments, including any of the foregoing embodiments, step (b) may be performed for at least about 7 days. In some embodiments, including any of the foregoing embodiments, the mixture in step (b) may be seeded with Form III crystals. In another aspect of the invention is a solvate of (R)-2-hydroxy-2-methyl-4-(2,4,5- trimethyl-3,6-dioxocyclohexa-1,4-dienyl)butanamide prepared by the above described process.

DETAILED DESCRIPTION

Figure 1:
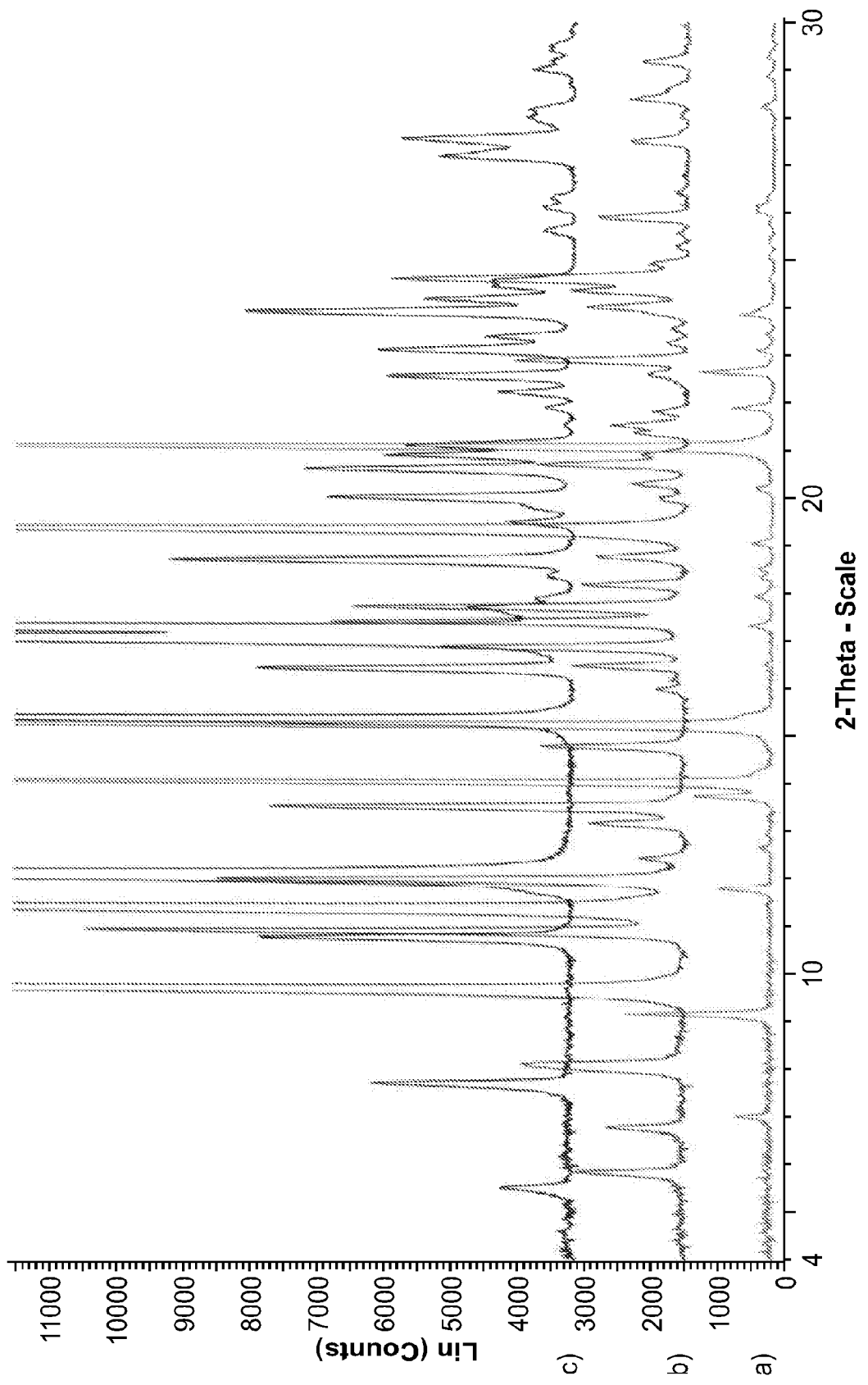
FIG. 1 shows a XRPD stack plot of (R)-2-hydroxy-2-methyl-4-(2,4,5-trimethyl-3,6-dioxocyclohexa-1,4-dienyl)butanamide short term slurry experiments, a) Pattern C, from slurry in 0.5% Methyl Cellulose/2% Tween 80, b) Pattern B, from slurry in tetrahydrofuran (THF), and c) starting material, Pattern A.

The invention embraces polymorphic and amorphous forms of anhydrates, hydrates, and solvates of (R)-2-hydroxy-2-methyl-4-(2,4,5-trimethyl-3,6-dioxocyclohexa-1,4-dienyl)butanamide useful in treating or suppressing diseases, developmental delays and symptoms related to oxidative stress such as mitochondrial disorders, impaired energy processing disorders, neurodegenerative diseases and diseases of aging, and methods of using such compositions for treating or suppressing an oxidative stress disorder, or for modulating, normalizing, or enhancing one or more (e.g. one, two, three, or more) energy biomarkers. The invention further embraces methods for producing such polymorphic and amorphous forms.

The abbreviations used herein have their conventional meaning within the chemical and biological arts, unless otherwise specified.

Reference to "about" a value or parameter herein includes (and describes) variations that are directed to that value or parameter per se. For example, description referring to "about X" includes description of "X".

The terms "a" or "an," as used in herein means one or more, unless context clearly dictates otherwise.

By "subject," "individual," or "patient" is meant an individual organism, preferably a vertebrate, more preferably a mammal, most preferably a human.

(R)-2-hydroxy-2-methyl-4-(2,4,5-trimethyl-3,6-dioxocyclohexa-1,4-dienyl)butanamide may exist in anhydrate, hydrate, and solvate forms. Unless otherwise specified or clear from context, as used herein the term "(R)-2-hydroxy-2-methyl-4-(2,4,5-trimethyl-3,6-dioxocyclohexa-1,4-dienyl)butanamide" encompasses anhydrate, hydrate, and solvate forms of the compound.

The term "substantially as shown in" when referring, for example, to an XRPD pattern, a DSC thermogram, or a TGA graph includes a pattern, thermogram or graph that is not necessarily identical to those depicted herein, but that falls within the limits of experimental error or deviations when considered by one of ordinary skill in the art. For example, in an XRPD pattern, the relative intensity of the peaks in the diffraction pattern can vary, e.g. due to sample preparation conditions. In addition, changes in temperature (when generating the XRPD data) can affect the shape and location of peaks. The XRPD patterns given herein were generated at room temperature (~25° C.). In some embodiments, the XRPD pattern is generated at about 15° C. to about 30° C. In some embodiments, the XRPD pattern is generated at about 20° C. to about 30° C. In some embodiments, the XRPD pattern is generated at about 23° C. to about 27° C. In some embodiments, the XRPD pattern is generated at about 24° C. to about 26° C. In some embodiments, the XRPD pattern is generated at about 25° C.

Similarly, when describing a polymorph by characteristic peaks (e.g. angular positions of the peaks), it is to be understood that the location of the peaks may vary depending on sample preparation, temperature, etc. The characteristic XRPD peaks given herein were generated at room temperature (~25° C.). In some embodiments, the XRPD data is generated at about 15° C. to about 30° C. In some embodiments, the XRPD data is generated at about 20° C. to about 30° C. In some embodiments, the XRPD data is generated at about 23° C. to about 27° C. In some embodiments, the XRPD data is generated at about 24° C. to about 26° C. In some embodiments, the XRPD data is generated at about 25° C.

A polymorph or amorphous form that is "isolated" is used herein to refer to a form that is at least 90% that particular form (i.e. less than 10% of the material is comprises of other forms or other compounds, including but not limited to (S)-2-hydroxy-2-methyl-4-(2,4,5-trimethyl-3,6-dioxocyclohexa-1,4-dienyl)butanamide.

A polymorph composition that is "essentially free of" a particular component(s) indicates that the composition contains less than about 5% of the particular component(s). As a non-limiting example, a polymorph composition that is essentially free of polymorph Form II indicates a composition that contains less than about 5% of Form II. In some embodiments, "essentially free of" indicates that the composition contains less than about 4%, less than about 3%, less than about 2%, or less than about 1% of the particular component(s), or wherein the particular component(s) are not present within the limit of detection.

"Angular positions" indicates Angle, 2 theta.

"Treating" a disorder with the compounds, compositions, and methods discussed herein is defined as administering one or more of the compounds or compositions discussed herein, with or without additional therapeutic agents, in order to reduce or eliminate either the disorder or one or more symptoms of the disorder, or to retard the progression of the disorder or of one or more symptoms of the disorder, or to reduce the severity of the disorder or of one or more symptoms of the disorder. "Suppression" of a disorder with the compounds, compositions, and methods discussed herein is defined as administering one or more of the compounds or compositions discussed herein, with or without additional therapeutic agents, in order to suppress the clinical manifestation of the disorder, or to suppress the manifestation of adverse symptoms of the disorder. The distinction between treatment and suppression is that treatment occurs after adverse symptoms of the disorder are manifest in a subject, while suppression occurs before adverse symptoms of the disorder are manifest in a subject. Suppression may be partial, substantially total, or total. Because some of the disorders are inherited, genetic screening can be used to identify patients at risk of the disorder. The compounds, compositions, and methods of the invention can then be administered to asymptomatic patients at risk of developing the clinical symptoms of the disorder, in order to suppress the appearance of any adverse symptoms.

"Therapeutic use" of the compounds and compositions discussed herein is defined as using one or more of the compounds or compositions discussed herein to treat or suppress a disorder, as defined above. An "effective amount" of a compound or composition is an amount of the compound or composition sufficient to modulate, normalize, or enhance one or more energy biomarkers (where modulation, normalization, and enhancement are defined below). A "therapeutically effective amount" of a compound or composition is an amount of the compound or composition, which, when administered to a subject, is sufficient to reduce or eliminate either a disorder or one or more symptoms of a disorder, or to retard the progression of a disorder or of one or more symptoms of a disorder, or to reduce the severity of a disorder or of one or more symptoms of a disorder, or to suppress the clinical manifestation of a disorder, or to suppress the manifestation of adverse symptoms of a disorder. A therapeutically effective amount can be given in one or more administrations. An "effective amount" of a compound or composition embraces both a therapeutically effective amount, as well as an amount effective to modulate, normalize, or enhance one or more energy biomarkers in a subject.

"Modulation" of, or to "modulate," an energy biomarker means to change the level of the energy biomarker towards a desired value, or to change the level of the energy biomarker in a desired direction (e.g., increase or decrease). Modulation can include, but is not limited to, normalization and enhancement as defined below.

"Normalization" of, or to "normalize," an energy biomarker is defined as changing the level of the energy biomarker from a pathological value towards a normal value, where the normal value of the energy biomarker can be 1) the level of the energy biomarker in a healthy person or subject, or 2) a level of the energy biomarker that alleviates one or more undesirable symptoms in the person or subject. That is, to normalize an energy biomarker which is depressed in a disease state means to increase the level of the energy biomarker towards the normal (healthy) value or towards a value which alleviates an undesirable symptom; to normalize an energy biomarker which is elevated in a disease state means to decrease the level of the energy biomarker towards the normal (healthy) value or towards a value which alleviates an undesirable symptom.

"Enhancement" of, or to "enhance," energy biomarkers means to intentionally change the level of one or more energy biomarkers away from either the normal value, or the value before enhancement, in order to achieve a beneficial or desired effect. For example, in a situation where significant energy demands are placed on a subject, it may be desirable to increase the level of ATP in that subject to a level above the normal level of ATP in that subject. Enhancement can also be of beneficial effect in a subject suffering from a disease or pathology such as e.g. a mitochondrial disorder, in that normalizing an energy biomarker may not achieve the optimum outcome for the subject; in such cases, enhancement of one or more energy biomarkers can be beneficial, for example, higher-than-normal levels of ATP, or lower-than-normal levels of lactic acid (lactate) can be beneficial to such a subject.

By modulating, normalizing, or enhancing the energy biomarker Coenzyme Q is meant modulating, normalizing, or enhancing the variant or variants of Coenzyme Q which is predominant in the species of interest. For example, the variant of Coenzyme Q which predominates in humans is Coenzyme Q10. If a species or subject has more than one variant of Coenzyme Q present in significant amounts (i.e., present in amounts which, when modulated, normalized, or enhanced, can have a beneficial effect on the species or subject), modulating, normalizing, or enhancing Coenzyme Q can refer to modulating, normalizing or enhancing any or all variants of Coenzyme Q present in the species or subject.

By "respiratory chain disorder" is meant a disorder which results in the decreased utilization of oxygen by a mitochondrion, cell, tissue, or individual, due to a defect or disorder in a protein or other component contained in the mitochondrial respiratory chain. By "protein or other component contained in the mitochondrial respiratory chain" is meant the components (including, but not limited to, proteins, tetrapyrroles, and cytochromes) comprising mitochondrial complex I, II, III, IV, and/or V. "Respiratory chain protein" refers to the protein components of those complexes, and "respiratory chain protein disorder" is meant a disorder which results in the decreased utilization of oxygen by a mitochondrion, cell, tissue, or individual, due to a defect or disorder in a protein contained in the mitochondrial respiratory chain.

The terms "Parkinson's", (also called "Parkinsonism" and "Parkinsonian syndrome") ("PD") is intended to include not only Parkinson's disease but also drug-induced Parkinsonism and post-encephalitic Parkinsonism. Parkinson's disease is also known as paralysis agitans or shaking palsy. It is characterized by tremor, muscular rigidity and loss of postural reflexes. The disease usually progresses slowly with intervals of 10 to 20 years elapsing before the symptoms cause incapacity. Due to their mimicry of effects of Parkinson's disease, treatment of animals with methamphetamine or MPTP has been used to generate models for Parkinson's disease. These animal models have been used to evaluate the efficacy of various therapies for Parkinson's disease.

The term "Friedreich's ataxia" is intended to embrace other related ataxias, and is also sometimes referred to as hereditary ataxia, familial ataxia, or Friedreich's tabes.

The term "ataxia" is an aspecific clinical manifestation implying dysfunction of parts of the nervous system that coordinate movement, such as the cerebellum. People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias. Ataxias are also often associated with hearing impairments.

There are three types of ataxia, cerebellar ataxia, including vestibulo-cerebellar dysfunction, spino-cerebellar dysfunction, and cerebro-cerebellar dysfunction; sensory ataxia; and vestibular ataxia. Examples of the diseases which are classifiable into spino-cerebellar ataxia or multiple system atrophy are hereditary olivo-ponto-cerebellar atrophy, hereditary cerebellar cortical atrophy, Friedreich's ataxia, Machado-Joseph diseases, Ramsay Hunt syndrome, hereditary dentatorubral-pallidoluysian atrophy, hereditary spastic paraplegia, Shy-Drager syndrome, cortical cerebellar atrophy, striato-nigral degeneration, Marinesco-Sjogren syndrome, alcoholic cortical cerebellar atrophy, paraneoplastic cerebellar atrophy associated with malignant tumor, toxic cerebellar atrophy caused by toxic substances, Vitamin E deficiency due to mutation of a Tocopherol transfer protein (aTTP) or lipid absorption disorder such as Abetalipoproteinemia, cerebellar atrophy associated with endocrine disturbance and the like.

Examples of ataxia symptoms are motor ataxia, trunk ataxia, limb ataxia and the like, autonomic disturbance such as orthostatic hypotension, dysuria, hypohidrosis, sleep apnea, orthostatic syncope and the like, stiffness of lower extremity, ocular nystagmus, oculomotor nerve disorder, pyramidal tract dysfunction, extrapyramidal symptoms (postural adjustment dysfunction, muscular rigidity, akinesia, tremors), dysphagia, lingual atrophy, posterior *funiculus* symptom, muscle atrophy, muscle weakness, deep hyperreflexia, sensory disturbance, scoliosis, kyphoscoliosis, foot deformities, anarthria, dementia, manic state, decreased motivation for rehabilitation and the like.

Polymorphic and Amorphous Forms of (R)-2-hydroxy-2-methyl-4-(2,4,5-trimethyl-3,6-dioxocyclohexa-1,4-dienyl)butanamide Provided herein are various crystalline and amorphous forms of (R)-2-hydroxy-2-methyl-4-(2,4,5-trimethyl-3,6-dioxocyclohexa-1,4-dienyl)butanamide.

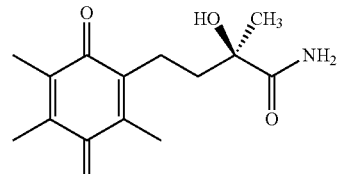

(R)-2-hydroxy-2-methyl-4-(2,4,5-trimethyl-3,6-dioxocyclohexa-1,4-dien-1-yl)butanamide and methods for producing such forms, and methods for using such forms.

Table 1 below provides a summary of certain polymorphic forms of the invention of (R)-2-hydroxy-2-methyl-4-(2,4,5-trimethyl-3,6-di oxocyclohexa-1,4-dienyl)butanamide.

TABLE 1

Summary of (R)-2-hydroxy-2-methyl-4-(2,4,5-trimethyl-3,6-dioxocyclohexa-1,4-dienyl)butanamide Polymorphic Form Characterization

| XRPD [Pattern] (Conditions) | Form Designation | DSC [° C.] | TGA [% Wt. loss] | $^1$H NMR [Residual Solvent] | KF [Wt % water] | Optical Microscopy |
|---|---|---|---|---|---|---|
| Crystalline [Pattern A] (Starting material) | Form I (Anhydrate) | 152.9 | 0.0 | Consistent with structure [0.28 wt % IPA] | 0.1 | Birefringent |
| Crystalline [Pattern B] (RT Slurry in THF) | Form IV (THF Solvate) | 70.5,89.1, 149.7 | 4.7 | Consistent with Structure [6.9 wt % THF] | 0.3 | Birefringent |
| Crystalline [Pattern C] (RT Slurry in 0.5% MC/2% Tween 80) | Form III (Hydrate) | 72.0,150.7 | 2.5, 2.3 | Consistent with structure | 4.3 | Birefringent |
| Crystalline [Pattern D] (Evap Cryst. In 2-MeTHF) | Form V (2-MeTHF Solvate) | 67.2,92.2, 150.6 | 2.7, 5.3 | Consistent with Structure [6.1 wt % 2-MeTHF] | — | Birefringent |
| Crystalline [Pattern E] (Single Solvent fast cooling cryst. in EtOAc) | Form II (Anhydrate) | 133.9,151.3 | 0.4 | Consistent with Structure [0.4 wt. % EtOAc] | 0.1 | Birefringent |
| Crystalline [Pattern F] (Scale up, Single Solvent fast cooling cryst. in 2-MeTHF) | Form VI (2-MeTHF Solvate) | 93.2,135.2, 151.0 | 1.1, 0.2 | Consistent with Structure [3.9 wt. % 2-MeTHF] | 0.1 | Birefringent |

Figure 38:
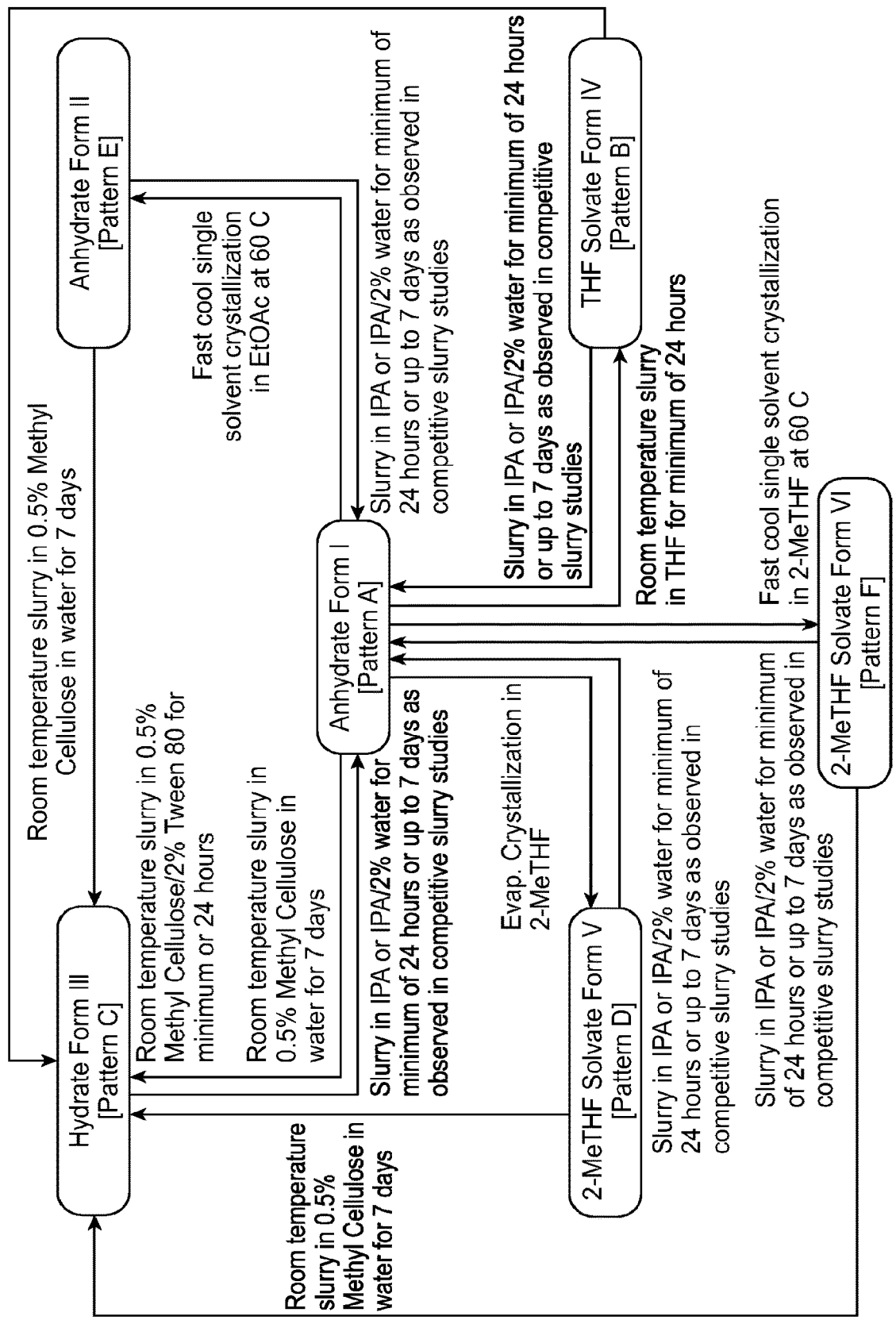
FIG. 38 shows (R)-2-hydroxy-2-methyl-4-(2,4,5-trimethyl-3,6-dioxocyclohexa-1,4-dienyl)butanamide Polymorphic Form-Interrelations.
Figure 39:
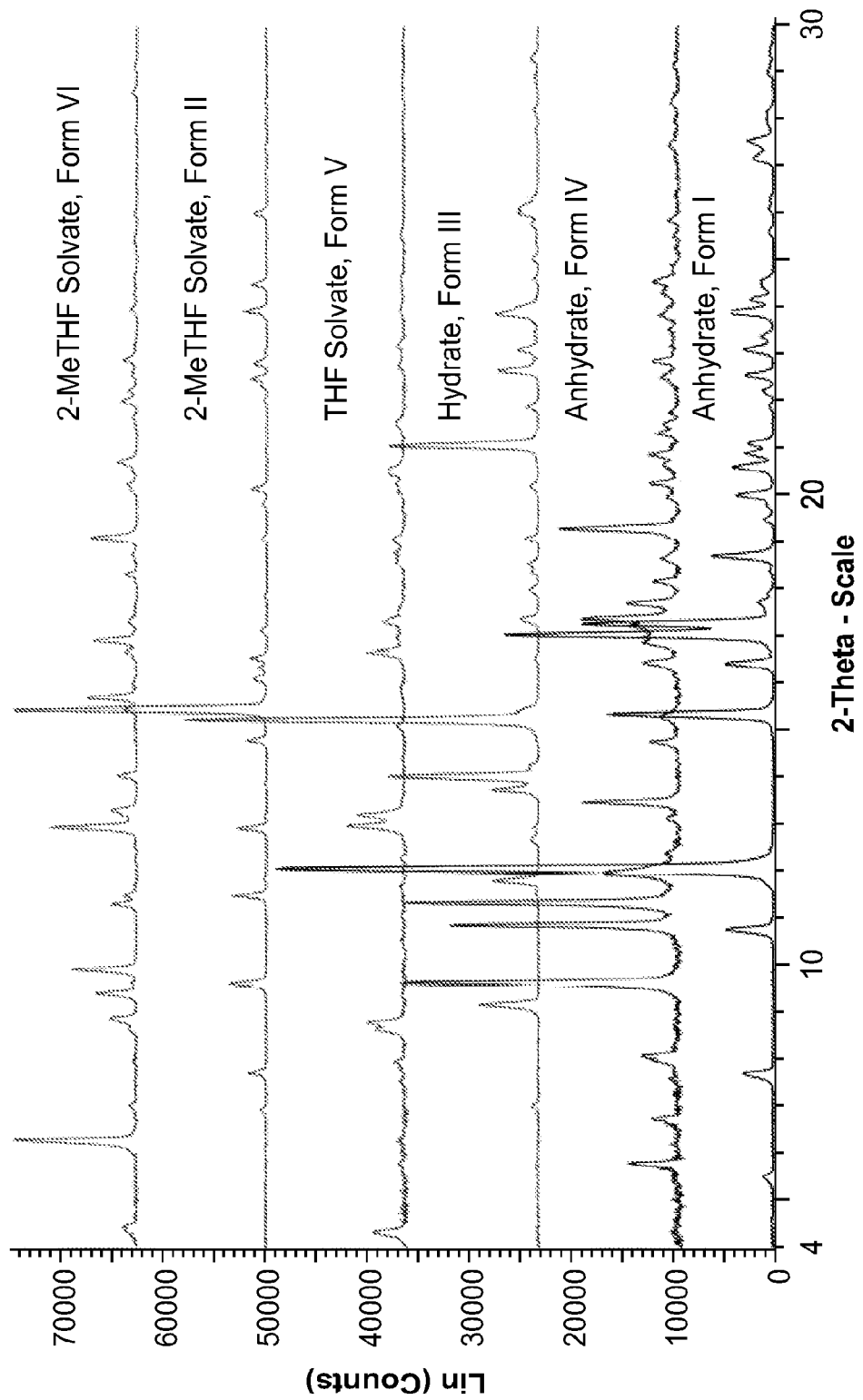
FIG. 39 shows a XRPD stack plot of Edison (R)-2-hydroxy-2-methyl-4-(2,4,5-trimethyl-3,6-dioxocyclohexa-1,4-dienyl)butanamide Polymorphic Forms.

FIG. 38 provides a chart showing interrelations between the various polymorphic forms for (R)-2-hydroxy-2-methyl-4-(2,4,5-trimethyl-3,6-dioxocyclohexa-1,4-dienyl)butanamide. FIG. 39 shows a XRPD stack plot of (R)-2-hydroxy-2-methyl-4-(2,4,5-trimethyl-3,6-dioxocyclohexa-1,4-dienyl)butanamide polymorphic forms.

Table A provides various embodiments of angular positions of certain characteristic peaks in powder x-ray diffraction for the polymorphic forms of the invention. In some embodiments, the angular positions may vary by ±0.2. In some embodiments, the angular positions may vary by ±0.1. In some embodiments, the angular positions may vary by ±0.05. In some embodiments, the angular positions may vary by ±0.02.

TABLE A

Angular Positions of Certain Characteristic Peaks in Powder X-ray Diffraction for Forms I-VI

| Form | Angular Positions of Certain Characteristic Peaks (Angle, 2 theta) (all ± 0.2) |
|---|---|
| I | Embodiment 1. 12.06, 17.03, 17.26 |
| | Embodiment 2. 12.06, 15.33, 17.03, 17.26, 18.72 |
| | Embodiment 3. 7.67, 10.75, 12.06, 15.33, 16.41, 17.03, 17.26, 18.72, 20.04, 23.92 |
| | Embodiment 4. 7.67, 10.75, 12.06, 15.33, 16.41, 17.03, 17.26, 18.72, 20.04, 20.64, 20.91, 21.14, 22.58, 23.13, 23.92, 24.19, 24.53, 27.21, 27.56 |
| | Embodiment 5. 5.48, 7.67, 10.75, 12.06, 15.33, 16.41, 17.03, 17.26, 17.71, 17.94, 18.40, 18.72, 19.51, 20.04, 20.64, 20.91, 21.14, 21.55, 21.91, 22.25, 22.58, 23.13, 23.41, 23.92, 24.19, 24.53, 25.64, 26.13, 26.34, 27.21, 27.56, 28.01, 29.04, 29.46 |
| | Embodiment 6. 12.06, 15.33, 17.03, 17.26. |
| | Embodiment 7. 12.06, 15.33, 17.03, 17.26, 18.72, 23.92. |
| | Embodiment 8. 12.06, 15.33, 17.03, 17.26, 18.72, 23.92, 16.41 |
| | Embodiment 9. 12.06, 15.33, 17.03, 17.26, 18.72, 23.92, 16.41, 10.75 |
| | Embodiment 10. 12.06, 15.33, 17.03, 17.26, 18.72, 23.92, 16.41, 10.75, 20.64 |
| V | Embodiment 1. 9.61, 11.49, 15.45 |
| | Embodiment 2. 9.61, 11.49, 12.93, 15.45, 23.96, 26.05 |
| | Embodiment 3. 9.61, 11.49, 12.93, 14.80, 15.45, 16.53, 23.96, 24.54, 26.05 |
| | Embodiment 4. 9.61, 11.49, 12.93, 14.80, 15.45, 16.10, 16.34, 16.53, 20.18, 22.52, 22.86, 23.96, 24.54, 26.05 |
| | Embodiment 5. 6.91, 7.72, 9.61, 11.49, 11.86, 12.93, 13.19, 13.87, 14.80, 15.45, 16.10, 16.34, 16.53, 17.14, 17.85, 19.12, 19.85, 20.18, 21.00, 22.06, 22.52, 22.86, 23.09, 23.96, 24.54, 25.26, 26.05, 26.90 |
| | Embodiment 6. 9.61, 11.49, 12.93, 15.45 |
| | Embodiment 7. 9.61, 11.49, 12.93, 15.45, 23.96 |
| | Embodiment 8. 9.61, 11.49, 12.93, 15.45, 14.80 |
| | Embodiment 9. 9.61, 11.49, 12.93, 15.45, 7.72 |
| | Embodiment 10. 9.61, 11.49, 12.93, 15.45, 7.72, 16.53 |
| III | Embodiment 1. 14.02, 15.23, 21.10 |
| | Embodiment 2. 9.16, 14.02, 15.23, 21.10, 22.69 |
| | Embodiment 3. 9.16, 11.81, 13.74, 14.02, 15.23, 21.10, 22.69, 23.90 |
| | Embodiment 4. 9.16, 11.81, 13.74, 14.02, 15.23, 17.35, 21.10, 22.69, 23.15, 23.90, 26.10 |
| | Embodiment 5. 9.16, 11.53, 11.81, 12.68, 12.93, 13.74, 14.02, 15.23, 16.53, 17.35, 17.98, 18.54, 19.09, 20.23, 21.10, 21.93, 22.69, 23.15, 23.50, 23.90, 24.65, 25.09, 25.46, 25.79, 26.10, 27.79, 28.22, 28.93, 29.33 |
| | Embodiment 6. 9.16, 14.02, 15.23, 21.10 |
| | Embodiment 7. 9.16, 13.74, 14.02, 15.23, 21.10 |
| | Embodiment 8. 9.16, 11.81, 13.74, 14.02, 15.23, 21.10 |
| | Embodiment 9. 9.16, 11.81, 13.74, 14.02, 15.23, 21.10, 23.90 |
| | Embodiment 10. 9.16, 11.81, 13.74, 14.02, 15.23, 21.10, 22.69, 23.90 |
| II | Embodiment 1. 9.63, 11.33, 19.33 |
| | Embodiment 2. 9.63, 10.85, 11.33, 13.47, 19.33 |
| | Embodiment 3. 5.76, 8.04, 9.63, 10.85, 11.33, 11.97, 13.47, 14.75, 17.37, 17.71, 19.33 |
| | Embodiment 4. 5.76, 8.04, 9.63, 10.85, 11.33, 11.97, 13.47, 14.75, 16.42, 16.89, 17.37, 17.71, 19.33, 22.89, 24.59 |
| | Embodiment 5. 5.76, 6.72, 7.57, 8.04, 9.63, 10.85, 11.33, 11.97, 12.38, 13.13, 13.47, 14.75, 15.28, 16.42, 16.89, 17.37, 17.71, 18.17, 18.66, 19.33, 20.01, 20.29, 20.67, 20.90, 21.36, 21.54, 21.80, 22.55, 22.89, 23.27, 23.54, 23.87, 24.35, 24.59, 24.87, 25.29, 25.55, 25.89, 26.44, 27.49, 28.01, 28.39, 29.17 |
| | Embodiment 6. 9.63, 11.33, 10.85 |
| | Embodiment 7. 9.63, 11.33, 10.85, 19.33 |
| | Embodiment 8. 9.63, 11.33, 10.85, 19.33, 17.37 |
| | Embodiment 9. 9.63, 11.33, 10.85, 19.33, 17.37, 13.47 |
| | Embodiment 10. 9.63, 11.33, 10.85, 19.33, 17.37, 13.47, 11.97 |
| IV | Embodiment 1. 4.31, 12.97, 13.20 |
| | Embodiment 2. 4.31, 8.76, 12.97, 13.20, 16.66 |
| | Embodiment 3. 4.31, 7.94, 8.76, 12.97, 13.20, 16.66, 17.33, 20.57 |
| | Embodiment 4. 4.31, 7.94, 8.76, 12.97, 13.20, 15.08, 16.66, 17.33, 19.09, 20.57, 21.58 |
| | Embodiment 5. 4.31, 5.77, 6.28, 7.53, 7.94, 8.76, 9.39, 9.87, 10.54, 11.07, 11.68, 12.02, 12.28, 12.97, 13.20, 13.52, 14.40, 15.08, 15.90, 16.66, 16.96, 17.33, 17.59, 18.77, 19.09, 19.74, 20.27, 20.57, 21.09, 21.58, 22.81, 23.23, 24.01, 24.65, 25.60 |
| | Embodiment 6. 12.97, 13.20, 8.76 |
| | Embodiment 7. 12.97, 13.20, 8.76, 16.66 |
| | Embodiment 8. 12.97, 13.20, 8.76, 16.66, 4.31 |
| | Embodiment 9. 12.97, 13.20, 8.76, 16.66, 4.31, 17.33 |
| | Embodiment 10. 12.97, 13.20, 8.76, 16.66, 4.31, 17.33, 20.57 |

TABLE A-continued

Angular Positions of Certain Characteristic
Peaks in Powder X-ray Diffraction for Forms I-VI

| Form | Angular Positions of Certain Characteristic Peaks (Angle, 2 theta) (all ± 0.2) |
|---|---|
| VI | Embodiment 1. 6.27, 9.91, 12.94 |
| | Embodiment 2. 6.27, 9.41, 9.91, 12.94, 13.29 |
| | Embodiment 3. 6.27, 8.85, 9.41, 9.91, 12.94, 13.29, 16.67, 19.13 |
| | Embodiment 4. 4.39, 6.27, 8.85, 9.41, 9.91, 11.32, 12.94, 13.29, 14.03, 16.67, 19.13, 20.76, 22.06 |
| | Embodiment 5. 4.39, 6.27, 7.00, 8.62, 8.85, 9.41, 9.91, 11.32, 11.50, 12.25, 12.56, 12.94, 13.29, 14.03, 14.82, 15.10, 15.44, 15.71, 16.01, 16.67, 16.91, 17.33, 17.59, 18.33, 18.75, 19.13, 20.25, 20.76, 21.68, 22.06, 22.27, 22.61, 22.94, 24.01, 24.33, 24.65, 25.48, 26.05, 28.63, 29.18 |
| | Embodiment 6. 6.27, 9.91, 12.94, 15.71 |
| | Embodiment 7. 6.27, 9.91, 12.94, 15.71, 19.13 |
| | Embodiment 8. 6.27, 9.91, 12.94, 15.71, , 16.91, 19.13 |
| | Embodiment 9. 6.27, 9.41, 9.91, 12.94, 15.71, , 16.91, 19.13 |
| | Embodiment 10. 6.27, 8.85, 9.41, 9.91, 12.94, 15.71, , 16.91, 19.13 |

Tables 2-7 provide additional embodiments of angular positions of characteristic peaks in powder x-ray diffraction for the polymorphic forms of the invention. In some embodiments, a polymorphic form is characterized by the angular positions of characteristics peaks shown in Table A. In some embodiments, the polymorphic form is characterized by 3 or more (e.g. 4, 5, 6, 7, 8, 9, 10, or more than 10) angular positions of characteristic peaks in powder x-ray diffraction as shown in Tables 2-7 below. In some embodiments, the angular positions may vary by ±0.2. In some embodiments, the angular positions may vary by ±0.1. In some embodiments, the angular positions may vary by ±0.05. In some embodiments, the angular positions may vary by ±0.02.

As a non-limiting example, polymorph Form I may be characterized by 3, 4, 5, 6, 7, 8, 9, 10, or more angular positions as shown in Table 2.

Table 2. Angular Positions of Characteristic Peaks in Powder X-Ray Diffraction for Pattern A (Anhydrate Form I)

Polymorph Form I may be characterized by 3, 4, 5, 6, 7, 8, 9, 10, or more angular positions as shown below:

TABLE 2

Angular Positions of Characteristic Peaks in Powder
X-ray Diffraction for Pattern A (Anhydrate Form I)

| Angle, 2 theta | d spacing, Å |
|---|---|
| 5.48 | 16.1 |
| 7.67 | 11.5 |
| 10.75 | 8.2 |
| 12.06 | 7.3 |
| 15.33 | 5.8 |
| 16.41 | 5.4 |
| 17.03 | 5.2 |
| 17.26 | 5.1 |
| 17.71 | 5.0 |
| 17.94 | 4.9 |
| 18.40 | 4.8 |
| 18.72 | 4.7 |
| 19.51 | 4.5 |
| 20.04 | 4.4 |
| 20.64 | 4.3 |
| 20.91 | 4.2 |
| 21.14 | 4.2 |
| 21.55 | 4.1 |
| 21.91 | 4.1 |
| 22.25 | 4.0 |
| 22.58 | 3.9 |
| 23.13 | 3.8 |
| 23.41 | 3.8 |
| 23.92 | 3.7 |

TABLE 2-continued

Angular Positions of Characteristic Peaks in Powder
X-ray Diffraction for Pattern A (Anhydrate Form I)

| Angle, 2 theta | d spacing, Å |
|---|---|
| 24.19 | 3.7 |
| 24.53 | 3.6 |
| 25.64 | 3.5 |
| 26.13 | 3.4 |
| 26.34 | 3.4 |
| 27.21 | 3.3 |
| 27.56 | 3.2 |
| 28.01 | 3.2 |
| 29.04 | 3.1 |
| 29.46 | 3.0 |

In some examples, polymorph Form I is characterized by at least 3 or more angular positions. In certain examples, these angular positions include 12.06, 17.03, and 17.26±0.2.

In some examples, polymorph Form I is characterized by at least 4 or more angular positions. In certain examples, these at least four angular positions include 12.1, 17.0, 17.3, and 15.33±0.2. In certain examples, these at least four angular positions include 12.1, 17.0, 17.3, 15.33, and 18.72±0.2.

Table 3. Angular Positions of Characteristic Peaks in Powder X-Ray Diffraction for Pattern D (2-MeTHF Solvate Form V)

Polymorph Form V may be characterized by 3, 4, 5, 6, 7, 8, 9, 10, or more angular positions as shown below:

TABLE 4

Angular Positions of Characteristic Peaks in Powder
X-ray Diffraction for Pattern C (Hydrate Form III)

| Angle, 2 theta | d spacing, Å |
|---|---|
| 6.91 | 12.8 |
| 7.72 | 11.4 |
| 9.61 | 9.2 |
| 11.49 | 7.7 |
| 11.86 | 7.5 |
| 12.93 | 6.8 |
| 13.19 | 6.7 |
| 13.87 | 6.4 |
| 14.80 | 6.0 |
| 15.45 | 5.7 |
| 16.10 | 5.5 |
| 16.34 | 5.4 |
| 16.53 | 5.4 |
| 17.14 | 5.2 |

TABLE 4-continued

Angular Positions of Characteristic Peaks in Powder X-ray Diffraction for Pattern C (Hydrate Form III)

| Angle, 2 theta | d spacing, Å |
|---|---|
| 17.85 | 5.0 |
| 19.12 | 4.6 |
| 19.85 | 4.5 |
| 20.18 | 4.4 |
| 21.00 | 4.2 |
| 22.06 | 4.0 |
| 22.52 | 3.9 |
| 22.86 | 3.9 |
| 23.09 | 3.8 |
| 23.96 | 3.7 |
| 24.54 | 3.6 |
| 25.26 | 3.5 |
| 26.05 | 3.4 |
| 26.90 | 3.3 |

Polymorph Form III may be characterized by 3, 4, 5, 6, 7, 8, 9, 10, or more angular positions as shown below:

TABLE 5

Angular Positions of Characteristic Peaks in Powder X-ray Diffraction for Pattern E (Anhydrate II)

| Angle, 2 theta | d spacing, Å |
|---|---|
| 9.16 | 9.6 |
| 11.53 | 7.7 |
| 11.81 | 7.5 |
| 12.68 | 7.0 |
| 12.93 | 6.8 |
| 13.74 | 6.4 |
| 14.02 | 6.3 |
| 15.23 | 5.8 |
| 16.53 | 5.4 |
| 17.35 | 5.1 |
| 17.98 | 4.9 |
| 18.54 | 4.8 |
| 19.09 | 4.6 |
| 20.23 | 4.4 |
| 21.10 | 4.2 |
| 21.93 | 4.0 |
| 22.69 | 3.9 |
| 23.15 | 3.8 |
| 23.50 | 3.8 |
| 23.90 | 3.7 |
| 24.65 | 3.6 |
| 25.09 | 3.5 |
| 25.46 | 3.5 |
| 25.79 | 3.5 |
| 26.10 | 3.4 |
| 27.79 | 3.2 |
| 28.22 | 3.2 |
| 28.93 | 3.1 |
| 29.33 | 3.0 |

Polymorph Form II may be characterized by 3, 4, 5, 6, 7, 8, 9, 10, or more angular positions as shown below:

TABLE 6

Angular Positions of Characteristic Peaks in Powder X-ray Diffraction for Pattern B (THF Solvate Form IV)

| Angle, 2 theta | d spacing, Å |
|---|---|
| 5.76 | 15.3 |
| 6.72 | 13.2 |
| 7.57 | 11.7 |
| 8.04 | 11.0 |

TABLE 6-continued

Angular Positions of Characteristic Peaks in Powder X-ray Diffraction for Pattern B (THF Solvate Form IV)

| Angle, 2 theta | d spacing, Å |
|---|---|
| 9.63 | 9.2 |
| 10.85 | 8.1 |
| 11.33 | 7.8 |
| 11.97 | 7.4 |
| 12.38 | 7.1 |
| 13.13 | 6.7 |
| 13.47 | 6.6 |
| 14.75 | 6.0 |
| 15.28 | 5.8 |
| 16.42 | 5.4 |
| 16.89 | 5.2 |
| 17.37 | 5.1 |
| 17.71 | 5.0 |
| 18.17 | 4.9 |
| 18.66 | 4.8 |
| 19.33 | 4.6 |
| 20.01 | 4.4 |
| 20.29 | 4.4 |
| 20.67 | 4.3 |
| 20.90 | 4.2 |
| 21.36 | 4.2 |
| 21.54 | 4.1 |
| 21.80 | 4.1 |
| 22.55 | 3.9 |
| 22.89 | 3.9 |
| 23.27 | 3.8 |
| 23.54 | 3.8 |
| 23.87 | 3.7 |
| 24.35 | 3.7 |
| 24.59 | 3.6 |
| 24.87 | 3.6 |
| 25.29 | 3.5 |
| 25.55 | 3.5 |
| 25.89 | 3.4 |
| 26.44 | 3.4 |
| 27.49 | 3.2 |
| 28.01 | 3.2 |
| 28.39 | 3.1 |
| 29.17 | 3.1 |

Polymorph Form IV may be characterized by 3, 4, 5, 6, 7, 8, 9, 10, or more angular positions as shown below:

TABLE 7

Angular Positions of Characteristic Peaks in Powder X-ray Diffraction for Pattern F (2-MeTHF Solvate Form VI)

| Angle, 2 theta | d spacing, Å |
|---|---|
| 4.31 | 20.5 |
| 5.77 | 15.3 |
| 6.28 | 14.1 |
| 7.53 | 11.7 |
| 7.94 | 11.1 |
| 8.76 | 10.1 |
| 9.39 | 9.4 |
| 9.87 | 9.0 |
| 10.54 | 8.4 |
| 11.07 | 8.0 |
| 11.68 | 7.6 |
| 12.02 | 7.4 |
| 12.28 | 7.2 |
| 12.97 | 6.8 |
| 13.20 | 6.7 |
| 13.52 | 6.5 |
| 14.40 | 6.1 |
| 15.08 | 5.9 |
| 15.90 | 5.6 |
| 16.66 | 5.3 |
| 16.96 | 5.2 |

TABLE 7-continued

Angular Positions of Characteristic Peaks in
Powder X-ray Diffraction for Pattern F
(2-MeTHF Solvate Form VI)

| Angle, 2 theta | d spacing, A |
| --- | --- |
| 17.33 | 5.1 |
| 17.59 | 5.0 |
| 18.77 | 4.7 |
| 19.09 | 4.6 |
| 19.74 | 4.5 |
| 20.27 | 4.4 |
| 20.57 | 4.3 |
| 21.09 | 4.2 |
| 21.58 | 4.1 |
| 22.81 | 3.9 |
| 23.23 | 3.8 |
| 24.01 | 3.7 |
| 24.65 | 3.6 |
| 25.60 | 3.5 |

Polymorph Form VI may be characterized by 3, 4, 5, 6, 7, 8, 9, 10, or more angular positions as shown below:

| Angle, 2 theta | d spacing, A |
| --- | --- |
| 4.39 | 20.1 |
| 6.27 | 14.1 |
| 7.00 | 12.6 |
| 8.62 | 10.3 |
| 8.85 | 10.0 |
| 9.41 | 9.4 |
| 9.91 | 8.9 |
| 11.32 | 7.8 |
| 11.50 | 7.7 |
| 12.25 | 7.2 |
| 12.56 | 7.0 |
| 12.94 | 6.8 |
| 13.29 | 6.7 |
| 14.03 | 6.3 |
| 14.82 | 6.0 |
| 15.10 | 5.9 |
| 15.44 | 5.7 |
| 15.71 | 5.6 |
| 16.01 | 5.5 |
| 16.67 | 5.3 |
| 16.91 | 5.2 |
| 17.33 | 5.1 |
| 17.59 | 5.0 |
| 18.33 | 4.8 |
| 18.75 | 4.7 |
| 19.13 | 4.6 |
| 20.25 | 4.4 |
| 20.76 | 4.3 |
| 21.68 | 4.1 |
| 22.06 | 4.0 |
| 22.27 | 4.0 |
| 22.61 | 3.9 |
| 22.94 | 3.9 |
| 24.01 | 3.7 |
| 24.33 | 3.7 |
| 24.65 | 3.6 |
| 25.48 | 3.5 |
| 26.05 | 3.4 |
| 28.63 | 3.1 |
| 29.18 | 3.1 |

Certain polymorphic or amorphous forms of a drug can have advantageous characteristics versus other forms, which can affect the desirability of the drug from a pharmaceutical and/or manufacturing perspective, for example: increased stability, increased solubility, better handling properties, lack of associated undesired solvents (e.g. solvates with toxic solvents), increased purity, better particle size and/or distribution, improved bulk density, and ease of manufacture.

Forms I, II, III and the amorphous form are anhydrates or hydrates, are advantageously are not solvates with undesired solvents (e.g. THF and 2-MeTHF).

Forms I-IV and VI were shown to have good solubilities in water (each >1.3 mg/ml), with Form I having the highest aqueous solubility at 1.74 mg/ml (Example 10). Furthermore, Form I was shown to be soluble in a variety of polar and non-polar solvents (Example 2), indicating an ability to be administered using a variety of solvents. In some embodiments, it is advantageous for a drug to have a physiological log D close to zero; solubility in polar and non-polar solvents thus indicates a more favorable physiological log D. Form I was further shown to have increased solubility in a simple detergent (0.5% MC/2% Tween 80) (Example 2); such solubility in simple detergents may be advantageous, as these conditions may mimic gut conditions for oral administration of the drug. Form III (Hydrate), is formed under simple detergent conditions, and thus Form III may be the form of the drug that will be produced in the gut.

Forms I, II, and III advantageously demonstrated stability to elevated humidity (Example 8). Form I was also tested by grinding, and showed stability to grinding (Example 9). As shown in the examples, the experiments performed indicated that Form I was highly stable.

Forms that are non-hygroscopic are easier to handle from a manufacturing perspective; as shown in Example 11, Forms I, II, IV, and VI were non-hygroscopic.

Certain particle shapes and sizes may be advantageous: particles that are closer to spherical may be preferred, with plates and needles less preferred. As shown in Example 11, Forms I, II, and III had more favorable shapes, whereas Form VI was plate shaped, and Form IV needle-shaped. Regarding particle size, smaller, more homogenous sizes may be preferred. Smaller particles may have increased bioavailability, may be easier to dissolve, and may be easier to handle due to decreased drying times. Furthermore, smaller particles may not require a micronizing step that may be required for larger particles. As shown in the Figures, Forms I-III had more favorable particle sizes than IV and VI.

Higher melting points may indicate a form with improved handling characteristics (e.g. easier to dry and process) and more thermal stability. Form I had the highest melting point of Forms I-VI. Furthermore, a single peak may in some embodiments be preferred, as multiple peaks may indicate conversion to a different form. Form I had a single DSC peak, all others had two or three.

The various forms (polymorphs and amorphous) of (R)-2-hydroxy-2-methyl-4-(2,4,5-trimethyl-3,6-dioxocyclohexa-1,4-dienyl)butanamide may also be utilized as intermediates in making a desired form. As a non-limiting example, if a preferred synthetic method for making (R)-2-hydroxy-2-methyl-4-(2,4,5-trimethyl-3,6-dioxocyclohexa-1,4-dienyl)butanamide results in a non-preferred form, the non-preferred form may be utilized as an intermediate to make the desired form.

Diseases Amenable to Treatment or Suppression with Compositions and Methods of the Invention A variety of disorders/diseases are believed to be caused or aggravated by oxidative stress affecting normal electron flow in the cells, such as mitochondrial disorders, impaired energy processing disorders, neurodegenerative diseases and diseases of aging, and can be treated or suppressed using the polymorphic and amorphous forms of (R)-2-hydroxy-2-methyl-4-(2,4,5-trimethyl-3,6-dioxocyclohexa-1,4-dienyl) butanamide and methods of the invention.

Non-limiting examples of oxidative stress disorders include, for example, mitochondrial disorders (including inherited mitochondrial diseases) such as Alpers Disease, Barth syndrome, Beta-oxidation Defects, Carnitine-Acyl-Carnitine Deficiency, Carnitine Deficiency, Creatine Deficiency Syndromes, Co-Enzyme Q10 Deficiency, Complex I Deficiency, Complex II Deficiency, Complex III Deficiency, Complex IV Deficiency, Complex V Deficiency, COX Deficiency, chronic progressive external ophthalmoplegia (CPEO), CPT I Deficiency, CPT II Deficiency, Friedreich's Ataxia (FA), Glutaric Aciduria Type II, Kearns-Sayre Syndrome (KSS), Lactic Acidosis, Long-Chain Acyl-CoA Dehydrogenase Deficiency (LCAD), LCHAD, Leigh Disease or Syndrome, Leigh-like Syndrome, Leber's Hereditary Optic Neuropathy (LHON, also referred to as Leber's Disease, Leber's Optic Atrophy (LOA), or Leber's Optic Neuropathy (LON)), Lethal Infantile Cardiomyopathy (LIC), Luft Disease, Multiple Acyl-CoA Dehydrogenase Deficiency (MAD), Medium-Chain Acyl-CoA Dehydrogenase Deficiency (MCAD), Mitochondrial Myopathy, Encephalopathy, Lactacidosis, Stroke (MELAS), Myoclonic Epilepsy with Ragged Red Fibers (MERRF), Mitochondrial Recessive Ataxia Syndrome (MIRAS), Mitochondrial Cytopathy, Mitochondrial DNA Depletion, Mitochondrial Encephalopathy, Mitochondrial Myopathy, Myoneurogastrointestinal Disorder and Encephalopathy (MNGIE), Neuropathy, Ataxia, and Retinitis Pigmentosa (NARP), Pearson Syndrome, Pyruvate Carboxylase Deficiency, Pyruvate Dehydrogenase Deficiency, POLG Mutations, Respiratory Chain Disorder, Short-Chain Acyl-CoA Dehydrogenase Deficiency (SCAD), SCHAD, Very Long-Chain Acyl-CoA Dehydrogenase Deficiency (VLCAD); myopathies such as cardiomyopathy and encephalomyopathy; neurodegenerative diseases such as Parkinson's disease, Alzheimer's disease, and amyotrophic lateral sclerosis (ALS, also known as Lou Gehrig's disease); motor neuron diseases; neurological diseases such as epilepsy; age-associated diseases, particularly diseases for which CoQ10 has been proposed for treatment, such as macular degeneration, diabetes (e.g. Type 2 diabetes mellitus), metabolic syndrome, and cancer (e.g. brain cancer); genetic diseases such as Huntington's Disease (which is also a neurological disease); mood disorders such as schizophrenia and bipolar disorder; pervasive developmental disorders such as autistic disorder, Asperger's syndrome, childhood disintegrative disorder (CDD), Rett's disorder, and PDD-not otherwise specified (PDD-NOS); cerebrovascular accidents such as stroke; vision impairments such as those caused by neurodegenerative diseases of the eye such as optic neuropathy, Leber's hereditary optic neuropathy, dominant inherited juvenile optic atrophy, optic neuropathy caused by toxic agents, glaucoma, age-related macular degeneration (both "dry" or non-exudative macular degeneration and "wet" or exudative macular degeneration), Stargardt's macular dystrophy, diabetic retinopathy, diabetic maculopathy, retinopathy of prematurity, or ischemic reperfusion-related retinal injury; disorders caused by energy impairment include diseases due to deprivation, poisoning or toxicity of oxygen, and qualitative or quantitative disruption in the transport of oxygen such as haemoglobionopathies, for example thalassemia or sickle cell anemia; other diseases in which mitochondrial dysfunction is implicated such as excitoxic, neuronal injury, such as that associated with seizures, stroke and ischemia; and other disorders including renal tubular acidosis; attention deficit/hyperactivity disorder (ADHD); neurodegenerative disorders resulting in hearing or balance impairment; Dominant Optic Atrophy (DOA); Maternally inherited diabetes and deafness (MIDD); chronic fatigue; contrast-induced kidney damage; contrast-induced retinopathy damage; Abetalipoproteinemia; retinitis pigmentosum; Wolfram's disease; Tourette syndrome; cobalamin c defect; methylmalonic aciduria; glioblastoma; Down's syndrome; acute tubular necrosis; muscular dystrophies; leukodystrophies; Progressive Supranuclear Palsy; spinal muscular atrophy; hearing loss (e.g. noise induced hearing loss); traumatic brain injury; Juvenile Huntington's Disease; Multiple Sclerosis; NGLY1; Multiple System Atrophy; Adrenoleukodystrophy; and Adrenomyeloneuropathy. It is to be understood that certain specific diseases or disorders may fall within more than one category; for example, Huntington's Disease is a genetic disease as well as a neurological disease. Furthermore, certain oxidative stress diseases and disorders may also be considered mitochondrial disorders.

For some disorders amenable to treatment with compounds and methods of the invention, the primary cause of the disorder is due to a defect in the respiratory chain or another defect preventing normal utilization of energy in mitochondria, cells, or tissue(s). Non-limiting examples of disorders falling in this category include inherited mitochondrial diseases, such as Myoclonic Epilepsy with Ragged Red Fibers (MERRF), Mitochondrial Myopathy, Encephalopathy, Lactacidosis, and Stroke (MELAS), Leber's Hereditary Optic Neuropathy (LHON, also referred to as Leber's Disease, Leber's Optic Atrophy (*LOA*), or Leber's Optic Neuropathy (LON)), Leigh Disease or Leigh Syndrome, Kearns-Sayre Syndrome (KSS), and Friedreich's Ataxia (FA). For some disorders amenable to treatment with compounds and methods of the invention, the primary cause of the disorder is not due to respiratory chain defects or other defects preventing normal utilization of energy in mitochondria, cells, or tissue(s); non-limiting examples of disorders falling in this category include stroke, cancer, and diabetes. However, these latter disorders are particularly aggravated by energy impairments, and are particularly amenable to treatment with compounds of the invention in order to ameliorate the condition. Pertinent examples of such disorders include ischemic stroke and hemorrhagic stroke, where the primary cause of the disorder is due to impaired blood supply to the brain. While an ischemic episode caused by a thrombosis or embolism, or a hemorrhagic episode caused by a ruptured blood vessel, is not primarily caused by a defect in the respiratory chain or another metabolic defect preventing normal utilization of energy, oxidative stress plays a role in the ischemic cascade due to oxygen reperfusion injury following hypoxia (this cascade occurs in heart attacks as well as in strokes). Accordingly, treatment with compounds and methods of the invention will mitigate the effects of the disease, disorder or condition. Modulating one or more energy biomarkers, normalizing one or more energy biomarkers, or enhancing one or more energy biomarkers can also prove beneficial in such disorders both as a therapeutic measure and a prophylactic measure. For example, for a patient scheduled to undergo non-emergency repair of an aneurysm, enhancing energy biomarkers before and during the pre-operative can improve the patient's prognosis should the aneurysm rupture before successful repair.

The term "oxidative stress disorder" or "oxidative stress disease" encompass both diseases caused by oxidative stress and diseases aggravated by oxidative stress. The terms "oxidative stress disorder" or "oxidative stress disease" encompass both diseases and disorders where the primary cause of the disease is due to a defect in the respiratory chain or another defect preventing normal utilization of energy in mitochondria, cells, or tissue(s), and also diseases and disorders where the primary cause of the disease is not due to a defect in the respiratory chain or another defect preventing normal utilization of energy in mitochondria, cells, or tissue(s). The former set of diseases can be referred to as "primary oxidative stress disorders," while the latter can be referred to as "secondary oxidative stress disorders." It should be noted that the distinction between "diseases caused by oxidative stress" and "diseases aggravated by oxidative stress" is not absolute; a disease may be both a disease caused by oxidative stress and a disease aggravated by oxidative stress. The boundary between "primary oxidative stress disorder" and a "secondary oxidative stress disorder" is more distinct, provided that there is only one primary cause of a disease or disorder and that primary cause is known.

Bearing in mind the somewhat fluid boundary between diseases caused by oxidative stress and diseases aggravated by oxidative stress, mitochondrial diseases or disorders and impaired energy processing diseases and disorders tend to fall into the category of diseases caused by oxidative stress, while neurodegenerative disorders and diseases of aging tend to fall into the category of diseases aggravated by oxidative stress. Mitochondrial diseases or disorders and impaired energy processing diseases and disorders are generally primary oxidative stress disorders, while neurodegenerative disorders and diseases of aging may be primary or secondary oxidative stress disorders Clinical Assessment of Oxidative Stress and Efficacy of Therapy Several readily measurable clinical markers are used to assess the metabolic state of patients with oxidative stress disorders. These markers can also be used as indicators of the efficacy of a given therapy, as the level of a marker is moved from the pathological value to the healthy value. These clinical markers include, but are not limited to, energy biomarkers such as lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; total, reduced or oxidized glutathione levels, or reduced/oxidized glutathione ratio either in whole blood, plasma, lymphocytes, cerebrospinal fluid, or cerebral ventricular fluid; total, reduced or oxidized cysteine levels, or reduced/oxidized cysteine ratio either in whole blood, plasma, lymphocytes, cerebrospinal fluid, or cerebral ventricular fluid; phosphocreatine levels, NADH (NADH+H+) or NADPH (NADPH+H+) levels; NAD or NADP levels; ATP levels; anaerobic threshold; reduced coenzyme Q ($CoQ_{red}$) levels; oxidized coenzyme Q ($CoQ_{ox}$) levels; total coenzyme Q ($CoQ_{tot}$) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2). Several of these clinical markers are measured routinely in exercise physiology laboratories, and provide convenient assessments of the metabolic state of a subject. In one embodiment of the invention, the level of one or more energy biomarkers in a patient suffering from an oxidative stress disorder, such as Friedreich's ataxia, Leber's hereditary optic neuropathy, MELAS, KSS or CoQ10 deficiency, is improved to within two standard deviations of the average level in a healthy subject. In another embodiment of the invention, the level of one or more of these energy biomarkers in a patient suffering from an oxidative stress disorder, such as Friedreich's ataxia, Leber's hereditary optic neuropathy, MELAS, KSS or CoQ10 deficiency is improved to within one standard deviation of the average level in a healthy subject. Exercise intolerance can also be used as an indicator of the efficacy of a given therapy, where an improvement in exercise tolerance (i.e., a decrease in exercise intolerance) indicates efficacy of a given therapy.

Several metabolic biomarkers have already been used to evaluate efficacy of CoQ10, and these metabolic biomarkers can be monitored as energy biomarkers for use in the methods of the current invention. Lactate, a product of the anaerobic metabolism of glucose, is removed by reduction to pyruvate in an aerobic setting or by oxidative metabolism, which is dependent on a functional mitochondrial respiratory chain. Dysfunction of the respiratory chain may lead to inadequate removal of lactate and pyruvate from the circulation and elevated lactate/pyruvate ratios are observed in mitochondrial cytopathies (see Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)). Blood lactate/pyruvate ratio (Chariot et al., Arch. Pathol. Lab. Med. 118(7):695-7 (1994)) is, therefore, widely used as a noninvasive test for detection of mitochondrial cytopathies (see again Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)) and toxic mitochondrial myopathies (Chariot et al., Arthritis Rheum. 37(4): 583-6 (1994)). Changes in the redox state of liver mitochondria can be investigated by measuring the arterial ketone body ratio (acetoacetate/3-hydroxybutyrate: AKBR) (Ueda et al., J. Cardiol. 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., FEBS Lett. 409(2):287-91 (1997); Honda et al., Leuk. Res. 24(6):461-8 (2000); Pilger et al., Free Radic. Res. 35(3):273-80 (2001); Kim et al. Environ Health Perspect 112(6):666-71 (2004)).

Magnetic resonance spectroscopy (MRS) has been useful in the diagnoses of mitochondrial cytopathy by demonstrating elevations in cerebrospinal fluid (CSF) and cortical white matter lactate using proton MRS (1H-MRS) (Kaufmann et al., Neurology 62(8):1297-302 (2004)). Phosphorous MRS (31P-MRS) has been used to demonstrate low levels of cortical phosphocreatine (PCr) (Matthews et al., Ann. Neurol. 29(4):435-8 (1991)), and a delay in PCr recovery kinetics following exercise in skeletal muscle (Matthews et al., Ann. Neurol. 29(4):435-8 (1991); Barbiroli et al., J. Neurol. 242(7):472-7 (1995); Fabrizi et al., J. Neurol. Sci. 137(1):20-7 (1996)). A low skeletal muscle PCr has also been confirmed in patients with mitochondrial cytopathy by direct biochemical measurements.

Exercise testing is particularly helpful as an evaluation and screening tool in mitochondrial myopathies. One of the hallmark characteristics of mitochondrial myopathies is a reduction in maximal whole body oxygen consumption (VO2max) (Taivassalo et al., Brain 126(Pt 2):413-23 (2003)). Given that VO2max is determined by cardiac output (Qc) and peripheral oxygen extraction (arterial-venous total oxygen content) difference, some mitochondrial cytopathies affect cardiac function where delivery can be altered; however, most mitochondrial myopathies show a characteristic deficit in peripheral oxygen extraction (A-V O2 difference) and an enhanced oxygen delivery (hyperkinetic circulation) (Taivassalo et al., Brain 126(Pt 2):413-23 (2003)). This can be demonstrated by a lack of exercise induced deoxygenation of venous blood with direct AV balance measurements (Taivassalo et al., Ann. Neurol. 51(1):38-44 (2002)) and non-invasively by near infrared spectroscopy (Lynch et al., Muscle Nerve 25(5):664-73 (2002); van Beekvelt et al., Ann. Neurol. 46(4):667-70 (1999)).

Several of these energy biomarkers are discussed in more detail as follows. It should be emphasized that, while certain energy biomarkers are discussed and enumerated herein, the invention is not limited to modulation, normalization or enhancement of only these enumerated energy biomarkers.

Lactic acid (lactate) levels: Mitochondrial dysfunction typically results in abnormal levels of lactic acid, as pyruvate levels increase and pyruvate is converted to lactate to maintain capacity for glycolysis. Mitochondrial dysfunction can also result in abnormal levels of NADH+H+, NADPH+H+, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, such as the brain.

Measurement of cerebral lactic acidosis using magnetic resonance in MELAS patients is described in Kaufmann et al., Neurology 62(8):1297 (2004). Values of the levels of lactic acid in the lateral ventricles of the brain are presented for two mutations resulting in MELAS, A3243G and A8344G. Whole blood, plasma, and cerebrospinal fluid lactate levels can be measured by commercially available equipment such as the YSI 2300 STAT Plus Glucose & Lactate Analyzer (YSI Life Sciences, Ohio).

NAD, NADP, NADH and NADPH levels: Measurement of NAD, NADP, NADH (NADH+H+) or NADPH (NADPH+H+) can be measured by a variety of fluorescent, enzymatic, or electrochemical techniques, e.g., the electrochemical assay described in US 2005/0067303.

GSH, GSSG, Cys, and CySS levels: Briefly, plasma levels of GSH, GSSG, Cys, and CySS are used to calculate the in vivo $E_h$ values. Samples are collected using the procedure of Jones et al (2009 Free Radical Biology & Medicine 47(10) pp 1329-1338), and bromobimane is used to alkylate free thiols and HPLC and either electrochemical or MSMS to separate, detect, and quantify the molecules. As described in more detail in PCT Application No. PCT/US2013/058568, a method was developed for different experimental parameters to analyze the most common monothiols and disulfide (cystine, cysteine, reduced (GSH) and oxidized glutathione (GSSG)) present in human plasma, and using Bathophenanthroline disulfonic acid as the internal standard (IS). Complete separation of all the targets analytes and IS at 35° C. on a C18 RP column (250 mm×4.6 mm, 3 micron) was achieved using 0.2% TFA:Acetonitrile as a mobile phase pumped at the rate of 0.6 ml min−1 using electrochemical detector in DC mode at the detector potential of 1475 mV.

Oxygen consumption (vO2 or VO2), carbon dioxide output (vCO2 or VCO2), and respiratory quotient (VCO2/VO2): vO2 is usually measured either while resting (resting vO2) or at maximal exercise intensity (vO2 max). Optimally, both values will be measured. However, for severely disabled patients, measurement of vO2 max may be impractical. Measurement of both forms of vO2 is readily accomplished using standard equipment from a variety of vendors, e.g. Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, reduced Cytochrome C, and ratio of oxidized Cytochrome C to reduced Cytochrome C:Cytochrome C parameters, such as oxidized cytochrome C levels (Cyt $C_{ox}$), reduced cytochrome C levels (Cyt $C_{red}$), and the ratio of oxidized cytochrome C/reduced cytochrome C ratio (Cyt $C_{ox}$)/(Cyt $C_{red}$), can be measured by in vivo near infrared spectroscopy. See, e.g., Rolfe, P., "In vivo near-infrared spectroscopy," Annu. Rev. Biomed. Eng. 2:715-54 (2000) and Strangman et al., "Non-invasive neuroimaging using near-infrared light" Biol. Psychiatry 52:679-93 (2002).

Exercise tolerance/Exercise intolerance: Exercise intolerance is defined as "the reduced ability to perform activities that involve dynamic movement of large skeletal muscles because of symptoms of dyspnea or fatigue" (Piña et al., Circulation 107:1210 (2003)). Exercise intolerance is often accompanied by myoglobinuria, due to breakdown of muscle tissue and subsequent excretion of muscle myoglobin in the urine. Various measures of exercise intolerance can be used, such as time spent walking or running on a treadmill before exhaustion, time spent on an exercise bicycle (stationary bicycle) before exhaustion, and the like. Treatment with the compounds, compositions, or methods of the invention can result in about a 10% or greater improvement in exercise tolerance (for example, about a 10% or greater increase in time to exhaustion, e.g. from 10 minutes to 11 minutes), about a 20% or greater improvement in exercise tolerance, about a 30% or greater improvement in exercise tolerance, about a 40% or greater improvement in exercise tolerance, about a 50% or greater improvement in exercise tolerance, about a 75% or greater improvement in exercise tolerance, or about a 100% or greater improvement in exercise tolerance. While exercise tolerance is not, strictly speaking, an energy biomarker, for the purposes of the invention, modulation, normalization, or enhancement of energy biomarkers includes modulation, normalization, or enhancement of exercise tolerance.

Similarly, tests for normal and abnormal values of pyruvic acid (pyruvate) levels, lactate/pyruvate ratio, ATP levels, anaerobic threshold, reduced coenzyme Q ($CoQ_{red}$) levels, oxidized coenzyme Q ($CoQ_{ox}$) levels, total coenzyme Q ($CoQ_{tot}$) levels, oxidized cytochrome C levels, reduced cytochrome C levels, oxidized cytochrome C/reduced cytochrome C ratio, GSH and cysteine reduced, oxidized, total levels and ratio, acetoacetate levels, β-hydroxy butyrate levels, acetoacetate/β-hydroxy butyrate ratio, 8-hydroxy-2'-deoxyguanosine (8-OHdG) levels, and levels of reactive oxygen species are known in the art and can be used to evaluate efficacy of the compounds, compositions, and methods of the invention. (For the purposes of the invention, modulation, normalization, or enhancement of energy biomarkers includes modulation, normalization, or enhancement of anaerobic threshold.)

Table 8, following, illustrates the effect that various dysfunctions can have on biochemistry and energy biomarkers. It also indicates the physical effect (such as a disease symptom or other effect of the dysfunction) typically associated with a given dysfunction. It should be noted that any of the energy biomarkers listed in the table, in addition to energy biomarkers enumerated elsewhere, can also be modulated, enhanced, or normalized by the compounds, compositions, and methods of the invention. RQ=respiratory quotient; BMR=basal metabolic rate; HR (CO)=heart rate (cardiac output); T=body temperature (preferably measured as core temperature); AT=anaerobic threshold; pH=blood pH (venous and/or arterial).

TABLE 8

| Site of Dysfunction | Biochemical Event | Measurable Energy Biomarker | Physical Effect |
|---|---|---|---|
| Respiratory Chain | ↑ NADH | Δ lactate, Δ lactate: pyruvate ratio; and Δ acetoacetate: β-hydroxy butyrate ratio | Metabolic dyscrasia & fatigue |
| Respiratory Chain | ↓ H+ gradient | Δ ATP | Organ dependent dysfunction |
| Respiratory Chain | ↓ Electron flux | Δ VO2, RQ, BMR, ΔT, AT, pH | Metabolic dyscrasia & fatigue |
| Mitochondria & cytosol | ↓ ATP, ↓VO2 | Δ Work, AHR(CO) | Exercise intolerance |
| Mitochondria & cytosol | ↓ ATP | Δ PCr | Exercise intolerance |
| Respiratory Chain | ↓ Cyt CO$_{x/Red}$ | Δ λ ~700- 900 nm (Near Infrared Spectroscopy) | Exercise intolerance |
| Intermediary metabolism | ↓ Catabolism | Δ C14-Labeled substrates | Metabolic dyscrasia & fatigue |
| Respiratory Chain | ↓ Electron flux | Δ Mixed Venous VO2 | Metabolic dyscrasia & fatigue |
| Mitochondria & cytosol | ↑ Oxidative stress | Δ Tocopherol & Tocotrienols, CoQlO, docosahexaenoic acid | Uncertain |
| Mitochondria & cytosol | ↑ Oxidative stress | Δ Glutathionered | Uncertain |
| Mitochondria & cytosol | Nucleic acid oxidation | Δ8-hydroxy 2-deoxy guano sme | Uncertain |
| Mitochondria & cytosol | Lipid oxidation | Δ Isoprostane(s), eicosanoids | Uncertain |
| Cell membranes | Lipid oxidation | Δ Ethane (breath) | Uncertain |
| Cell membranes | Lipid oxidation | Δ Malondialdehyde | Uncertain |

Treatment of a subject afflicted by an oxidative stress disorder in accordance with the methods of the invention may result in the inducement of a reduction or alleviation of symptoms in the subject, e.g., to halt the further progression of the disorder.

Partial or complete suppression of the oxidative stress disorder can result in a lessening of the severity of one or more of the symptoms that the subject would otherwise experience. For example, partial suppression of MELAS could result in reduction in the number of stroke-like or seizure episodes suffered.

Any one or any combination of the energy biomarkers described herein provide conveniently measurable benchmarks by which to gauge the effectiveness of treatment or suppressive therapy. Additionally, other energy biomarkers are known to those skilled in the art and can be monitored to evaluate the efficacy of treatment or suppressive therapy.
Use of Compounds or Compositions for Modulation of Energy Biomarkers In addition to monitoring energy biomarkers to assess the status of treatment or suppression of oxidative stress diseases, the compounds or compositions of the invention can be used in subjects or patients to modulate one or more energy biomarkers. Modulation of energy biomarkers can be done to normalize energy biomarkers in a subject, or to enhance energy biomarkers in a subject.

Normalization of one or more energy biomarkers is defined as either restoring the level of one or more such energy biomarkers to normal or near-normal levels in a subject whose levels of one or more energy biomarkers show pathological differences from normal levels (i.e., levels in a healthy subject), or to change the levels of one or more energy biomarkers to alleviate pathological symptoms in a subject. Depending on the nature of the energy biomarker, such levels may show measured values either above or below a normal value. For example, a pathological lactate level is typically higher than the lactate level in a normal (i.e., healthy) person, and a decrease in the level may be desirable. A pathological ATP level is typically lower than the ATP level in a normal (i.e., healthy) person, and an increase in the level of ATP may be desirable. Accordingly, normalization of energy biomarkers can involve restoring the level of energy biomarkers to within about at least two standard deviations of normal in a subject, more preferably to within about at least one standard deviation of normal in a subject, to within about at least one-half standard deviation of normal, or to within about at least one-quarter standard deviation of normal.

Enhancement of the level of one or more energy biomarkers is defined as changing the extant levels of one or more energy biomarkers in a subject to a level which provides beneficial or desired effects for the subject. For example, a person undergoing strenuous effort or prolonged vigorous physical activity, such as mountain climbing, could benefit from increased ATP levels or decreased lactate levels. As described above, normalization of energy biomarkers may not achieve the optimum state for a subject with an oxidative stress disease, and such subjects can also benefit from enhancement of energy biomarkers. Examples of subjects who could benefit from enhanced levels of one or more energy biomarkers include, but are not limited to, subjects undergoing strenuous or prolonged physical activity, subjects with chronic energy problems, or subjects with chronic respiratory problems. Such subjects include, but are not limited to, pregnant females, particularly pregnant females in labor; neonates, particularly premature neonates; subjects exposed to extreme environments, such as hot environments (temperatures routinely exceeding about 85-86 degrees Fahrenheit or about 30 degrees Celsius for about 4 hours daily or more), cold environments (temperatures routinely below about 32 degrees Fahrenheit or about 0 degrees Celsius for about 4 hours daily or more), or environments with lower-than-average oxygen content, higher-than-average carbon dioxide content, or higher-than-average levels of air pollution (airline travelers, flight attendants, subjects at elevated altitudes, subjects living in cities with lower-than-average air quality, subjects working in enclosed environments where air quality is degraded); subjects with lung diseases or lower-than-average lung capacity, such as tubercular patients, lung cancer patients, emphysema patients, and cystic fibrosis patients; subjects recovering from surgery or illness; elderly subjects, including elderly subjects experiencing decreased energy; subjects suffering from chronic fatigue, including chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

Accordingly, when an increase in a level of one or more energy biomarkers is beneficial to a subject, enhancement of the one or more energy biomarkers can involve increasing the level of the respective energy biomarker or energy biomarkers to about at least one-quarter standard deviation above normal, about at least one-half standard deviation above normal, about at least one standard deviation above normal, or about at least two standard deviations above normal. Alternatively, the level of the one or more energy biomarkers can be increased by about at least 10% above the subject's level of the respective one or more energy biomarkers before enhancement, by about at least 20% above the subject's level of the respective one or more energy biomarkers before enhancement, by about at least 30% above the subject's level of the respective one or more energy biomarkers before enhancement, by about at least 40% above the subject's level of the respective one or more energy biomarkers before enhancement, by about at least 50% above the subject's level of the respective one or more energy biomarkers before enhancement, by about at least 75% above the subject's level of the respective one or more energy biomarkers before enhancement, or by about at least 100% above the subject's level of the respective one or more energy biomarkers before enhancement.

When a decrease in a level of one or more energy biomarkers is desired to enhance one or more energy biomarkers, the level of the one or more energy biomarkers can be decreased by an amount of about at least one-quarter standard deviation of normal in a subject, decreased by about at least one-half standard deviation of normal in a subject, decreased by about at least one standard deviation of normal in a subject, or decreased by about at least two standard deviations of normal in a subject. Alternatively, the level of the one or more energy biomarkers can be decreased by about at least 10% below the subject's level of the respective one or more energy biomarkers before enhancement, by about at least 20% below the subject's level of the respective one or more energy biomarkers before enhancement, by about at least 30% below the subject's level of the respective one or more energy biomarkers before enhancement, by about at least 40% below the subject's level of the respective one or more energy biomarkers before enhancement, by about at least 50% below the subject's level of the respective one or more energy biomarkers before enhancement, by about at least 75% below the subject's level of the respective one or more energy biomarkers before enhancement, or by about at least 90% below the subject's level of the respective one or more energy biomarkers before enhancement.

Use of Compounds or Compositions in Research Applications, Experimental Systems, and Assays The compounds or compositions of the invention can also be used in research applications. They can be used in in vitro, in vivo, or ex vivo experiments to modulate one or more energy biomarkers in an experimental system. Such experimental systems can be cell samples, tissue samples, cell components or mixtures of cell components, partial organs, whole organs, or organisms. Any one or more of the compounds or compositions can be used in experimental systems or research applications. Such research applications can include, but are not limited to, use as assay reagents, elucidation of biochemical pathways, or evaluation of the effects of other agents on the metabolic state of the experimental system in the presence/absence of one or more compounds or compositions of the invention.

Additionally, the compounds or compositions of the invention can be used in biochemical tests or assays. Such tests can include incubation of one or more compounds or compositions of the invention with a tissue or cell sample from a subject to evaluate a subject's potential response (or the response of a specific subset of subjects) to administration of said one or more compounds or compositions, or to determine which compound or composition of the invention produces the optimum effect in a specific subject or subset of subjects. One such test or assay would involve 1) obtaining a cell sample or tissue sample from a subject in which modulation of one or more energy biomarkers can be assayed; 2) administering one or more compounds or compositions of the invention to the cell sample or tissue sample; and 3) determining the amount of modulation of the one or more energy biomarkers after administration of the one or more compounds or compositions, compared to the status of the energy biomarker prior to administration of the one or more compounds or compositions. Another such test or assay would involve 1) obtaining a cell sample or tissue sample from a subject in which modulation of one or more energy biomarkers can be assayed; 2) administering at least two compounds or compositions of the invention to the cell sample or tissue sample; 3) determining the amount of modulation of the one or more energy biomarkers after administration of the at least two compounds or compositions, compared to the status of the energy biomarker prior to administration of the at least two compounds or compositions, and 4) selecting a compound or composition for use in treatment, suppression, or modulation based on the amount of modulation determined in step 3.

In certain embodiments, provided herein are methods for the use of a polymorph of Form I-VI for treating or protecting against injury or damage caused by radiation exposure and methods of using such compounds for treating or for protecting against injury or damage caused by radiation exposure. In certain embodiments, the methods for treating or for protecting against injury or damage caused by radiation exposure, comprise administering to a cell or cells, a tissue or tissues, or a subject in need thereof, a therapeutically effective amount or a prophylactically effective amount of a polymorph of Form I-VI or composition disclosed herein. In one embodiment, the polymorph of Form I-VI are used therapeutically during, after, or during and after radiation exposure. In another embodiment, a polymorph of Form I-VI are used prophylactically prior to radiation exposure. In another embodiment, a polymorph of Form I-VI is administered concurrently with radiation exposure. In another embodiment, the one or more compounds are administered after radiation exposure.

In certain embodiments, provided herein are methods for the use of a polymorph of Form I-VI for treating against injury or damage caused by radiation exposure and methods of using such compounds for treating or for protecting against injury or damage caused by radiation exposure. In certain embodiments, the methods for treating an injury or damage caused by radiation exposure, comprise administering to a cell or cells, a tissue or tissues, or a subject in need thereof, a therapeutically effective amount or a prophylactically effective amount of a polymorph of Form I-VI or composition disclosed herein. In one embodiment, the polymorph of Form I-VI are used therapeutically during, after, or during and after radiation exposure. In another embodiment, a polymorph of Form I-VI are used prophylactically prior to radiation exposure. In another embodiment, a polymorph of Form I-VI is administered concurrently with radiation exposure. In another embodiment, the one or more compounds are administered after radiation exposure.

Pharmaceutical Formulations

The compounds or compositions described herein can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

A pharmaceutical composition can comprise a unit dose formulation, where the unit dose is a dose sufficient to have a therapeutic or suppressive effect or an amount effective to modulate, normalize, or enhance an energy biomarker. The unit dose may be sufficient as a single dose to have a therapeutic or suppressive effect or an amount effective to modulate, normalize, or enhance an energy biomarker. Alternatively, the unit dose may be a dose administered periodically in a course of treatment or suppression of a disorder, or to modulate, normalize, or enhance an energy biomarker.

Pharmaceutical compositions containing the compounds or compositions of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds or compositions of the invention may be administered enterally, orally, parenterally, sublingually, by inhalation (e.g. as mists or sprays), rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds or compositions are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds or compositions can also be administered in liposome formulations. The compounds can also be administered as prodrugs, where the prodrug undergoes transformation in the treated subject to a form which is therapeutically effective. Additional methods of administration are known in the art.

In some embodiments of the invention, especially those embodiments where a formulation is used for injection or other parenteral administration including the routes listed herein, but also including embodiments used for oral, gastric, gastrointestinal, or enteric administration, the formulations and preparations used in the methods of the invention are sterile. Sterile pharmaceutical formulations are compounded or manufactured according to pharmaceutical-grade sterilization standards (United States Pharmacopeia Chapters 797, 1072, and 1211; California Business & Professions Code 4127.7; 16 California Code of Regulations 1751, 21 Code of Federal Regulations 211) known to those of skill in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds or compositions of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N.W., p. 33 et seq (1976).

The invention also provides articles of manufacture and kits containing materials useful for treating or suppressing oxidative stress disorders. The invention also provides kits comprising any one or more of the compounds or compositions as described herein. In some embodiments, the kit of the invention comprises a suitable container.

In other aspects, the kits may be used for any of the methods described herein, including, for example, to treat an individual with a mitochondrial disorder, or to suppress a mitochondrial disorder in an individual.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount or effective amount for a given situation can be readily determined by routine experimentation and is within the skill and judgment of the ordinary clinician.

Examples of dosages which can be used are a therapeutically effective amount or effective amount within the dosage range of about 0.1 mg/kg to about 300 mg/kg body weight, or within about 1.0 mg/kg to about 100 mg/kg body weight, or within about 1.0 mg/kg to about 50 mg/kg body weight, or within about 1.0 mg/kg to about 30 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Compounds or compositions of the present invention may be administered in a single daily dose, or the total daily dosage may be administered in divided dosage of two, three or four times daily.

While the compounds or compositions of the invention can be administered as the sole active pharmaceutical agent, they can also be used in combination with one or more other agents used in the treatment or suppression of disorders. Representative agents useful in combination with the compounds or compositions of the invention for the treatment or suppression of mitochondrial diseases include, but are not limited to, Coenzyme Q, vitamin E, idebenone, MitoQ, vitamins, NAC, and antioxidant compounds.

When additional active agents are used in combination with the compounds or compositions of the present invention, the additional active agents may generally be employed in therapeutic amounts as indicated in the Physicians' Desk Reference (PDR) 53rd Edition (1999), or such therapeutically useful amounts as would be known to one of ordinary skill in the art.

The compounds or compositions of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

The invention will be further understood by the following nonlimiting examples.

Preparation of Compositions of the Invention

The compositions of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Synthetic Reaction Parameters

Solvents employed in synthesis of the compounds and compositions of the invention include, for example, methanol ("MeOH"), acetone, water, acetonitrile, 1,4-dioxane, dimethylformamide ("DMF"), benzene, toluene, xylene, tetrahydrofuran ("THF"), chloroform, methylene chloride (or dichloromethane, ("DCM")), diethyl ether, pyridine, 2-methyl-tetrahydrofuran ("2-MeTHF"), dimethylacetamide ("DMA"), ethyl acetate ("EtOAc"), ethanol ("EtOH"), isopropyl alcohol ("IPA"), isopropyl acetate ("IPAc"), methyl cellulose ("MC"), acetonitrile ("MeCN"), methanol (MeOH), methyl tert-butyl ether ("MTBE"), phosphate buffered saline ("PBS"), tetrahydrofuran ("THF"), and the like, as well as mixtures thereof.

The term "q.s." means adding a quantity sufficient to achieve a stated function, e.g., to bring a solution to the desired volume (i.e., 100%).

The compounds and compositions herein are synthesized by an appropriate combination of generally well-known synthetic methods. Techniques useful in synthesizing the compounds and compositions herein are both readily apparent and accessible to those of skill in the relevant art in light of the teachings described herein. The discussion below is offered to illustrate certain of the diverse methods available for use in assembling the compounds and compositions herein. However, the discussion is not intended to define the scope of reactions or reaction sequences that are useful in preparing the compounds and compositions herein. 101871

Other methods for producing the compounds and compositions of the invention will be apparent to one skilled in the art in view of the teachings herein.

EXAMPLES

Example 1. Synthesis of (R)-2-hydroxy-2-methyl-4-(2,4,5-trimethyl-3,6-dioxocyclohexa-1,4-dienyl)butanamide (Form I)

Example 1A Extraction of (1 S, 2S)-(+)-Pseudoephedrine Free Base

To a suspension of (1S, 2S)-(+)-Pseudoephedrine hydrochloride salt (300 g, Spectrum) in 2-MeTHF (1.5 L, 5 vol) was added 20% Aq NaOH solution (750 mL, 2.5 vol) and the mixture was stirred for 30 min (some solids remained undissolved) and transferred to a separatory funnel. The lower aqueous layer was drained along with solids that remained at the interphase and back extracted with 2-MeTHF (750 mL, 2.5 vol), the undissolved solids completely dissolved to form two clear layers. The combined organic layers were evaporated to dryness on rotavapor and the solids obtained were dried in a vacuum oven at 50° C. overnight to afford 240.3 g of free base as a white solid (97.7% recovery).

Example 1B. Precipitation of (1S,2S)-Pseudoephedrine from 2-MeTHF/heptane (1S,2S)-pseudoephedrine (Sigma-Aldrich, sku #212464, 8.2 g) was dissolved at 50° C. in 2-MeTHF (41 ml, 5 vol). The resulting solution was diluted with heptane (82 ml, 10 vol) and the resulting suspension was stirred at room temperature overnight. The crystallized (1S,2S)-pseudoephedrine was filtered off and dried overnight at 40° under vacuum affording 6.4 g (78%) of white crystalline material. Filtrate was discarded to general waste.

Relatively low (78%) crystallization yield prompted an additional crystallization experiment with higher heptane to 2-MeTHF ratio. Crystalline (1S,2S)-pseudoephedrine obtained in the experiment above was dissolved at 50° C. in 2-MeTHF (32 ml, 5 vol). The resulting solution was diluted with heptane (32 ml, 5 vol) and the resulting suspension was chased with heptane (3×50 ml) on rotary evaporator until molar ration of 2-MeTHF to heptane became lower than 6% by NMR. The resulting suspension was filtered off and the product dried overnight at 40° under vacuum affording 6.3 g (98%) of white crystalline material.

Example 1C. Chiral Resolution of Trolox Using (1S, 2S)-(+)-Pseudoephedrine

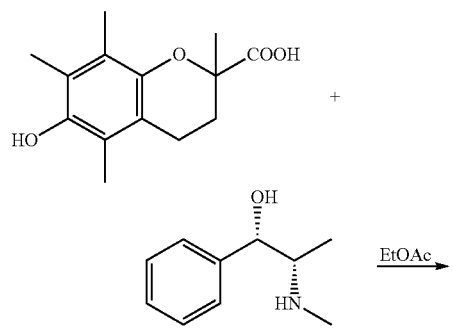

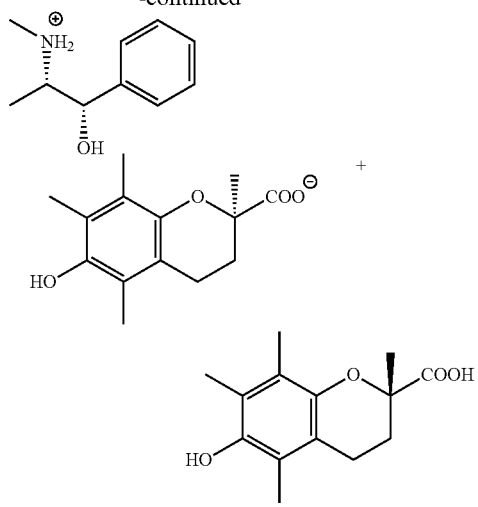

Racemic Trolox (316.6 g, 1.27 mol) and (1S, 2S)-(+)-Pseudoephedrine free base described in Example 1A (240.0 g, 1.46 mol) were charged to a 4 L jacketed reactor equipped with an overhead stirrer, temperature probe and a nitrogen purge. Ethyl acetate (EtOAc, 1585 mL, 5 vol) was charged and the slurry was heated to 50° C. resulting in clear solution. (Premature (prior to complete dissolution of rac-trolox) precipitation of the (R)-trolox-pseudoephedrine salt was occasionally observed at 40°. If premature precipitation takes place the reaction mixture was heated (usually to reflux temperature) to achieve complete dissolution.) The reaction mixture was cooled overnight to room temperature at which time massive precipitation was observed. The mixture was cooled to 10° C. over 30 min and held at this temperature for 1 h. The solids formed were collected by filtration, the wet cake was washed with EtOAc (1.9 L, 6 Vol) and the filter cake was dried in a vacuum oven at 25-30° C. to constant weight to afford 188.1 g (71.3% based on (R)-trolox) of a white solid. Chiral HPLC data indicated nearly 100% enantiomeric purity.

Example 1D. Recovery of (R)-Trolox from its Salt with (1S, 2S)-(+)-Pseudoephedrine

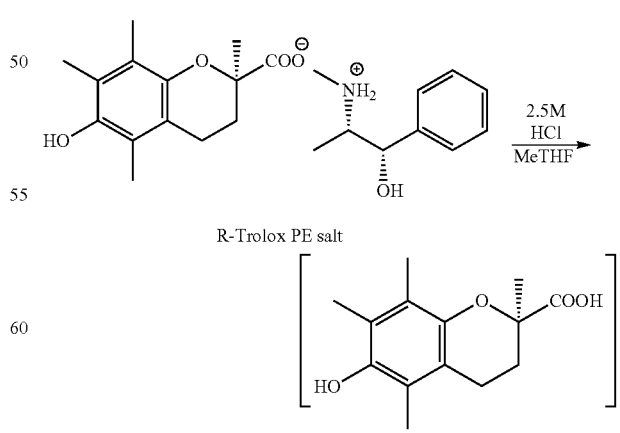

R-Trolox PE salt

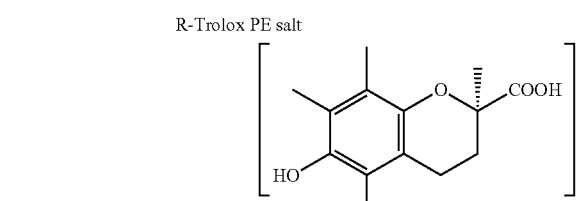

The resulting (R)-Trolox PE salt (187.3 g, 0.45 mol) was charged to a 2 L round-bottom flask followed by 2-MeTHF (570 ml, 3 vol.) to form a slurry. Hydrochloric acid (2.5 M, 325 ml, 0.81 mol, 1.75 eq) was added portionwise while maintaining temperature below 25° C. The trolox-PE salt was dissolved and (R)-Trolox was extracted into organic phase. Small black rag was observed in the interface and was kept with the aqueous. The aqueous phase was additionally extracted with 2-MeTHF (2×200 ml). The combined organic layer was then washed with 15% NaCl (200 ml) followed by water (200 ml). The organic layer was dried over anhydrous sodium sulfate (150 g), filtered and evaporated to dryness to afford white solid which was dried under vacuum oven at 30° C. to constant weight of 128.3 g, which is an overstoichiometric amount.

Example 1E. Preparation of (R)-6-hydroxy-2,5,7,8-tetramethylchromane-2-carboxamide

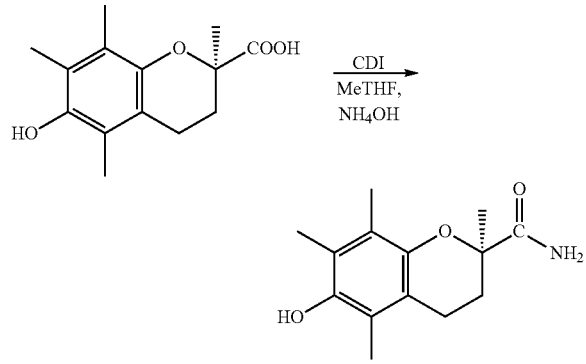

CDI (Sigma-Aldrich) (188 g, 1.16 mol) was charged to a 3-neck 2 L RBF equipped with an overhead stirrer, nitrogen inlet and temperature probe. 2-MeTHF (290 mL) was added to give a stirrable slurry followed by slow addition of (R)-trolox (126.0 g, 504 mmol) in 2-MeTHF (500 ml) at below 30° C. A slightly exothermic reaction accompanied by $CO_2$ evolution was observed. Outgassing started after addition of approximately one third of (R)-trolox. Complete dissolution of the starting materials was observed in approximately 15 min.

The content of this flask was slowly added to a pre-cooled to 5° C. 28-30% aqueous ammonia (380 ml) maintaining temperature below 30° C. The resulting biphasic suspension was stirred at room temperature and monitored by HPLC. The reaction was found to be complete at 36 h and was further processed after 48 h.

The reaction mixture was acidified to pH 1-2 with sulfuric acid (1:4 v/v) (850 ml) maintaining the temperature ≤28° C., reaction was highly exothermic. The aqueous layer (pH=1) was removed and the organic layer was washed with NaCl (15% aqueous w/v, 250 mL), $NaHCO_3$ (1 M, 250 mL), NaCl (15% aqueous w/v, 250 mL) and water (250 ml). The majority of the organic layer was used for the subsequent steps.

Example 1F. Preparation of (R)-2-hydroxy-2-methyl-4-(2,4,5-trimethyl-3,6-dioxocyclohexa-1,4-dienyl)butanamide

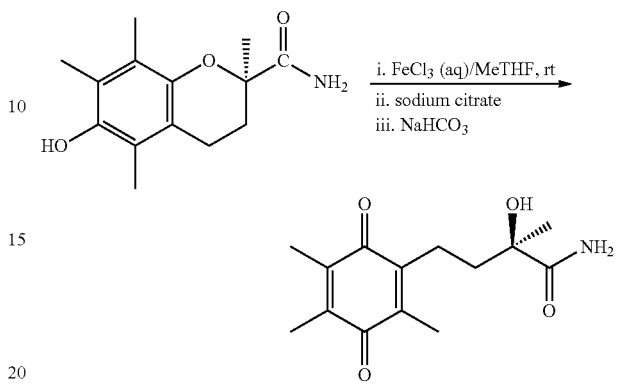

A solution of (R)-6-hydroxy-2,5,7,8-tetramethylchromane-2-carboxamide (708 ml) which contains ~0.39 mole of the intermediate amide and water (126 ml) were charged to a 2 L 3N RBF equipped with an overhead stirrer and a thermocouple.

A stock solution of $FeCl_3 \times 6H_2O$ (480 g, 1.78 mol) in water (336 ml) was divided into 4 equal parts (204 g each) and one-fourth of the iron(III) chloride solution was added to the reaction flask. A weak (~3° C.) exotherm was observed, the color of the organic layer turned nearly black then lightened to dark-brown. The biphasic reaction mixture was vigorously stirred for 40 min at room temperature. After removal of the lightly colored aqueous phase another portion of the iron(III) chloride solution was added and stirred for 40 min. The operation was repeated one more time and the organic phase was stored overnight at room temperature. The fourth treatment with $FeCl_3 \times 6H_2O$ was performed next morning. Nearly complete (99.44%) conversion of (R)-6-hydroxy-2,5,7,8-tetramethylchromane-2-carboxamide to (R)-2-hydroxy-2-methyl-4-(2,4,5-trimethyl-3,6-dioxocyclohexa-1,4-dienyl)butanamide was observed. Initial iron extraction was performed with 1M trisodium citrate solution (2×350 ml); the AUC % of (R)-6-hydroxy-2,5,7,8-tetramethylchromane-2-carboxamide increased to 0.84%. pH of the organic phase remained highly acidic (pH=1). A 1 ml aliquot of the organic phase was treated with 1M $NaHCO_3$ resulting in massive precipitation of red $Fe(OH)_3$. Based on this observation one more trisodium citrate wash (175 ml) was performed (0.74% (R)-6-hydroxy-2,5,7,8-tetramethylchromane-2-carboxamide). The repeat testing of the 1 ml aliquot with 1M $NaHCO_3$ gave no precipitation in the aqueous layer and the color of the aqueous layer was yellow, not red, indicating complete or nearly complete iron removal.

The organic layer was heated to 40° C. to prevent premature precipitation of (R)-2-hydroxy-2-methyl-4-(2,4,5-trimethyl-3,6-dioxocyclohexa-1,4-dienyl)butanamide and washed with 1M sodium bicarbonate solution (175 ml). The phase split was not immediate but was complete in 15 min forming two clear yellow layers. The organic layer (0.30% (R)-6-hydroxy-2,5,7,8-tetramethylchromane-2-carboxamide) was additionally washed with water (350 ml) giving 0.22% (R)-6-hydroxy-2,5,7,8-tetramethylchromane-2-carboxamide. Evaporation of the organic layer gave 96 g of (R)-2-hydroxy-2-methyl-4-(2,4,5-trimethyl-3,6-dioxocyclohexa-1,4-dienyl)butanamide.

The combined bicarbonate/water layers were back extracted with 2×250 ml of 2-MeTHF. Evaporation of these extracts separately gave 4.0 and 0.9 g of (R)-2-hydroxy-2-methyl-4-(2,4,5-trimethyl-3,6-dioxocyclohexa-1,4-dienyl)butanamide.

The combined solids (100.9 g—crude (R)-2-hydroxy-2-methyl-4-(2,4,5-trimethyl-3,6-dioxocyclohexa-1,4-dienyl)butanamide, 84% yield based on (R)-trolox-pseudoephedrine salt) were dissolved in isopropanol (600 ml) at 70° C. and the resulting yellow solution was charged to a 2 L 3N RBF equipped with an overhead stirrer a heating mantle and a thermocouple.

Heptane (600 ml) was added, no precipitation was observed. The reaction mixture was reheated to 55° C. and slowly cooled down to room temperature. Seeds of the desired polymorph (0.2 g) were added and the reaction mixture was stirred overnight at room temperature. Massive precipitation was observed overnight. The reaction mixture was cooled to 7° C. and stirred for additional 8 hours. The product was filtered, washed with isopropanol-heptane 1:1 v/v (2×75 ml) and dried over the weekend at 40° C. Yield 69.4 g of (R)-2-hydroxy-2-methyl-4-(2,4,5-trimethyl-3,6-dioxocyclohexa-1,4-dienyl)butanamide (58% based on (R)-trolox—pseudoephedrine salt). XRPD data for the product corresponded to the desired Form I.

Example 2. Solubility Measurement of Pattern A (R)-Trolox was produced from racemic Trolox via methylbenzyl amine double resolution in a manner similar to that described in Example 29 of U.S. Pat. No. 4,026,907. This (R)-Trolox was used to synthesize the (R)-2-hydroxy-2-methyl-4-(2,4,5-trimethyl-3,6-dioxocyclohexa-1,4-dienyl)butanamide starting material. This starting material, designated as Pattern A, was used for the solubility measurement.

Excess amount of solid was slurried in 17 solvent systems having diverse properties for minimum of 3 days. The slurry was centrifuged and the clear solution was used for gravimetric method. The compound showed elevated solubility in MeOH, EtOH at ambient temperature, and IPA, acetone, MeOH, EtOH and 2-MeTHF at 50° C. Moderate solubility was observed in EtOAc, THF, IPA, acetone, 2-MeTHF, MeCN, 0.5% Methyl Cellulose/2% Tween 80, IPAc and 4% DMA in PBS at ambient and 50° C. Limited solubility was observed from heptane, toluene, MTBE, water and 0.5% Methyl Cellulose in water at ambient and elevated temperatures. Table 9 presents the measured solubility data. A ±10% error is expected.

TABLE 9

Solubility of (R)-2-hydroxy-2-methyl-4-(2,4,5-trimethyl-3,6-dioxocyclohexa-1,4-dienyl)butanamide in various solvent systems (Starting material, Pattern A used)

| Solvent | mg/mL at 25° C. | mg/mL at 50° C. |
|---|---|---|
| Heptane | 6 | 6 |
| Toluene | 3 | <18 |
| MTBE | 10 | 16 |
| EtOAc | 22 | 38 |
| THF | 28. | 33 |
| IPA | 20 | 53 |
| Acetone | 39 | 90 |
| EtOH | 40 | >121 |
| MeOH | >101 | >112 |
| 2-MeTHF | 35 | 59 |
| MeCN | 20 | 38 |
| Water | 3 | 3 |

TABLE 9-continued

Solubility of (R)-2-hydroxy-2-methyl-4-(2,4,5-trimethyl-3,6-dioxocyclohexa-1,4-dienyl)butanamide in various solvent systems (Starting material, Pattern A used)

| Solvent | mg/mL at 25° C. | mg/mL at 50° C. |
|---|---|---|
| [1]Water | 2 | 6 |
| 0.5% MC/2% Tween 80* | 26 | 30 |
| IPAc | 13 | 16 |
| 0.5% MC in Water* | 7 | 4 |
| 4% DMA in PBS* | 10 | 13 |

* Part of the concentration relates to solvent constituents

As shown in Table 9, Pattern A is soluble in a variety of polar and non-polar solvents, and in addition has increased solubility in a simple detergent (0.5% MC/2% Tween 80).

Example 3. Short Term Slurry Experiments

Short term slurry experiments of the starting material, Pattern A, were performed for a minimum of 3 days in 17 different solvent systems having diverse properties at two different temperatures (25 and 50° C.). A 48 position Chemglass reaction block was used for heating and stirring the slurries which were in 2 mL HPLC vials. After the due time, vials were centrifuged and the wet solids were used for X-ray diffraction. Table 10 shows the results of the slurry experiments. These results demonstrate that Pattern A solid was relatively stable if slurried in most of these solvents for a short period of time. However, slurring Pattern A solid in THF and 0.5% Methyl Cellulose/2° 4) Tween 80 resulted in two new X-ray patterns designated as Patterns B and C respectively (FIG. 1).

TABLE 10

Summary of a minimum 3 days slurry of (R)-2-hydroxy-2-methyl-4-(2,4,5-trimethyl-3,6-dioxocyclohexa-1,4-dienyl)butanamide (Starting material, Pattern A used)

| Solvent | Starting Form | 25° C. Resulting Form, Wet | 25° C. Resulting Form, Dry | 50 °C Resulting Form, Wet |
|---|---|---|---|---|
| Heptane | A | A | | A |
| Toluene | A | A | | A |
| MTBE | A | A | | A |
| EtOAc | A | A | | A |
| THF | A | B | B | — |
| IPA | A | A | | A |
| Acetone | A | A | | A |
| EtOH | A | A | | — |
| MeOH | A | — | | — |
| 2-MeTHF | A | A | | A |
| MeCN | A | A | | A |
| Water | A | A | | A |
| [1]Water | A | A | | A |
| 0.5% MC/2% Tween 80 | A | C | C | A |
| IPAc | A | A | | A |
| 0.5% MC in Water | A | A | | A |
| 4% DMA in PBS | A | A | | A |

Example 4. Evaporative Crystallization Experiments

Figure 2:
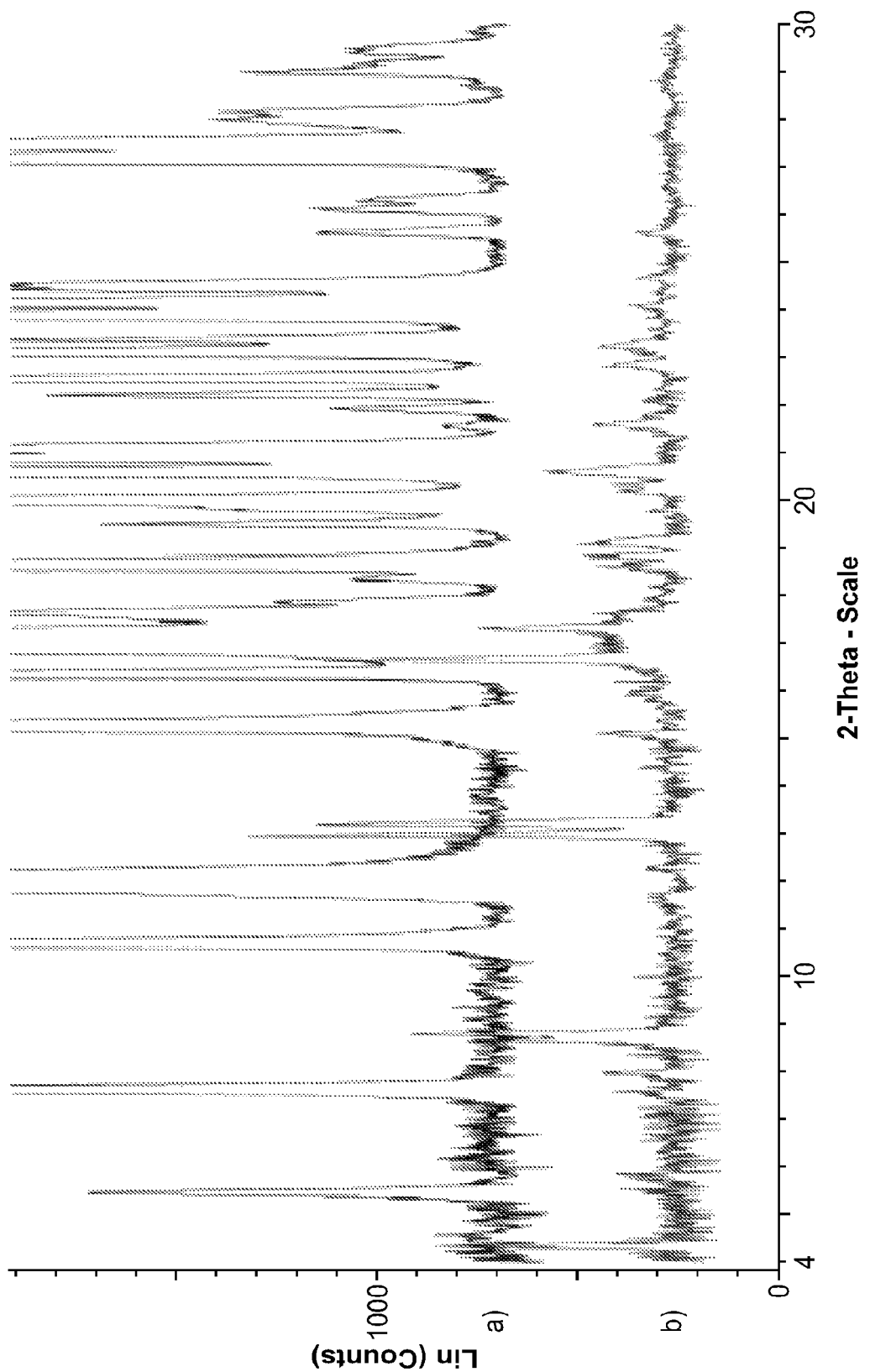
FIG. 2 shows a XRPD overlay of (R)-2-hydroxy-2-methyl-4-(2,4,5-trimethyl-3,6-dioxocyclohexa-1,4-dienyl)butanamide sample lots, a) starting material, Pattern A, and b) Pattern D following evaporative crystallization from 2-methyltetrahydrofuran (2-MeTHF).

Evaporative crystallization experiments of (R)-2-hydroxy-2-methyl-4-(2,4,5-trimethyl-3,6-dioxocyclohexa-1,4- dienyl)butanamide were performed using the samples generated during the gravimetric solubility determination (Example 2). XRPD analysis of most samples afforded Pattern A. However XRPD analysis of solids isolated from 2-MeTHF at 25° C. was found to afford a unique crystalline pattern, designated Pattern D as shown in FIG. 2. XRPD analysis of samples from IPAc, 0.5% MC in water and 4% DMA in PBS mostly yielded amorphous patterns with the exception of IPAc at 50° C. which afforded a crystalline pattern consistent with Pattern A. All results are summarized in Table 11.

TABLE 11

Summary of evaporative crystallization experiments of (R)-2-hydroxy-2-methyl-4-(2,4,5-trimethyl-3,6-dioxocyclohexa-1,4-dienyl)butanamide (Starting material, Pattern A used)

|  | | 25 ° C. | | 50° C. |
|---|---|---|---|---|
|  | Starting Form | Resulting Form, Wet | Resulting Form, Dry | Resulting Form, Wet |
| Heptane | A | — | | — |
| Toluene | A | A | | A |
| MTBE | A | Oil | | Amorphous |
| EtOAc | A | A | | A |
| THF | A | Amorphous | | A |
| IPA | A | Amorphous | | Amorphous |
| Acetone | A | A | | A |
| EtOH | A | A | | A |
| MeOH | A | A | | A |
| 2-MeTHF | A | D | NA | A |
| MeCN | A | A | | A |
| Water | A | A | | A |
| [1]Water | A | A | | A |
| 0.5% MC/2% Tween 80 | A | Oil | | Oil |
| IPAc | A | Amorphous | | A |
| 0.5% MC in Water | A | Amorphous | | — |
| 4% DMA in PBS | A | Amorphous | | Amorphous |

NA- Drying not performed due to sample dried overnight

Example 5. Crystallization Experiments

Fast and slow cooling single solvent crystallization experiments were performed in Toluene, EtOAc, IPA, acetone, EtOH, 2-MeTHF, and IPA with 2% water (Table 12). A 48 position Chemglass reaction block was used for heating and stirring which were performed in 4 mL vials. Each vial was charged with 50-80 mg of starting material (Pattern A) fitted with a magnetic stir bar. Primary solvent was added and heated with stirring until dissolution achieved. Once fully dissolved the sample was slow cooled by radiative cooling or crashed cooled with use of an ice bath followed over night equilibration with stirring. For Binary solvent crystallizations, anti-solvent (Heptane) was added in two methods (Table 13). In method one, the anti-solvent was added drop wise to the sample solution until slight precipitation was observed. Method two used a reverse addition of the sample solution to a heated anti-solvent in a 2:1 ratio before being allowed to cool. Samples which afforded solids after overnight equilibration were isolated by filtration and samples that did not precipitate were evaporated under a gentle stream of nitrogen. All samples were dried overnight in a vacuum oven at ambient conditions and analyzed by XRPD to check for form change. All experimental details and results are summarized in Tables 12-13.

Figure 3:
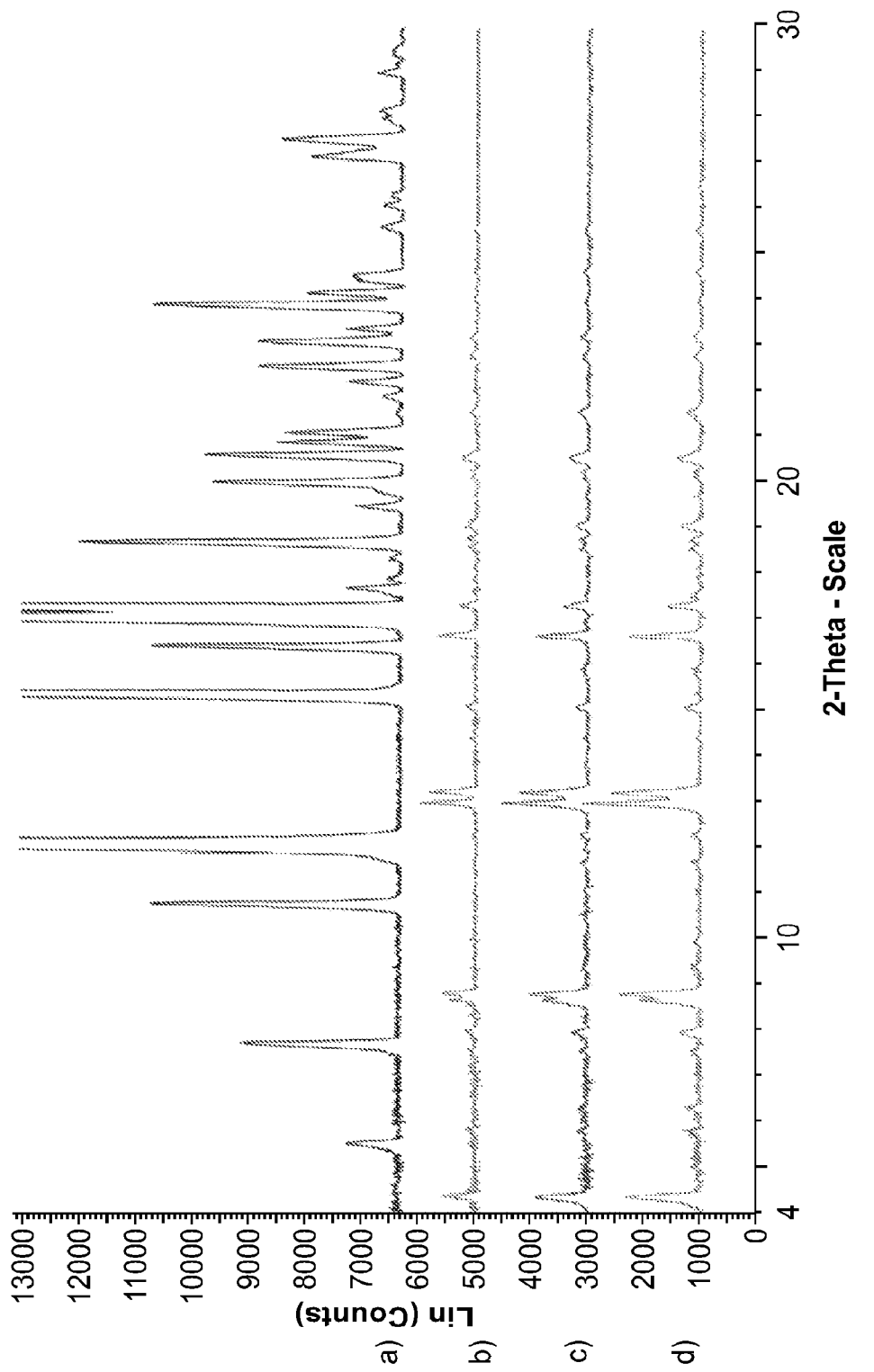
FIG. 3 shows a XRPD overlay of (R)-2-hydroxy-2-methyl-4-(2,4,5-trimethyl-3,6-dioxocyclohexa-1,4-dienyl)butanamide crystallization experiments, a) starting material, Pattern A, b) Pattern D following evaporative crystallization from 2-MeTHF (Example 4), c) from evaporative crystallization in 2-MeTHF (Example 5, fast cooling), and d) from evaporative crystallization in 2-MeTHF (Example 5, slow cooling).
Figure 4:
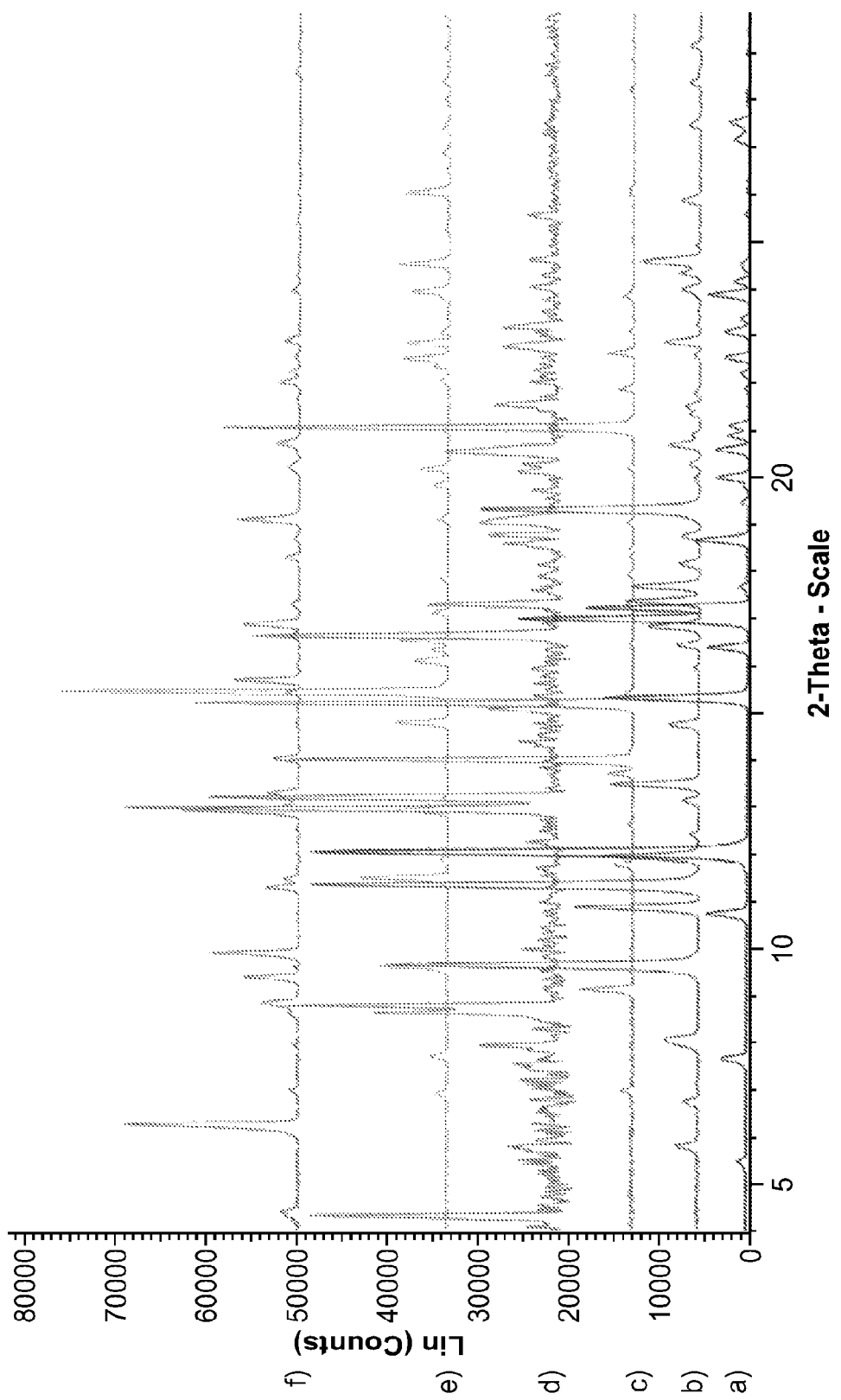
FIG. 4 shows a XRPD stack plot of all (R)-2-hydroxy-2-methyl-4-(2,4,5-trimethyl-3,6-dioxocyclohexa-1,4-dienyl)butanamide forms, a) starting material, Pattern A, b) Pattern B, c) Pattern C, d) Pattern D, e) Pattern E from fast cooling crystallization in ethyl acetate (EtOAc), and f) Pattern F, from fast cooling crystallization in 2-MeTHF.

XRPD analysis of all isolated solids mostly afforded crystalline patterns consistent with the starting material, Pattern A. However, single solvent crystallizations performed in 2-MeTHF with fast and slow cooling profiles, were not observed to afford solids upon cooling and were evaporated to dryness under nitrogen. These evaporated solids were found to afford XRPD patterns consistent with previously observed Pattern D (FIG. 3). Fast cooling crystallization performed in EtOAc, yielded unique crystalline solids by XRPD which were compared to all known forms and designated as Pattern E (FIG. 4). Binary solvent crystallizations with fast and slow cooling profiles performed in EtOH/Heptane and Acetone/Heptane afforded XRPD patterns consistent with Pattern A.

TABLE 12

Summary of single solvent crystallization experiments of (R)-2-hydroxy-2-methyl-4-(2,4,5-trimethyl-3,6-dioxocyclohexa-1,4-dienyl)butanamide (Starting material, Pattern A used)

| Starting Material (Pattern A) (mg) | Primary Solvent | | | | | |
|---|---|---|---|---|---|---|
| | Solvent | Vol (mL) | Temp (° C.) | Cooling Rate | Isolation | XRPD [Pattern] |
| 49.7 | Toluene | 2.75 | 60 | Fast | NA | — |
| 52.3 | EtOAc | 1 | 60 | Fast | Filter | Crystalline [Pattern E] |
| 55.9 | IPA | 1 | 60 | Fast | Filter | Crystalline [Pattern A] |
| 50.9 | Acetone | 0.5 | 60 | Fast | Filter | Crystalline [Pattern A] |
| 82.0 | EtOH | 0.5 | 60 | Fast | Filter | Crystalline [Pattern A] |
| 51.1 | 2-MeTHF | 1 | 60 | Fast | Evap | Crystalline [Pattern D] |
| 48.9 | IPA with 2% water | 0.5 | 60 | Fast | Filter | Crystalline [Pattern A] |
| 50.2 | Toluene | 2.75 | 60 | Slow | NA | — |
| 49.2 | EtOAc | 1 | 60 | Slow | Filter | Crystalline [Pattern A] |
| 54.9 | TPA | 1 | 60 | Slow | Filter | Crystalline [Pattern A] |
| 51.9 | Acetone | 0.5 | 60 | Slow | Filter | Crystalline [Pattern A] |
| 82.7 | EtOH | 0.5 | 60 | Slow | Filter | Crystalline [Pattern A] |
| 54.6 | 2-MeTHF | 1 | 60 | Slow | Evap | Crystalline [Pattern D] |
| 54 | IPA with 2% water | 0.5 | 60 | Slow | Filter | Crystalline [Pattern A] |

TABLE 13

Summary of binary solvent crystallization experiments of (R)-2-hydroxy-2-methyl-4-
(2,4,5-trimethyl-3,6-dioxocyclohexa-1,4-dienyl)butanamide (Starting material, Pattern A used)

| Starting Material (Pattern A) (mg) | Primary Solvent | | | Anti-Solvent | | Rate of Anti-Solvent Addition | Isolation | XRPD [Pattern] |
|---|---|---|---|---|---|---|---|---|
| | Solvent | Vol (mL) | Temp (° C.) | Solvent | Vol (mL) | | | |
| 84.5 | EtOH | 0.5 | 60 | Heptane | 2.5 | Slow | Filter | Crystalline [Pattern A] |
| 53.7 | Acetone | 0.5 | 60 | Heptane | 1.5 | Slow | Filter | Crystalline [Pattern A] |
| 82.2 | EtOH | 0.5 | 60 | Heptane | 1.0 | Fast | Filter | Crystalline [Pattern A] |
| 56.1 | Acetone | 0.5 | 60 | Heptane | 1.0 | Fast | Filter | Crystalline [Pattern A] |

Example 6. Scale-Up Experiments

Scale-up experiments were performed on a 300 mg scale by single solvent fast cooling crystallizations in 2-MeTHF, EtOAc, and slurries in THF and 0.5% Methyl Cellulose/2% Tween 80 in an attempt to isolate previously observed Patterns D, E, B and C respectively for further characterization. Experimental details and results are summarized in Tables 14-15.

Figure 5:
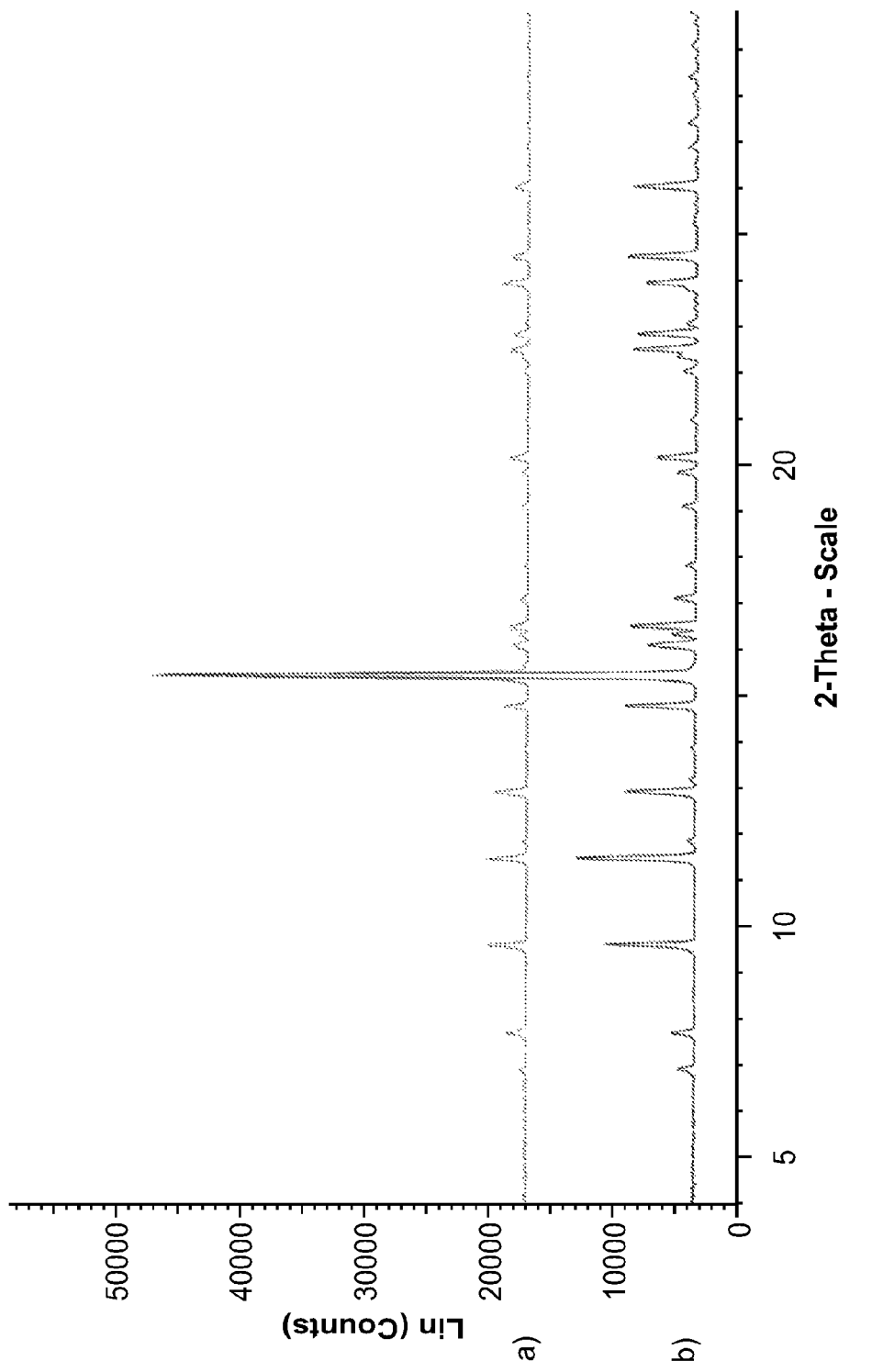
FIG. 5 shows a XRPD stack plot of (R)-2-hydroxy-2-methyl-4-(2,4,5-trimethyl-3,6-dioxocyclohexa-1,4-dienyl)butanamide forms, a) Pattern E from fast cooling crystallization in EtOAc (Example 5), and b) from scale-up fast cooling crystallization in EtOAc (Example 6).
Figure 6:
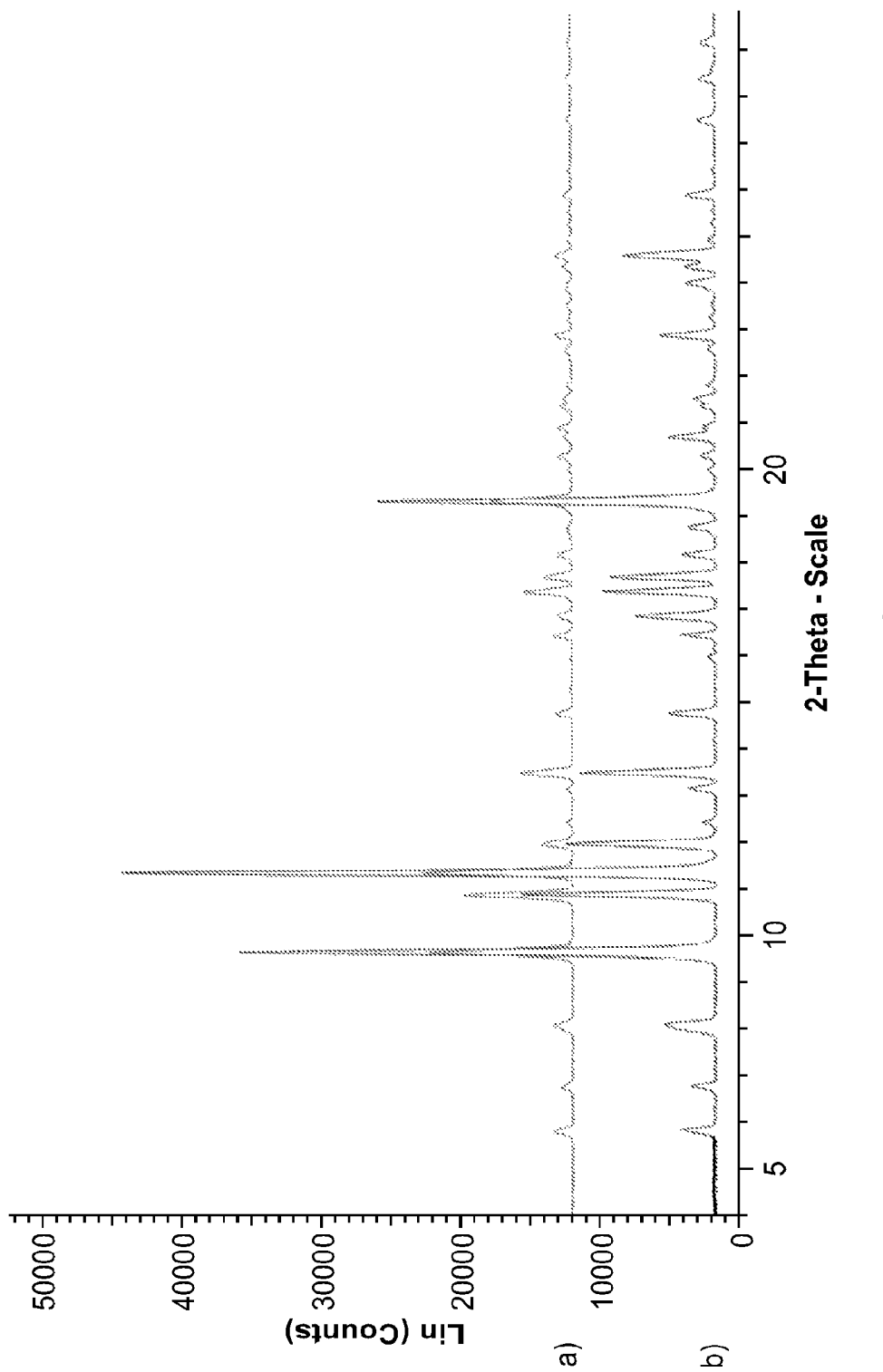
FIG. 6 shows a XRPD stack plot of (R)-2-hydroxy-2-methyl-4-(2,4,5-trimethyl-3,6-dioxocyclohexa-1,4-dienyl)butanamide forms, a) Pattern B from slurry in THF (Example 3), and b) from scale-up slurry in Tiff (Example 6).
Figure 7:
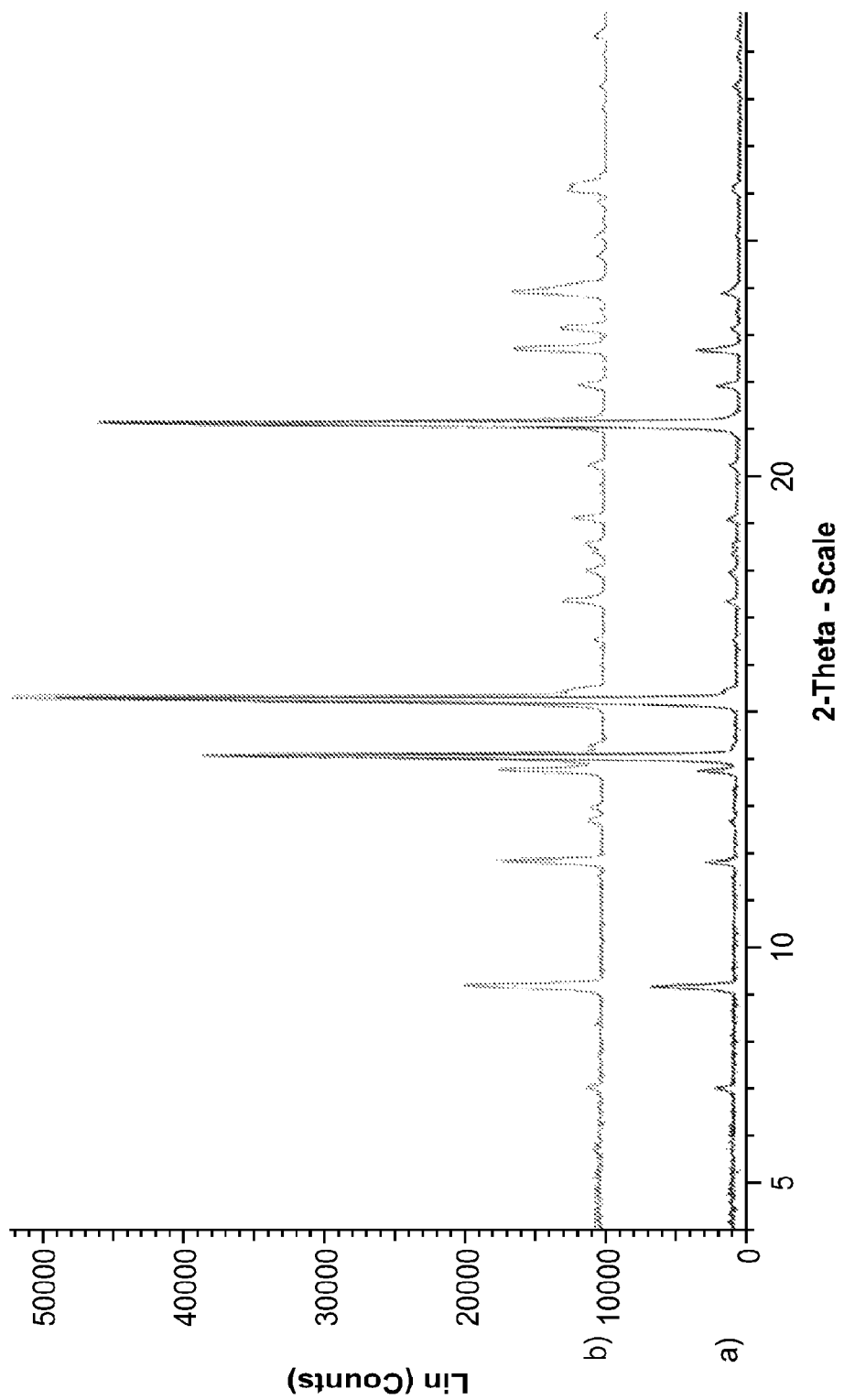
FIG. 7 shows a XRPD stack plot of (R)-2-hydroxy-2-methyl-4-(2,4,5-trimethyl-3,6-dioxocyclohexa-1,4-dienyl)butanamide forms, a) Pattern C from slurry in 0.5% Methyl Cellulose/2% Tween 80 (Example 3), and b) from scale-up slurry in 0.5% Methyl Cellulose/2% Tween 80 (Example 6).

XRPD analysis of solids isolated from single solvent crystallizations performed in 2-MeTHF with fast and cooling profiles, afforded a unique XRPD pattern, designated as Pattern F (FIG. 4). Fast cooling crystallization performed in EtOAc yielded crystalline solids consistent with Pattern E by XRPD (FIG. 5). Slurry experiments performed in THF and 0.5% Methyl Cellulose/2% Tween 80, were found to afford Patterns B and C respectively following 24 hours of equilibration (FIG. 6-7).

TABLE 14

Summary of single solvent crystallization scale-up experiments of (R)-2-
hydroxy-2-methyl-4-(2,4,5-trimethyl-3,6-dioxocyclohexa-1,4-dienyl)butanamide.

| Starting material (Pattern A) (mg) | Primary Solvent | | | Cooling Rate | Seeding upon cooling [mg] | Isolation | XRPD [Pattern] |
|---|---|---|---|---|---|---|---|
| | Solvent | Vol (mL) | Temp (° C.) | | | | |
| 312.0 | 2-MeTHF | 6.0 | 60 | Fast | [~10] | Evap | Crystalline [Pattern F] |
| 300.7 | EtOAc | 6.0 | 60 | Fast | [~10] | Filter | Crystalline [Pattern E] |

Fast cooling single solvent crystallization experiments were performed in 2-MeTHF and EtOAc (Table 14). A 48 position Chemglass reaction block was used for heating and stirring which were performed in 4 mL vials. Each vial was charged with approximately 300 mg of starting material fitted with a magnetic stir bar. 6 mL of primary solvent was added and heated to 60° C. with stirring until dissolution achieved. Once fully dissolved the sample was (crashed cooled) transferred to an ice bath and seeded with a spatula tip full of Pattern D or E, followed by overnight equilibration at room temperature with stirring. Samples which afforded solids after overnight equilibration were isolated by filtration and samples that did not precipitate were evaporated under a gentle stream of nitrogen. All samples were dried overnight under vacuum at ambient conditions and XRPD analysis was performed to check for form change.

Slurry experiments were performed in THF and 0.5% Methyl Cellulose/2% Tween 80 (Table 15). A 48 position Chemglass reaction block was used for heating and stirring which were performed in 4 mL vials. Each vial was charged with approximately 300 mg of starting material fitted with a magnetic stir bar. Slurry solvent was added up to 2 mL at ambient conditions and allowed to equilibrate for 30 minutes before adding a spatula tip full of Pattern B or C.

TABLE 15

Summary of slurry scale-up experiments of (R)-2-hydroxy-2-methyl-
4-(2,4,5-trimethyl-3,6-dioxocyclohexa-1,4-dienyl)butanamide.

| Starting material (Pattern A) (mg) | Primary Solvent | | | Slurry Temp. (° C.) | Slurry Formation | Seeding upon Slurry [mg] | XRPD [Pattern] 24 hr |
|---|---|---|---|---|---|---|---|
| | Solvent | Vol (mL) | | | | | |
| 305.7 | THF | 2 | | Ambient | Yes | [~10] | Crystalline [Pattern B] |
| 308.3 | 0.5% MC/2% Tween 80 in water | 2 | | Ambient | Yes | [~10] | Crystalline [Pattern C] |

Example 7. Competitive Slurries

Figure 8:
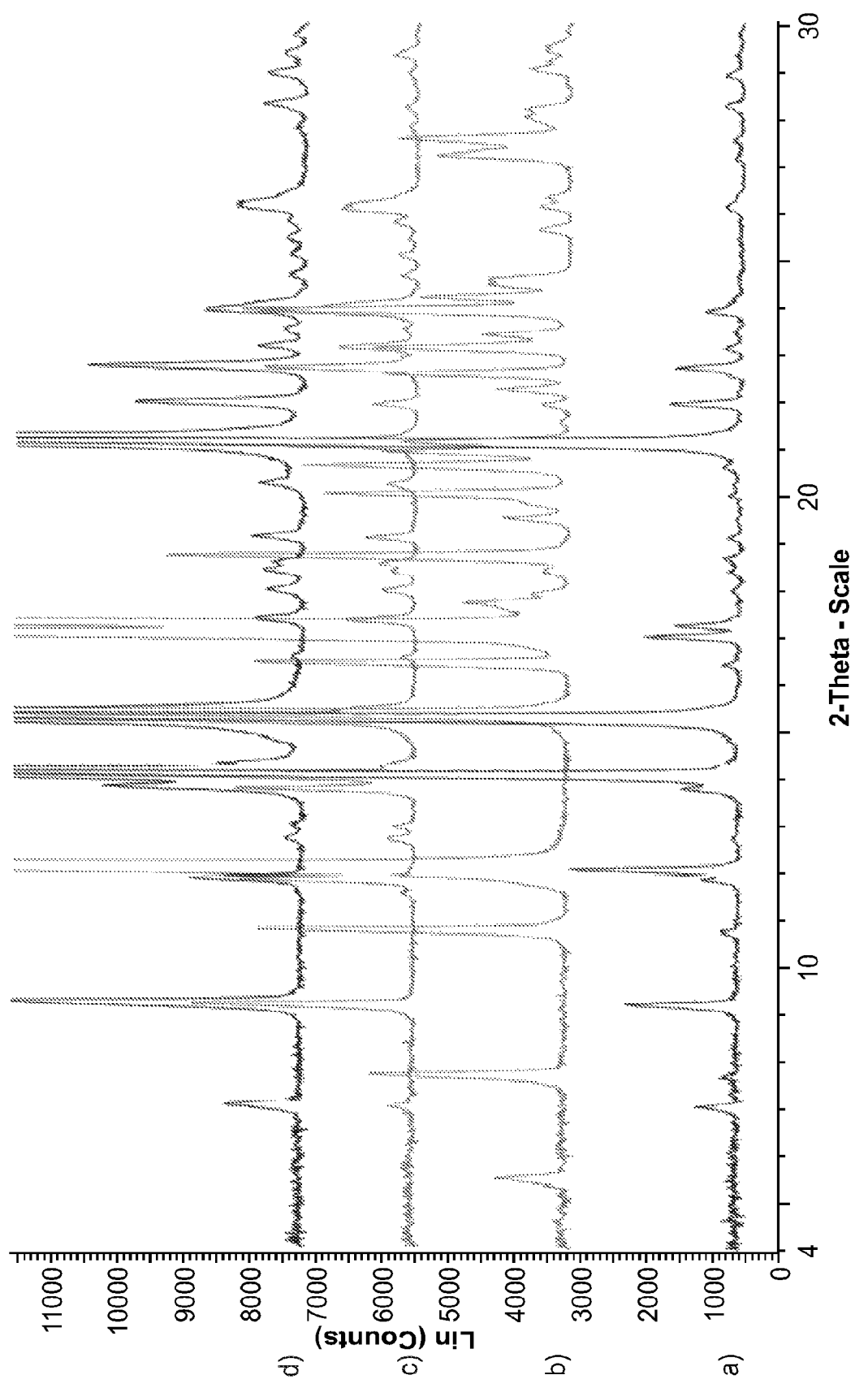
FIG. 8 shows a XRPD stack plot of (R)-2-hydroxy-2-methyl-4-(2,4,5-trimethyl-3,6-dioxocyclohexa-1,4-dienyl)butanamide samples, a) following 24 hours of competitive slurry in 0.5% Methyl Cellulose in water, b) starting material, Pattern A, c) Pattern C, and d) following 7 days of competitive slurry in 0.5% Methyl Cellulose in water.
Figure 9:
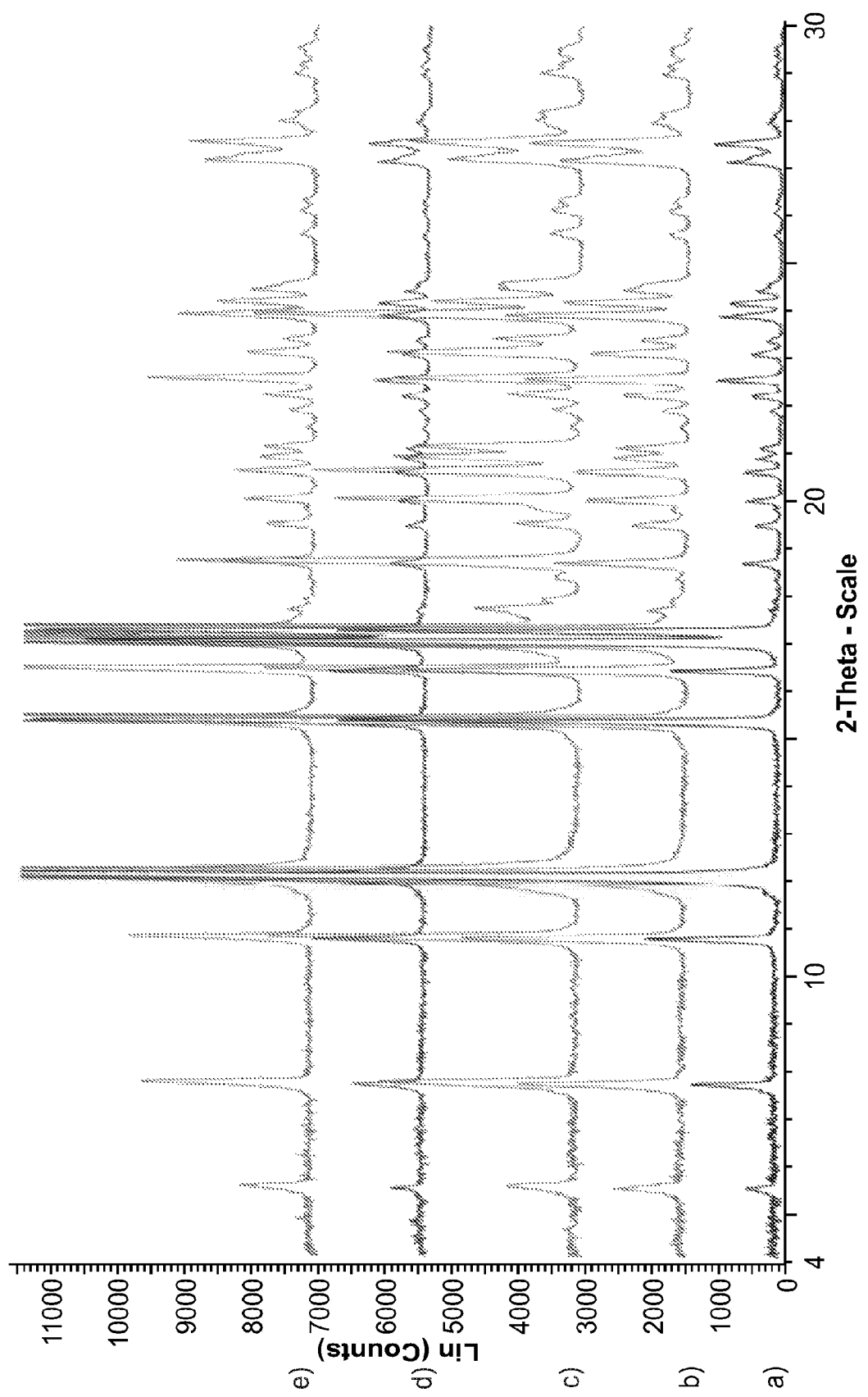
FIG. 9 shows a XRPD stack plot of (R)-2-hydroxy-2-methyl-4-(2,4,5-trimethyl-3,6-dioxocyclohexa-1,4-dienyl)butanamide samples, a) following 24 hours of competitive slurry in IPA, b) following 7 days of competitive slurry in IPA, c) starting material, Pattern A, d) following 24 hours of competitive slurry in isopropanol (IPA)/2% water, e) following 7 days of competitive slurry in IPA/2% water.

Competitive slurry experiments of Patterns A, B, C, D, E and F were initiated in IPA, IPA/2% water and 0.5% Methyl Cellulose in water at ambient conditions as summarized in Table 16. Approximately 100 mg of the starting material, Pattern A, was added to a glass vial fitted with a magnetic stir bar. Solvent was added to the vial and allowed to slurry with Pattern A for 15 minutes before approximately 10-20 mg of each relative Pattern (B, C, D, E and F) was added to each vial. The samples were allowed to equilibrate with stirring and following 24 hours or equilibration, XRPD analysis showed solids isolated from slurry in 0.5% Methyl Cellulose in water was a mixture of Patterns A/C (FIG. 8). All other solids isolated from IPA and IPA/2% water were consistent with the starting material, Pattern A (FIG. 9). However, following 7 days of equilibration full conversion to Pattern C was observed from slurry in 0.5% Methyl Cellulose in water (FIG. 8), where as solids isolated from competitive slurry in IPA and IPA/2% water were consistent with Pattern A (FIG. 9).

TABLE 16

A summary of competitive slurry experiments of (R)-2-hydroxy-2-methyl-4-(2,4,5-trimethyl-3,6-dioxocyclohexa-1,4-dienyl)butanamide in 2 mL of solvent.

| | Pattern (mg) | | | | | | XRPD | |
|---|---|---|---|---|---|---|---|---|
| Solvent | Pattern A | Pattern B | Pattern C | Pattern D | Pattern E | Pattern F | 24 hrs | 7 days |
| IPA | 101.9* | ~10 | ~10 | ~10 | ~10 | ~10 | A | A |
| TPA: water (98:2) | 107.3* | ~10 | ~10 | ~10 | ~10 | ~10 | A | A |
| 0.5% MC/water | 103.9* | ~10 | ~10 | ~10 | ~10 | ~10 | A/C | C |

*Used to saturate the solvent and make a thin slurry of Pattern A

Example 8. Elevated Humidity Studies 7 day elevated aqueous humidity experiments were performed on all Patterns A, B, C, D, E and F at ambient conditions at >95% RH (Table 17). Approximately 30 mg of each pattern was weighed into a 4 ml glass vial. The uncovered 4 ml vial was inserted into a 20 ml scintillation vial half filled with water and capped. Following 24 hours of equilibration, visual inspection was performed to check for changes in physical appearance, however no change was observed. Following 7 days of equilibration at elevated humidity, the sample showed no physical changes and was analyzed by XRPD to check for form. Patterns A, C and E showed no change in form after 7 days of equilibration; however Pattern B was converted to a mixture of Patterns A/B. Pattern D was found to convert to a mixture of Patterns D/B and Pattern F was converted to Pattern E at >95% RH. All experimental details and results are summarized in Table 17.

TABLE 17

Summary of 7 day elevated aqueous humidity experiments of (R)-2-hydroxy-2-methyl-4-(2,4,5-trimethyl-3,6-dioxocyclohexa-1,4-dienyl)butanamide

| | Storage | | Visual Observations | | XRPD [Pattern] |
|---|---|---|---|---|---|
| [mg] | Conditions | Initial Pattern | 1 day | 7 day | 7 day |
| ~30 | >95% RH at Ambient | A | Yellow solids | Yellow Solids | Crystalline [Pattern A] |
| ~30 | >95% RH at Ambient | B | Yellow solids | Yellow solids | Crystalline [Mixture of Patterns A/B] |
| ~30 | >95% RH at Ambient | C | Yellow solids | Yellow solids | Crystalline [Pattern C] |
| ~30 | >95% RH at Ambient | D | Yellow solids | Yellow solids | Crystalline [Mixture of Patterns D/B] |
| ~30 | >95% RH at Ambient | E | Yellow solids | Yellow solids | Crystalline [Pattern E] |
| ~30 | >95% RH at Ambient | F | Yellow solids | Yellow solids | Crystalline [Pattern E] |

Example 9. Grinding Experiments

Grinding experiments of the starting material were performed by dry grinding and solvent drop grinding in IPA and water utilizing a mortar and pestle (Table 18) Following light grinding pattern A, no change in the crystal form was observed by XRPD analysis.

TABLE 18

Summary of Grinding Experiments of (R)-2-hydroxy-2-methyl-4-(2,4,5-trimethyl-3,6-di oxocyclohexa- 1,4-dienyl)butanamide

| Sample Wt. (mg) | Solvent | Grinding | Conditions | XRPD |
|---|---|---|---|---|
| 30-50 | — | yes | RT | Pattern A |
| 30-50 | IPA (2 drops) | yes | RT | Pattern A |
| 30-50 | H2O (2 drops) | yes | RT | Pattern A |

Example 10. Aqueous Solubility

Aqueous solubility of Patterns A, B, C, E and F was performed using an Agilent HPLC system. Approximately 10-20 mg of each form was charged to a 2 mL glass vial loaded with a magnetic stir bar and added 2 mL of water. The samples were allowed to stir overnight at ambient conditions. Following 24 hours of equilibration the samples were centrifuged and decanted into HPLC vials. A calibration curve was generated based on Pattern A in MeOH at 0.05, 0.1, 0.5 and 1.0 mg/mL. Following injection of the standard curve, the samples were run as is. All experimental details and results are summarized in Table 19.

TABLE 19

Summary of Aqueous Solubility experiments of (R)-2-hydroxy-2-methyl-4-(2,4,5-trimethyl-3,6-dioxocyclohexa-1,4-dienyl)butanamide

| Water (mg) | (mL) | Pattern | Designated Form | % AUC | Solubility (mg/mL) |
|---|---|---|---|---|---|
| 15.0 | 2 | F | 2-MeTHF Solvate Form VI | 6813 | 1.36 |
| 12.1 | 2 | E | Anhydrate Form II | 6602 | 1.32 |
| 12.3 | 2 | B | THF Solvate Form IV | 6514 | 1.30 |
| 13.5 | 2 | C | Hydrate Form III | 6646 | 1.32 |
| 21.5 | 2 | A | Anhydrate Form 1 | 8729 | 1.74 |

Example 11. Characterization of Forms

Solid form characterization of (R)-2-hydroxy-2-methyl-4-(2,4,5-trimethyl-3,6-dioxocyclohexa-1,4-dienyl)butanamide, polymorphic forms was completed by XRPD, DSC, TGA, $^1$H NMR, Karl Fischer, optical microscopy, and moisture sorption. Results are summarized in Table 1.

Pattern A (Anhydrate, Form I)

Figure 10:
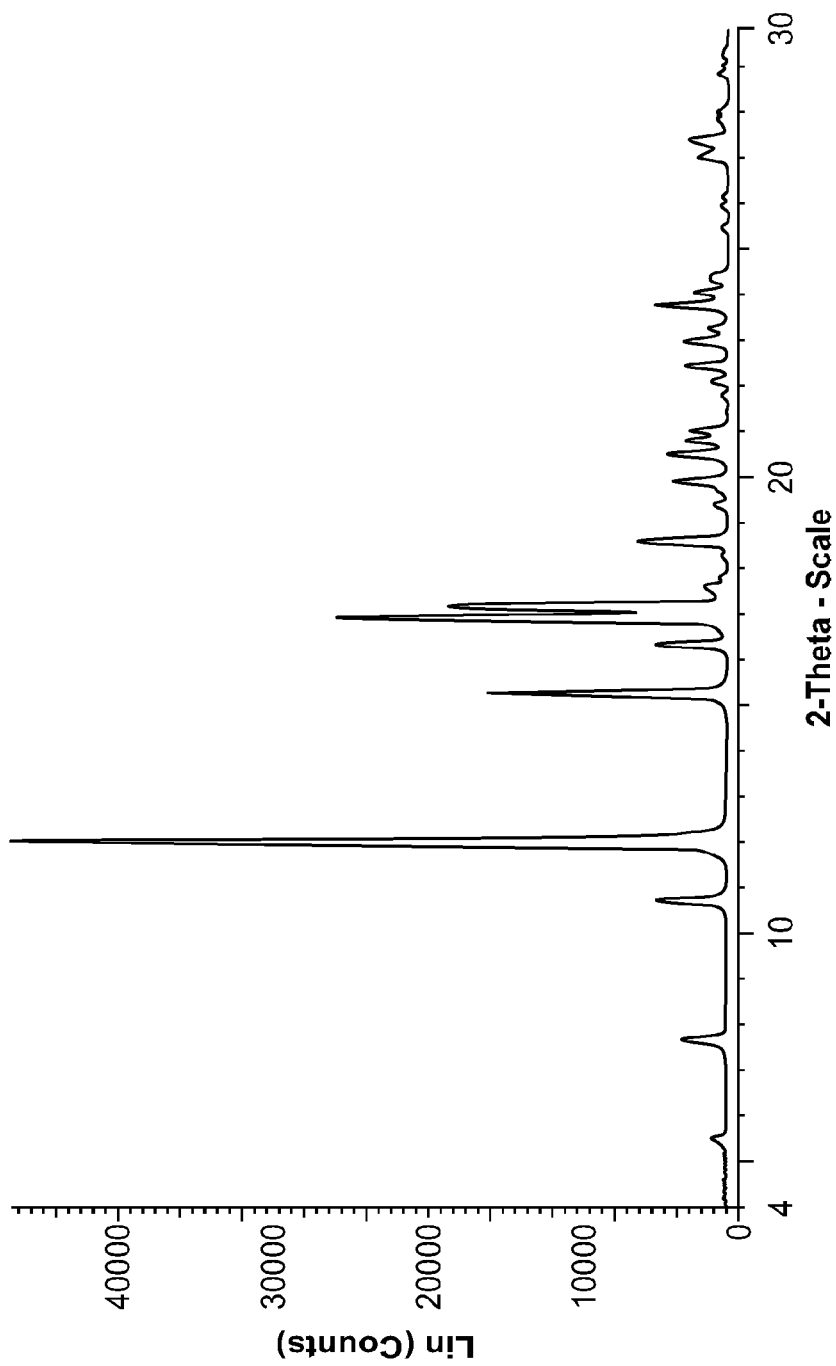
FIG. 10 shows a XRPD of (R)-2-hydroxy-2-methyl-4-(2,4,5-trimethyl-3,6-dioxocyclohexa-1,4-dienyl)butanamide starting material, Pattern A.
Figure 11:
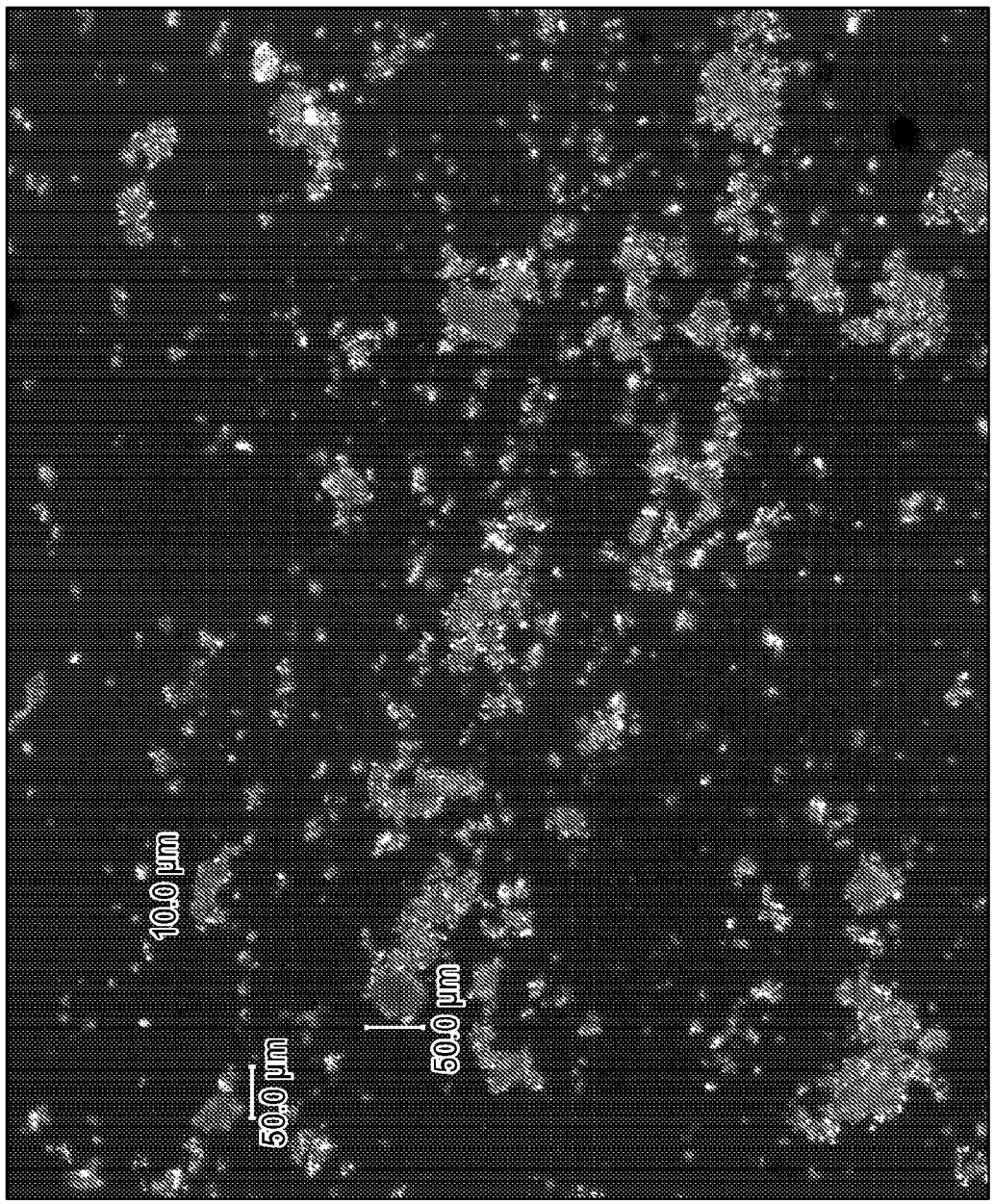
FIG. 11 shows an optical microscopy image of (R)-2-hydroxy-2-methyl-4-(2,4,5-trimethyl-3,6-dioxocyclohexa-1,4-dienyl)butanamide starting material, Pattern A.

Utilizing the starting material as noted in Example 2, XRPD analysis of the yellow colored starting material was found to afford a crystalline pattern, designated as Pattern A (FIG. 10). The crystallinity observed by XRPD was confirmed by the exhibition of birefringence observed by optical microscopy. The morphology of the crystals was determined to be irregularly shaped with some aggregation as shown in FIG. 11.

Figure 12:
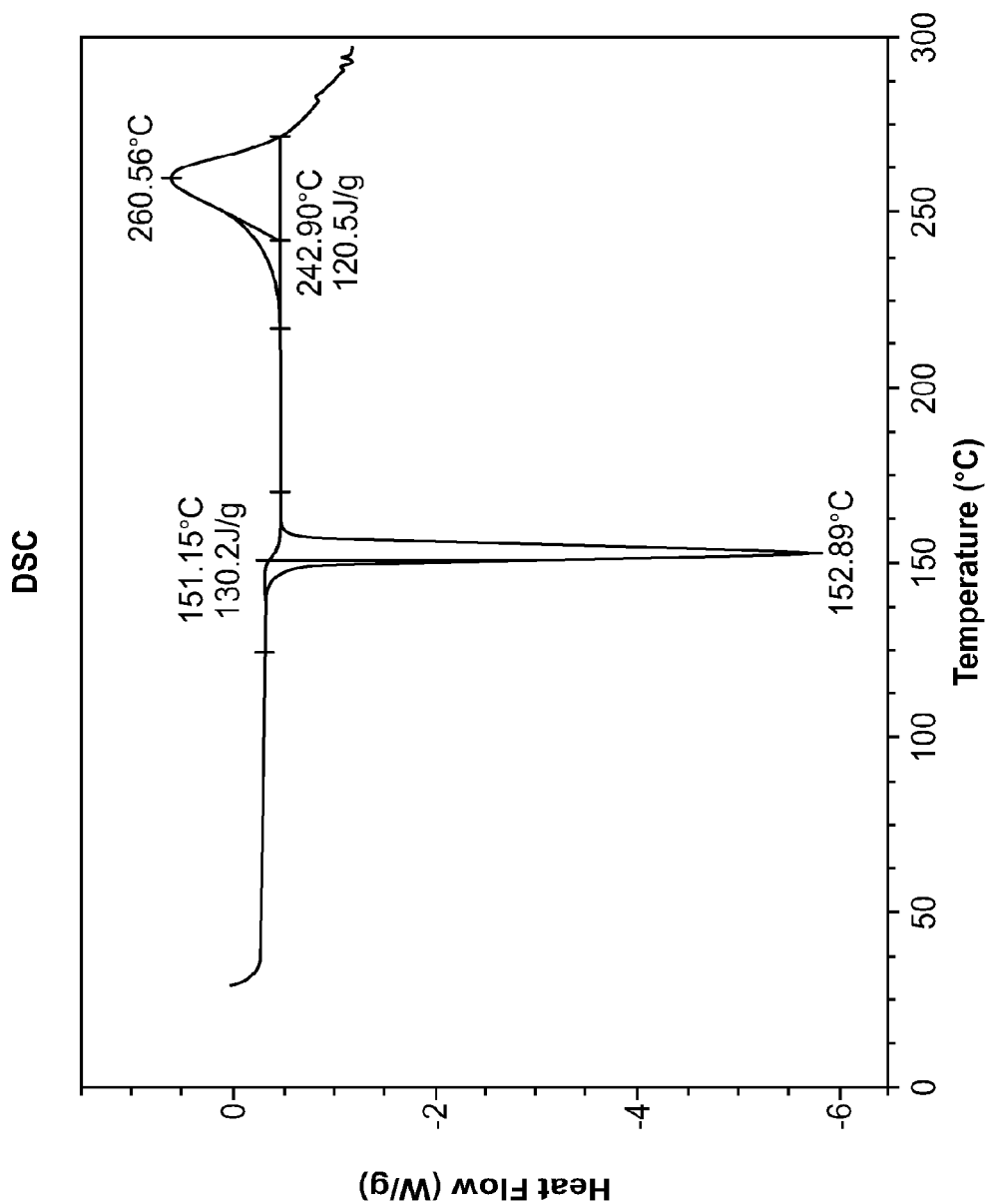
FIG. 12 shows a DSC thermogram of (R)-2-hydroxy-2-methyl-4-(2,4,5-trimethyl-3,6-dioxocyclohexa-1,4-dienyl)butanamide starting material, Pattern A.

Thermal analysis by DSC showed a single endothermic event at peak of 152.9° C., followed by degradation after 200° C. (FIG. 12).

Figure 13:
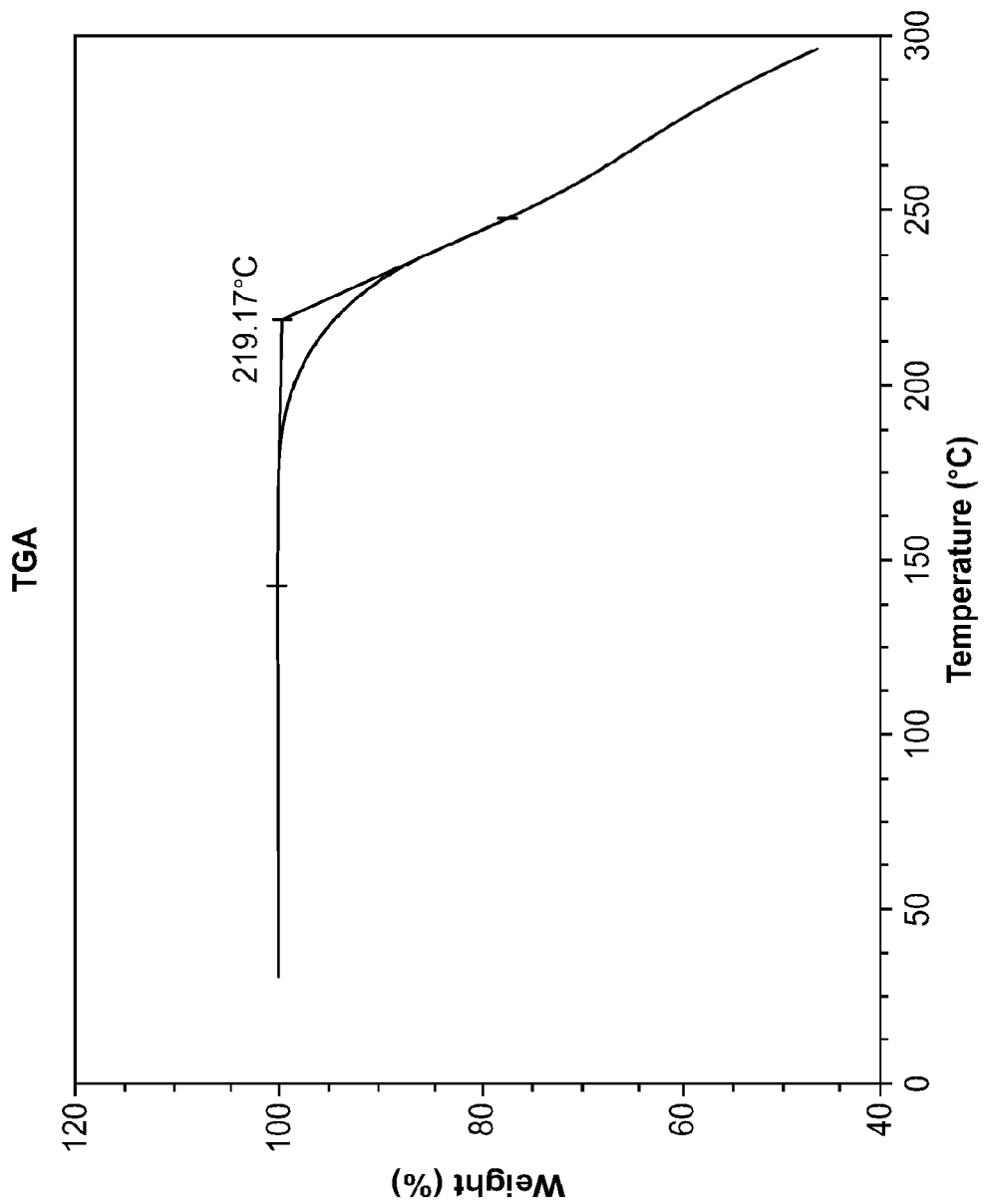
FIG. 13 shows a TGA thermogram of (R)-2-hydroxy-2-methyl-4-(2,4,5-trimethyl-3,6-dioxocyclohexa-1,4-dienyl)butanamide starting material, Pattern A.

TGA analysis showed no weight loss between 45-160° C., however weight loss due to decomposition was observed from 160-300° C. (FIG. 13). Minimal moisture content was confirmed by Karl Fischer analysis which showed the materials to contain approximately 0.12 wt % water.

Figure 40:
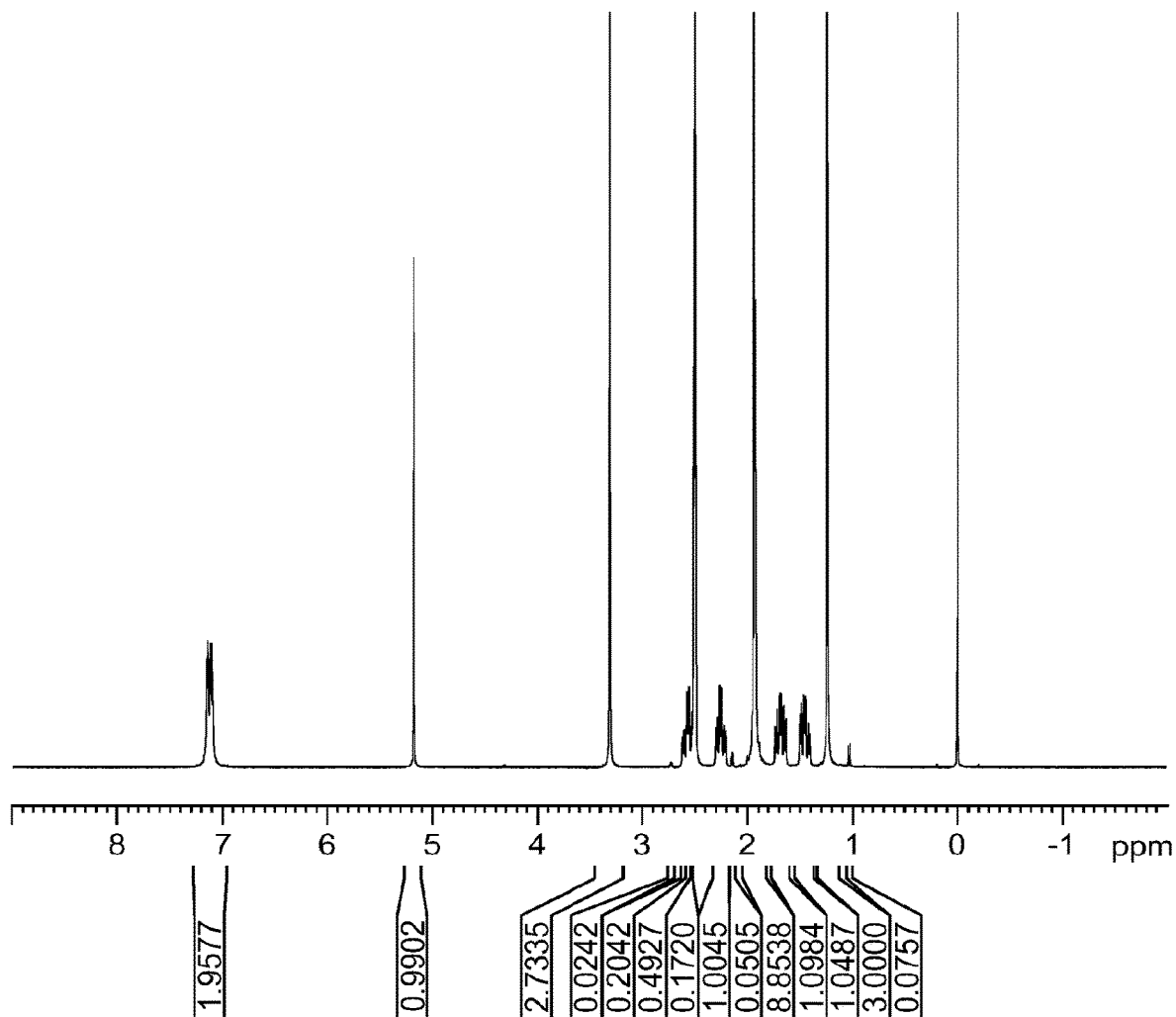
FIG. 40 shows a $^1$H NMR spectrum of (R)-2-hydroxy-2-methyl-4-(2,4,5-trimethyl-3,6-dioxocyclohexa-1,4-dienyl)butanamide starting material, Pattern A

Further analysis by $^1$H NMR showed the starting material to be consistent with structure of (R)-2-hydroxy-2-methyl-4-(2,4,5-trimethyl-3,6-dioxocyclohexa-1,4-dienyl)butanamide and to contain 0.28 wt % residual IPA. See FIG. 40.

Figure 14:
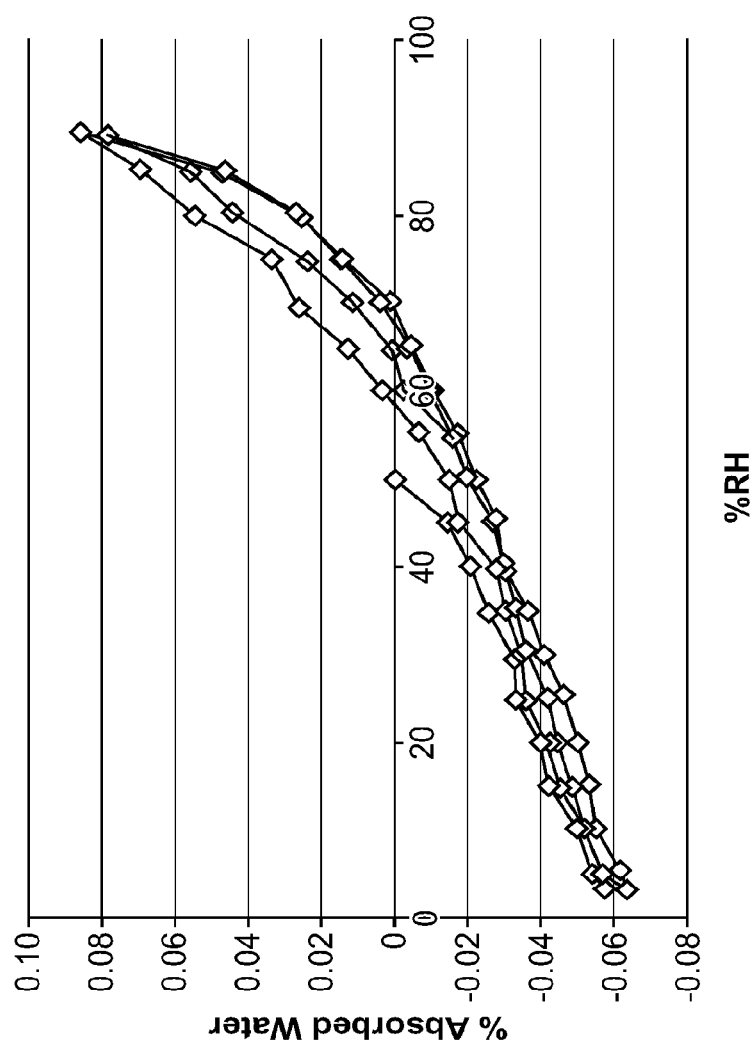
FIG. 14 shows a moisture sorption-desorption plot of (R)-2-hydroxy-2-methyl-4-(2,4,5-trimethyl-3,6-dioxocyclohexa-1,4-dienyl)butanamide starting material, Pattern A.

Moisture sorption analysis of the starting material was performed by equilibrating the sample at 25° C. and 50% RH to simulate ambient lab conditions. Humidity then decreased to 0% RH, increased from ● to 95% RH, reduced from 95 to 0% RH, increased from ● to 95% RH and then decreased from 95 to 50% RH. Each point represents the estimated asymptotic weight for each humidity or weight. The starting material was found to non-hygroscopic, adsorbing 0.1% water at 90% RH. No hysteresis was observed upon desorption (FIG. 14). XRPD analysis of sample following moisture sorption analysis was found to be consistent with the starting material, Pattern A Pattern E (Anhydrate, Form II)

Figure 15:
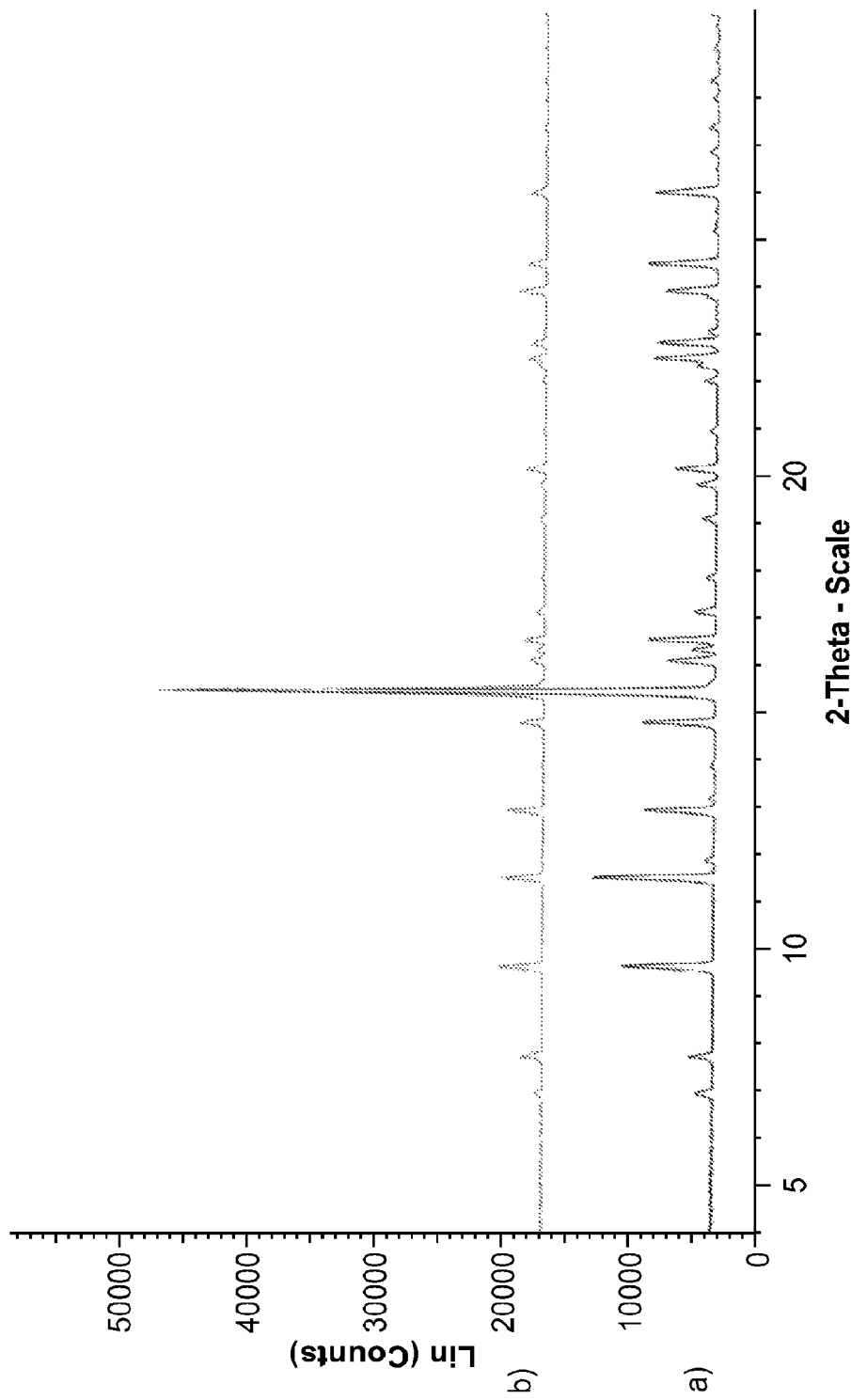
FIG. 15 shows a XRPD stack plot of (R)-2-hydroxy-2-methyl-4-(2,4,5-trimethyl-3,6-dioxocyclohexa-1,4-dienyl)butanamide Pattern E isolated from single solvent fast cooling experiments, a) from 50 mg scale and b) from 300 mg scale-up.
Figure 16:
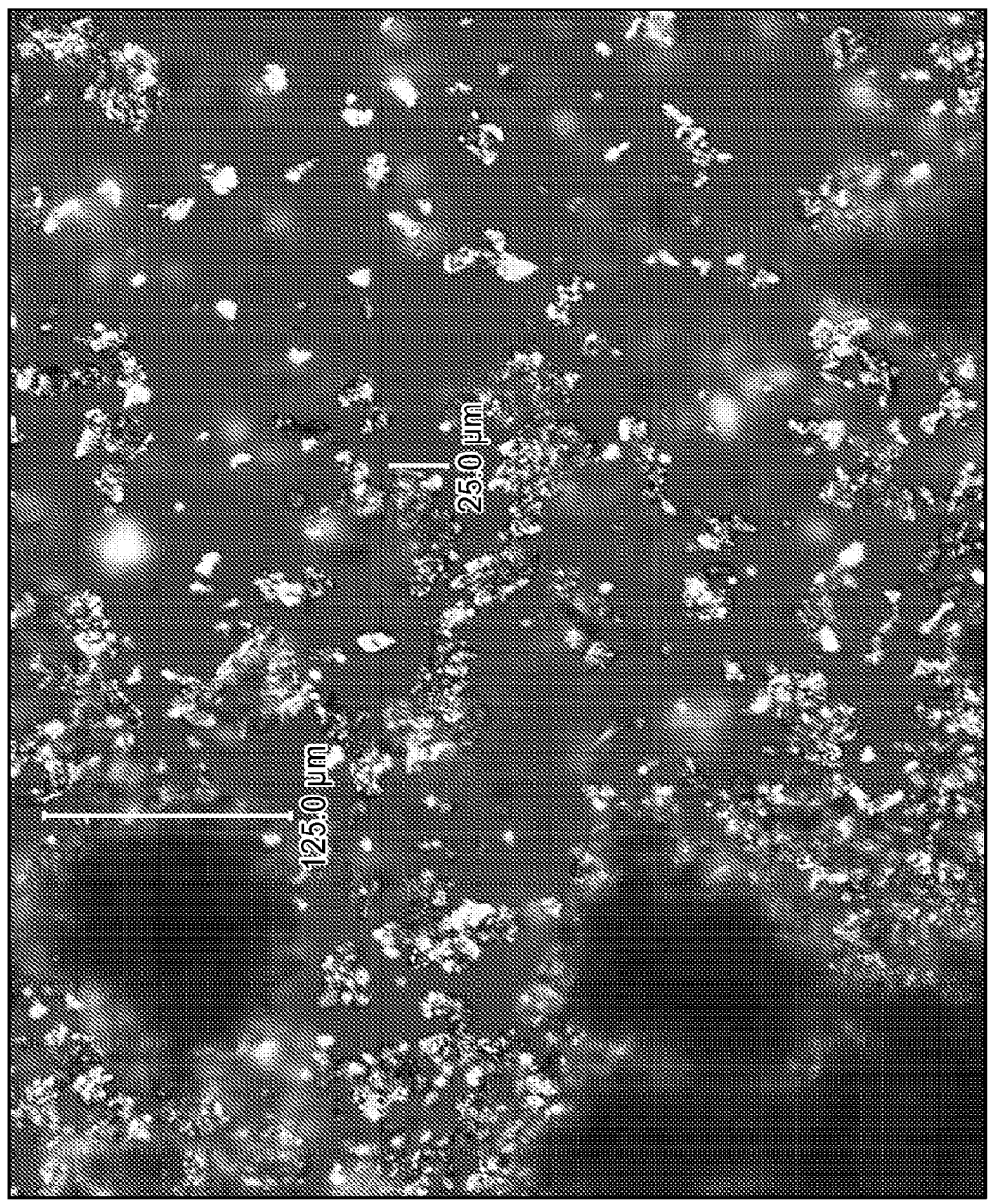
FIG. 16 shows an optical microscopy image of (R)-2-hydroxy-2-methyl-4-(2,4,5-trimethyl-3,6-dioxocyclohexa-1,4-dienyl)butanamide, Pattern E.

Pattern E (Anhydrate, Form II) was observed during single solvent crystallizations (Examples 5 and 6) using a fast cooling profile at the 50 mg scale and again at the 300 mg scale-up. XRPD analysis of the solids were found to afford a unique crystalline pattern, designated as Pattern E (FIG. 15). The crystallinity observed by XRPD was confirmed by the exhibition of birefringence observed by optical microscopy. The morphology of the crystals was determined to be irregularly shaped with some aggregation as shown in FIG. 16.

Figure 17:
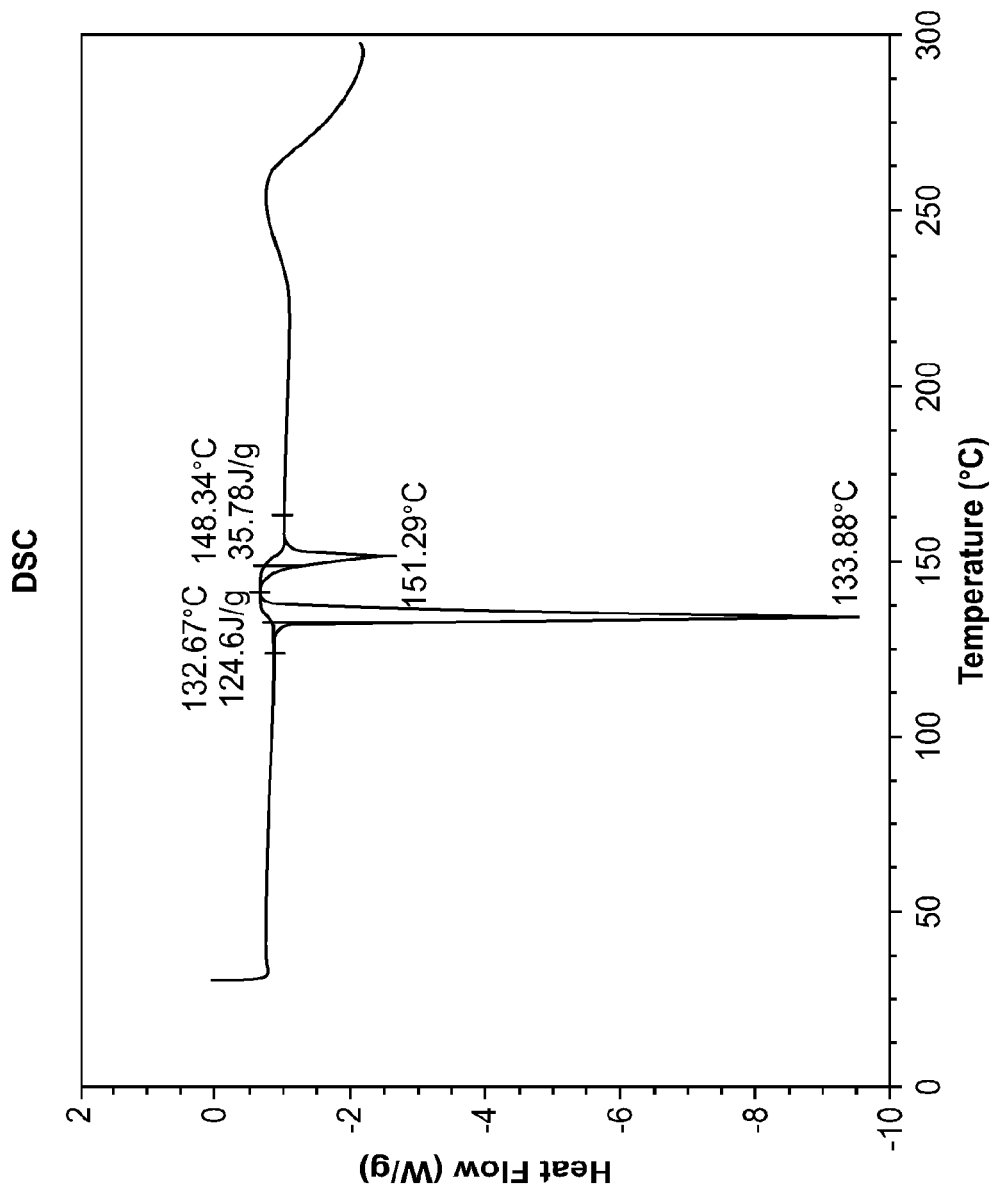
FIG. 17 shows a DSC thermogram of (R)-2-hydroxy-2-methyl-4-(2,4,5-trimethyl-3,6-dioxocyclohexa-1,4-dienyl)butanamide, Pattern E.

Thermal analysis of the 50 mg scale lot by DSC showed a two endothermic events at peak of 133.9° C. and 151.3° C., followed by degradation after 200° C. (FIG. 17).

Figure 18:
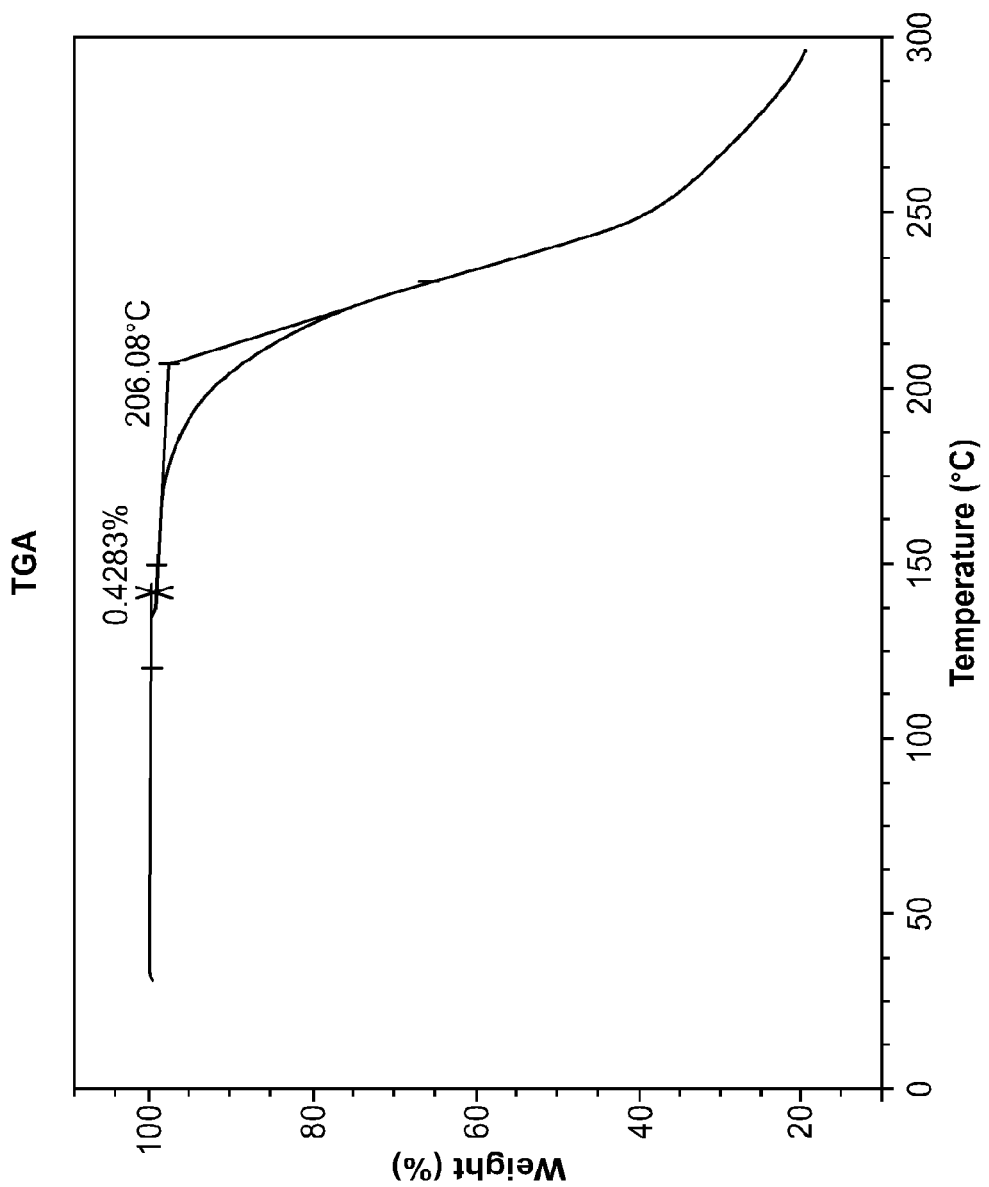
FIG. 18 shows a TGA thermogram of (R)-2-hydroxy-2-methyl-4-(2,4,5-trimethyl-3,6-dioxocyclohexa-1,4-dienyl)butanamide, Pattern E. 100691

TGA analysis of the 50 mg scale lot, showed a 0.4% weight loss between 120-140° C., likely attributed to the loss of EtOAc, followed by decomposition (FIG. 18). Minimal moisture content was confirmed by Karl Fischer analysis which showed the materials to contain approximately 0.1 wt % water.

Figure 44:
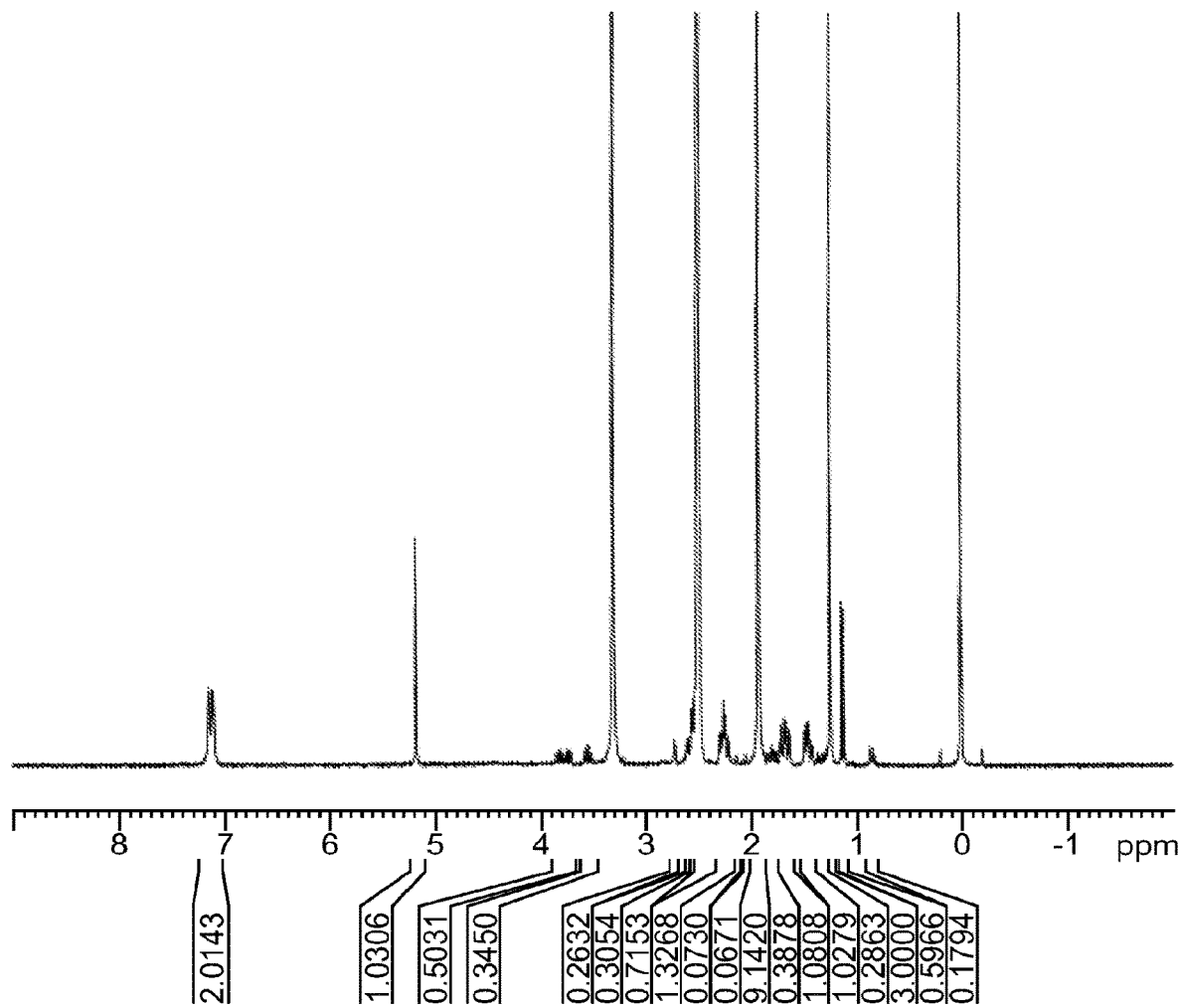
FIG. 44 shows a $^1$H NMR spectrum of (R)-2-hydroxy-2-methyl-4-(2,4,5-trimethyl-3,6-dioxocyclohexa-1,4-dienyl)butanamide, Pattern E

Further analysis of Pattern E (from the 300 mg scale lot) by $^1$H NMR showed the material to be consistent with structure of (R)-2-hydroxy-2-methyl-4-(2,4,5-trimethyl-3,6-dioxocyclohexa-1,4-dienyl)butanamide and to contain 0.4 wt % residual EtOAc. See FIG. 44.

Figure 19:
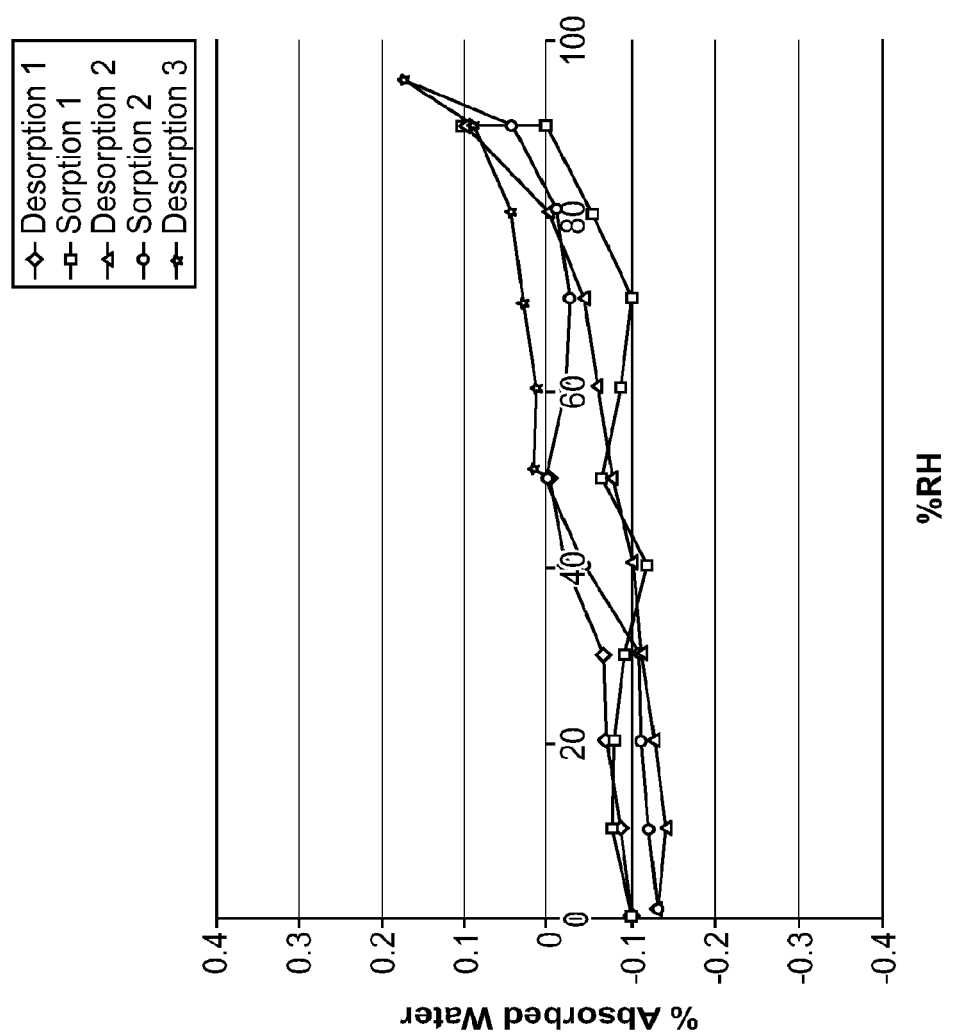
FIG. 19 shows a moisture sorption-desorption plot of (R)-2-hydroxy-2-methyl-4-(2,4,5-trimethyl-3,6-dioxocyclohexa-1,4-dienyl)butanamide Pattern E.

Moisture sorption analysis of Pattern E (from the 300 mg scale lot) was performed by equilibrating the sample at 25° C. and 50% RH to simulate ambient lab conditions. Humidity was then decreased to 0% RH, increased from 0 to 95% RH, reduced from 95 to 0% RH, increased from 0 to 95% RH and then decreased from 95 to 50% RH. Each point represents the estimated asymptotic weight for each humidity or weight. Pattern E was found to non-hygroscopic, adsorbing 0.2% water at 95% RH. No hysteresis was observed upon desorption (FIG. 19). XRPD analysis of sample following moisture sorption analysis was found to be consistent with Pattern E.

Pattern C (Hydrate, Form III)

Figure 20:
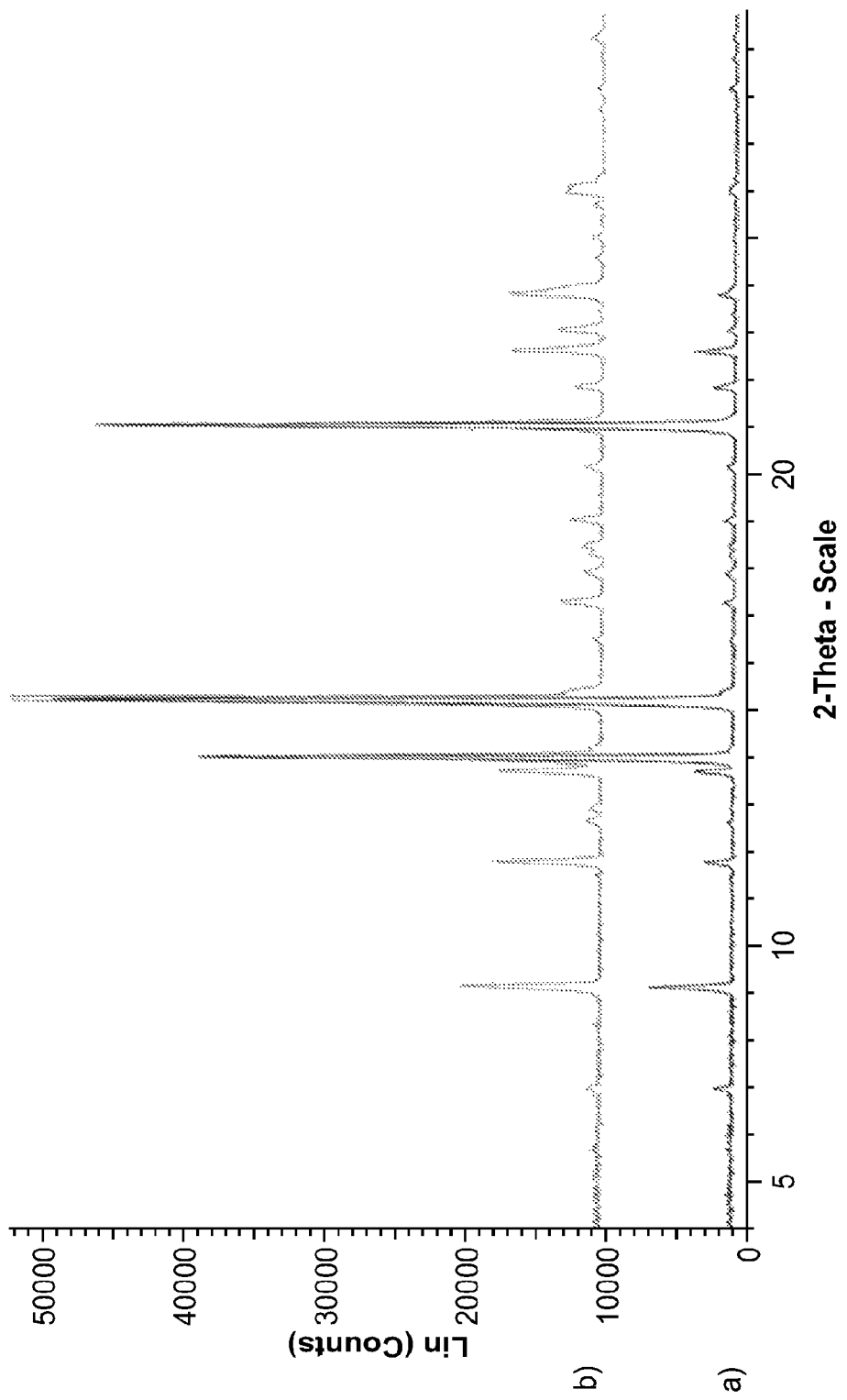
FIG. 20 shows a XRPD stack plot of (R)-2-hydroxy-2-methyl-4-(2,4,5-trimethyl-3,6-dioxocyclohexa-1,4-dienyl)butanamide Pattern C from slurry in 0.5% Methyl Cellulose/2% Tween 80, a) from 50 mg scale and b) from 300 mg scale-up.
Figure 21:
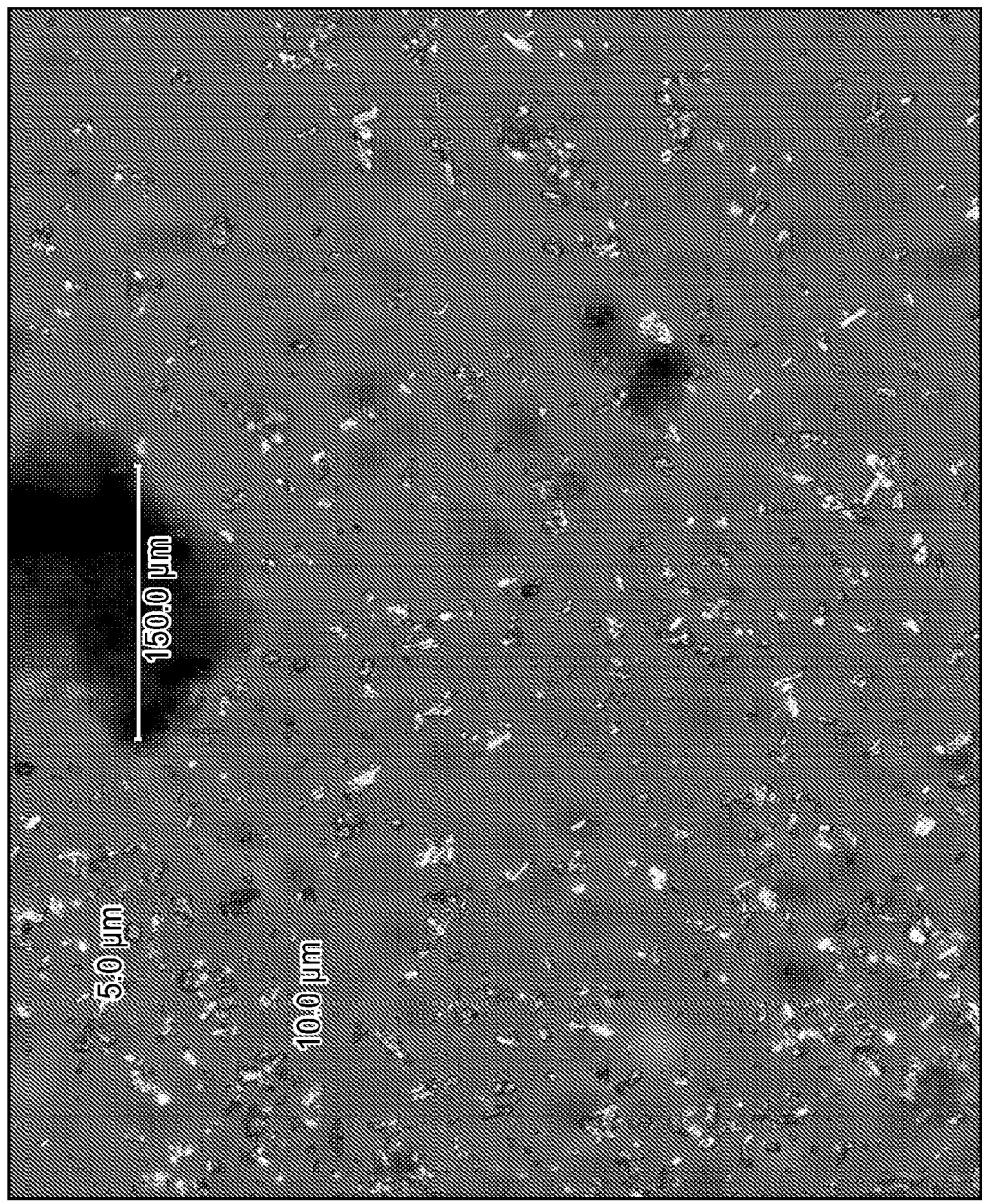
FIG. 21 shows an optical microscopy image of (R)-2-hydroxy-2-methyl-4-(2,4,5-trimethyl-3,6-dioxocyclohexa-1,4-dienyl)butanamide, Pattern C.

Pattern C (Hydrate, Form III) was observed during short term slurry in 0.5% Methyl Cellulose/2% Tween 80 at the 50 mg scale and again at the 300 mg scale-up (Examples 3 and 6, respectively). XRPD analysis of the solids were found to afford a unique crystalline pattern, designated as Pattern C (FIG. 20). The crystallinity observed by XRPD was confirmed by the exhibition of birefringence observed by optical microscopy. The morphology of the crystals was determined to be irregularly shaped with some aggregation as shown in FIG. 21.

Figure 22:
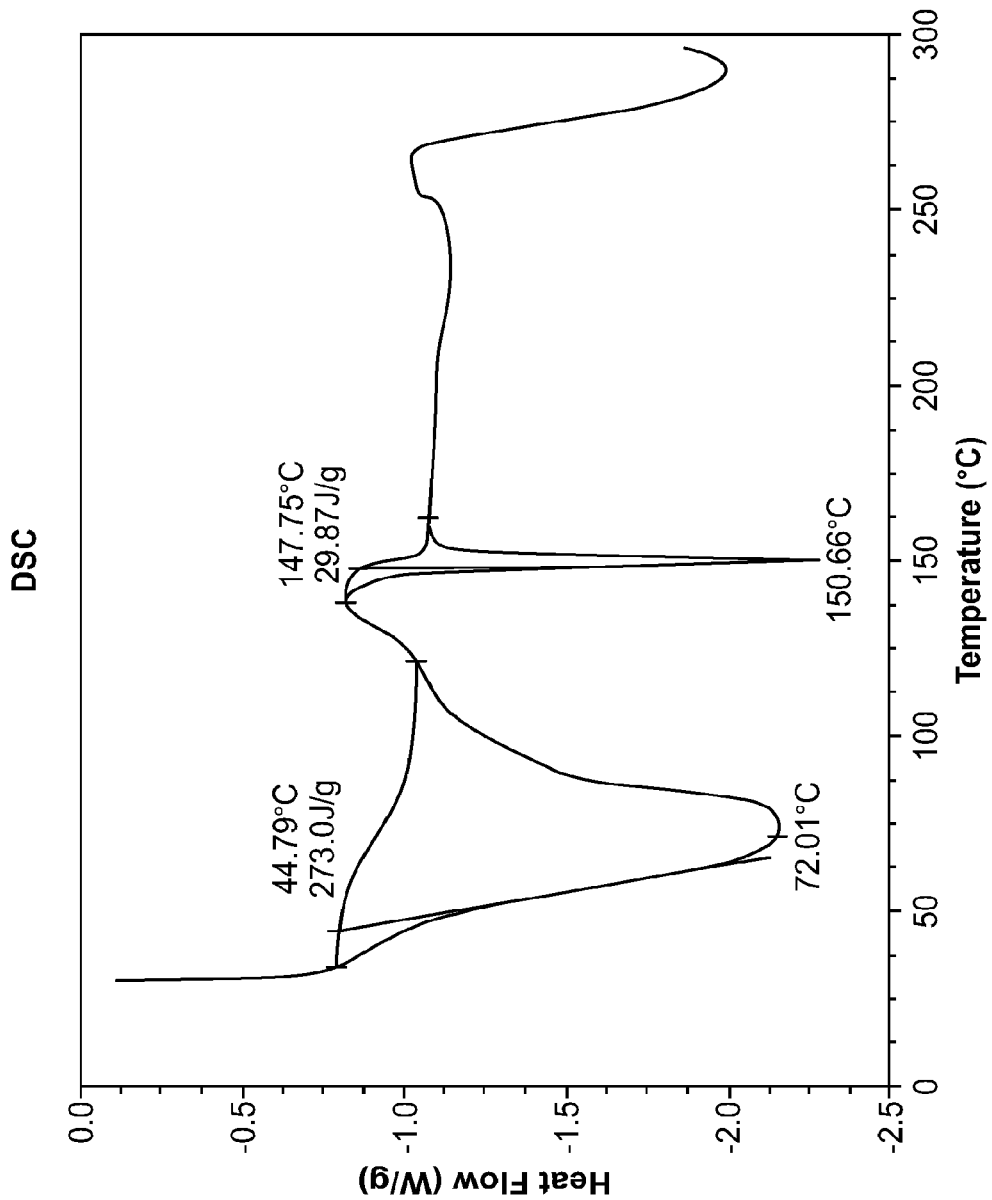
FIG. 22 shows a DSC thermogram of (R)-2-hydroxy-2-methyl-4-(2,4,5-trimethyl-3,6-dioxocyclohexa-1,4-dienyl)butanamide, Pattern C.

Thermal analysis of the 50 mg lot by DSC showed two endothermic events at peaks of 72° C. and 150.7° C., followed by degradation after 200° C. (FIG. 22).

Figure 23:
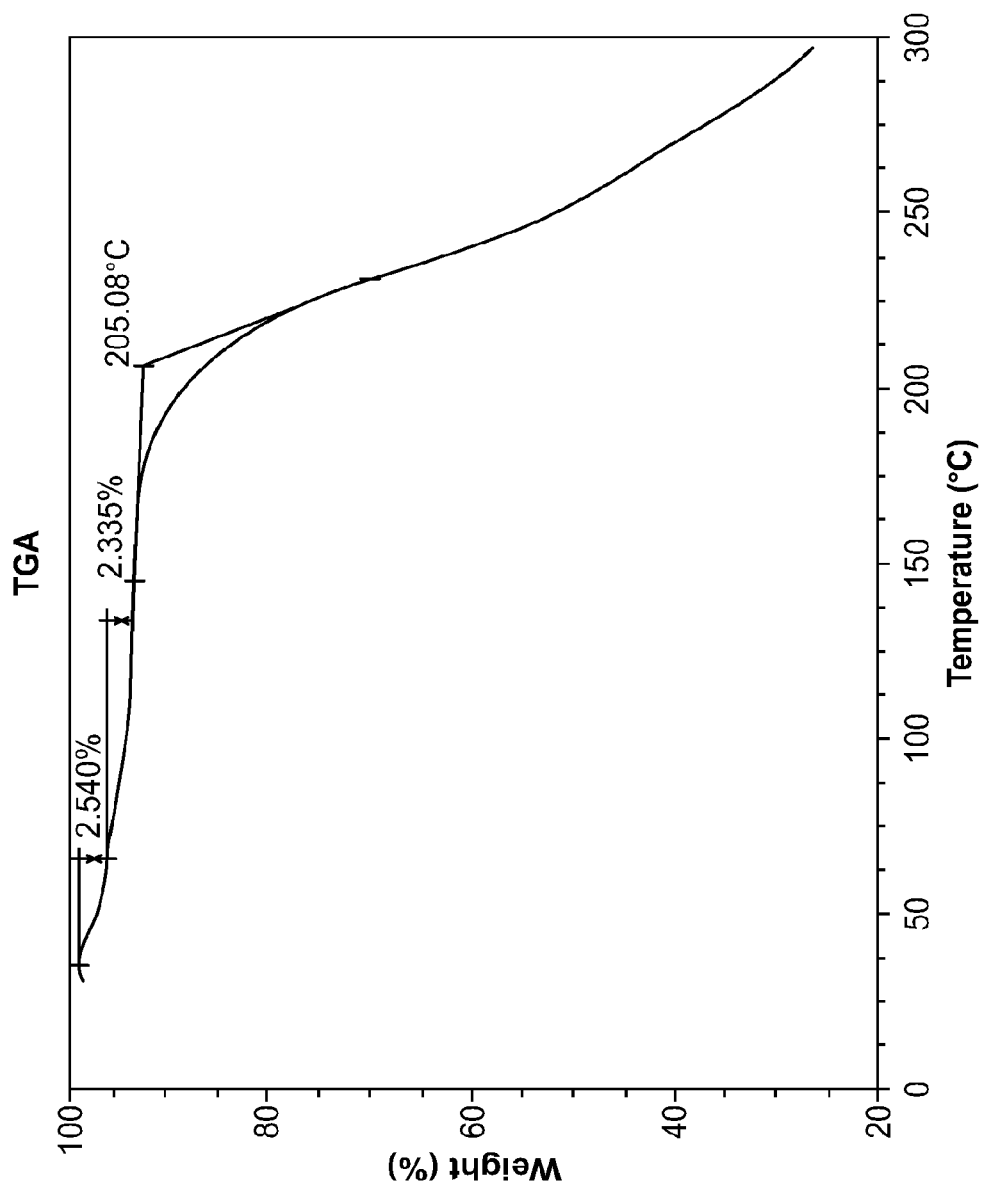
FIG. 23 shows a TGA thermogram of (R)-2-hydroxy-2-methyl-4-(2,4,5-trimethyl-3,6-dioxocyclohexa-1,4-dienyl)butanamide, Pattern C.

TGA analysis of the 50 mg lot showed a 2.5% weight loss between 20-60° C., followed by a 2.3% wt. loss from 60-125° C., likely attributed to dehydration, followed by decomposition (FIG. 23). Moisture content was confirmed by Karl Fischer analysis which showed the materials to contain approximately 4.3 wt % water, slightly lower than a monohydrate.

Figure 42:
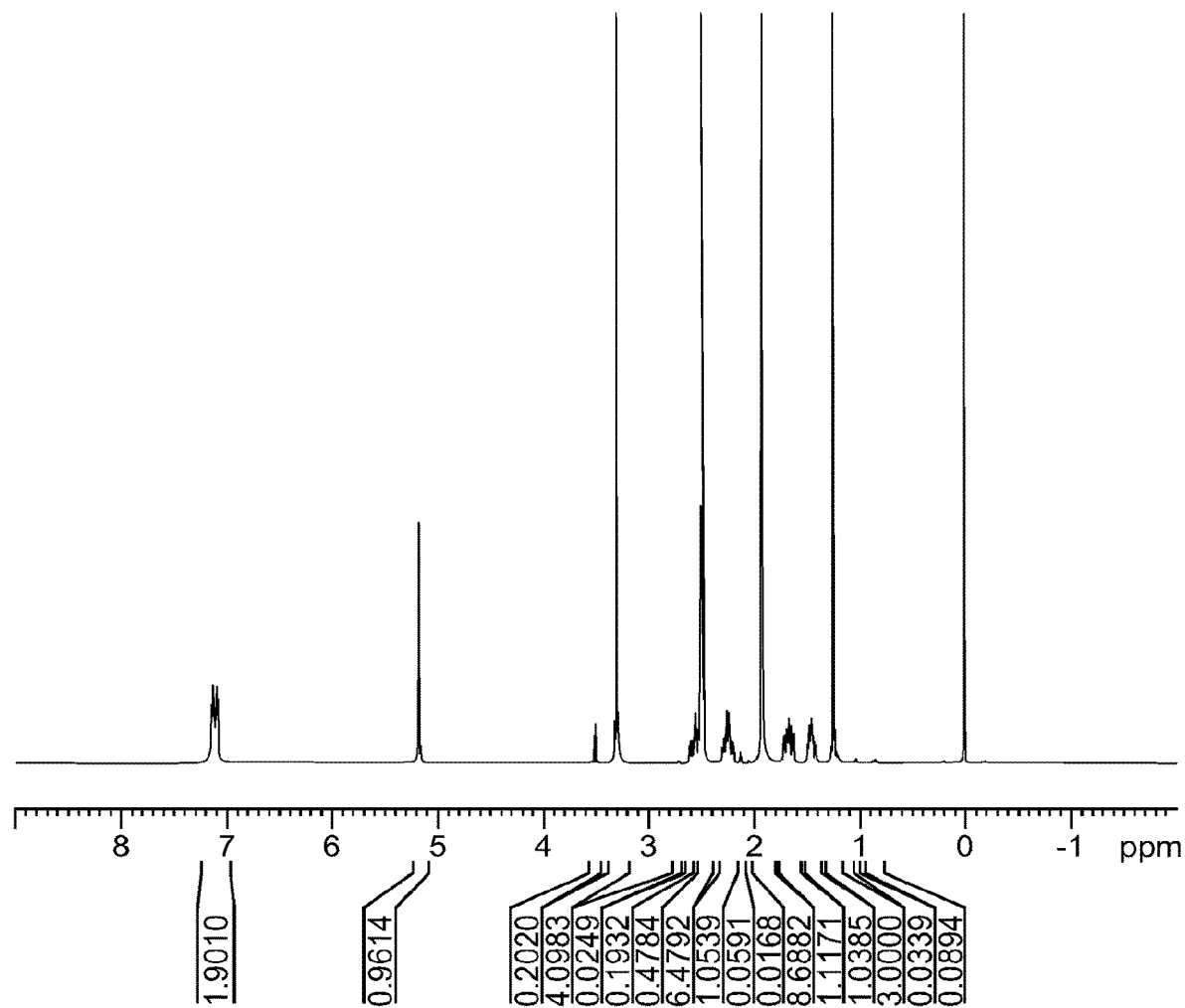
FIG. 42 shows a $^1$H NMR spectrum of (R)-2-hydroxy-2-methyl-4-(2,4,5-trimethyl-3,6-dioxocyclohexa-1,4-dienyl)butanamide Pattern C

Further analysis of Pattern C (300 mg lot) by $^1$H NMR showed the material to be consistent with structure of (R)-2-hydroxy-2-methyl-4-(2,4,5-trimethyl-3,6-dioxocyclohexa-1,4-dienyl)butanamide. See FIG. 42.

Moisture sorption analysis of Pattern C (300 mg lot) was performed by equilibrating the sample at 25° C. and 50% RH to simulate ambient lab conditions. Humidity was then decreased to 0% RH, increased from 0 to 95% RH, reduced from 95 to 0% RH, increased from 0 to 95% RH and then decreased from 95 to 50% RH. Each point represents the estimated asymptotic weight for each humidity or weight. Pattern C was found to be slightly hygroscopic, adsorbing 2% water at 95% RH. This increased the total water to about 6% which is the water content of mono-hydrate. However, upon reducing the relative humidity, the solid lost its water.

Figure 24:
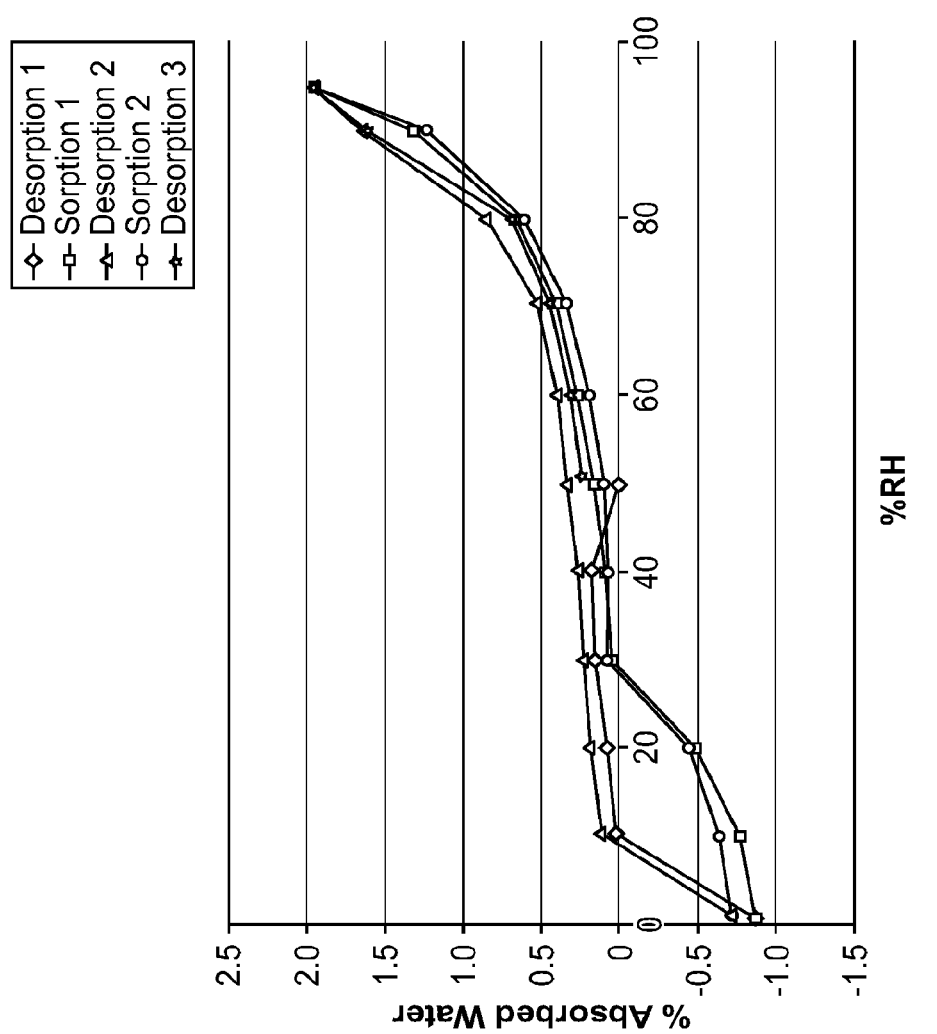
FIG. 24 shows a moisture sorption-desorption plot of (R)-2-hydroxy-2-methyl-4-(2,4,5-trimethyl-3,6-dioxocyclohexa-1,4-dienyl)butanamide Pattern C.

Therefore this could be a channel hydrate. No hysteresis was observed upon desorption (FIG. 24). XRPD analysis of sample following moisture sorption analysis was found to be consistent with Pattern C.

Pattern B (THF Solvate, Form IV)

Figure 25:
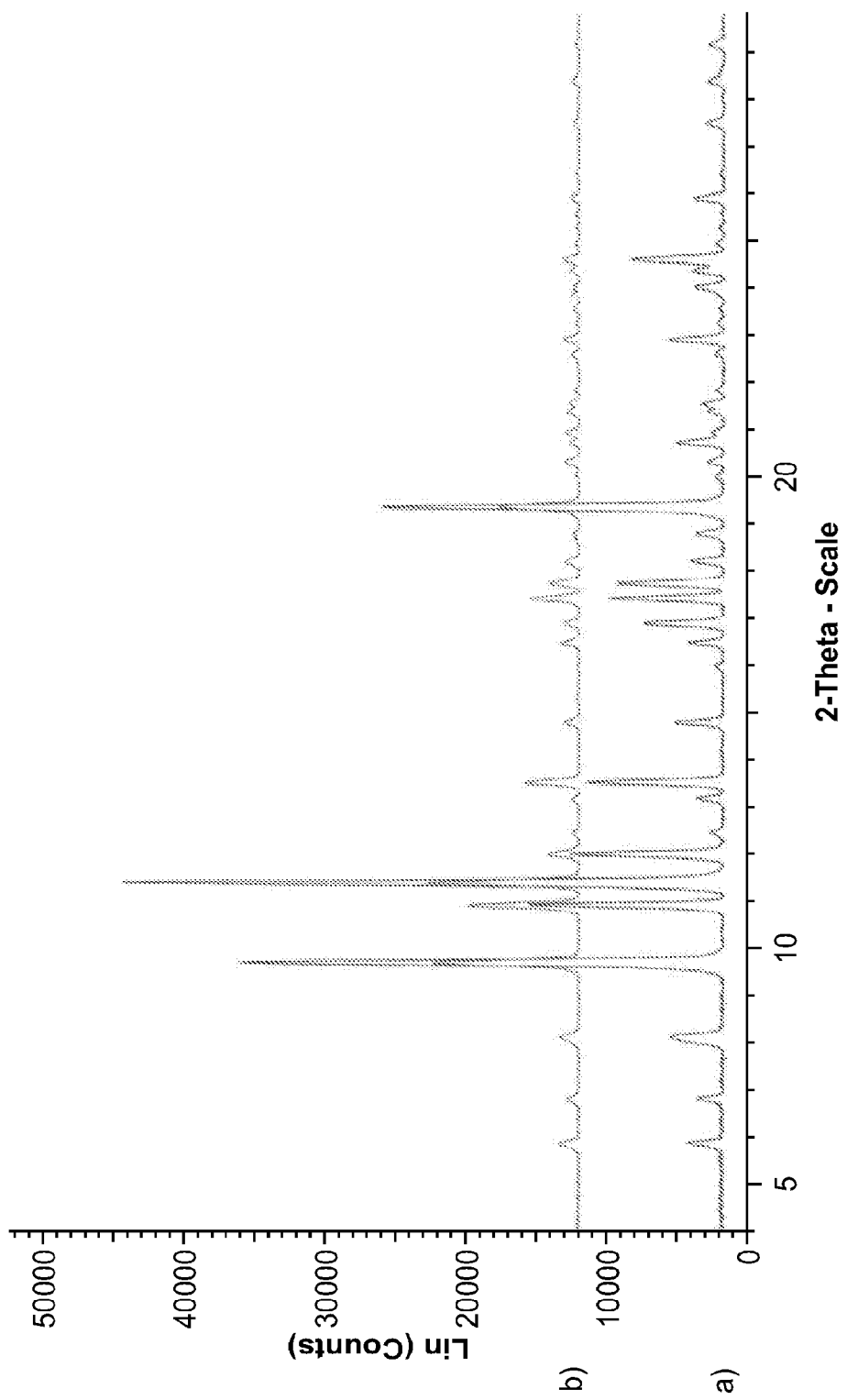
FIG. 25 shows a XRPD stack plot of (R)-2-hydroxy-2-methyl-4-(2,4,5-trimethyl-3,6-dioxocyclohexa-1,4-dienyl)butanamide Pattern B from slurry in THF, a) from 50 mg scale and b) from 300 mg scale-up.
Figure 26:
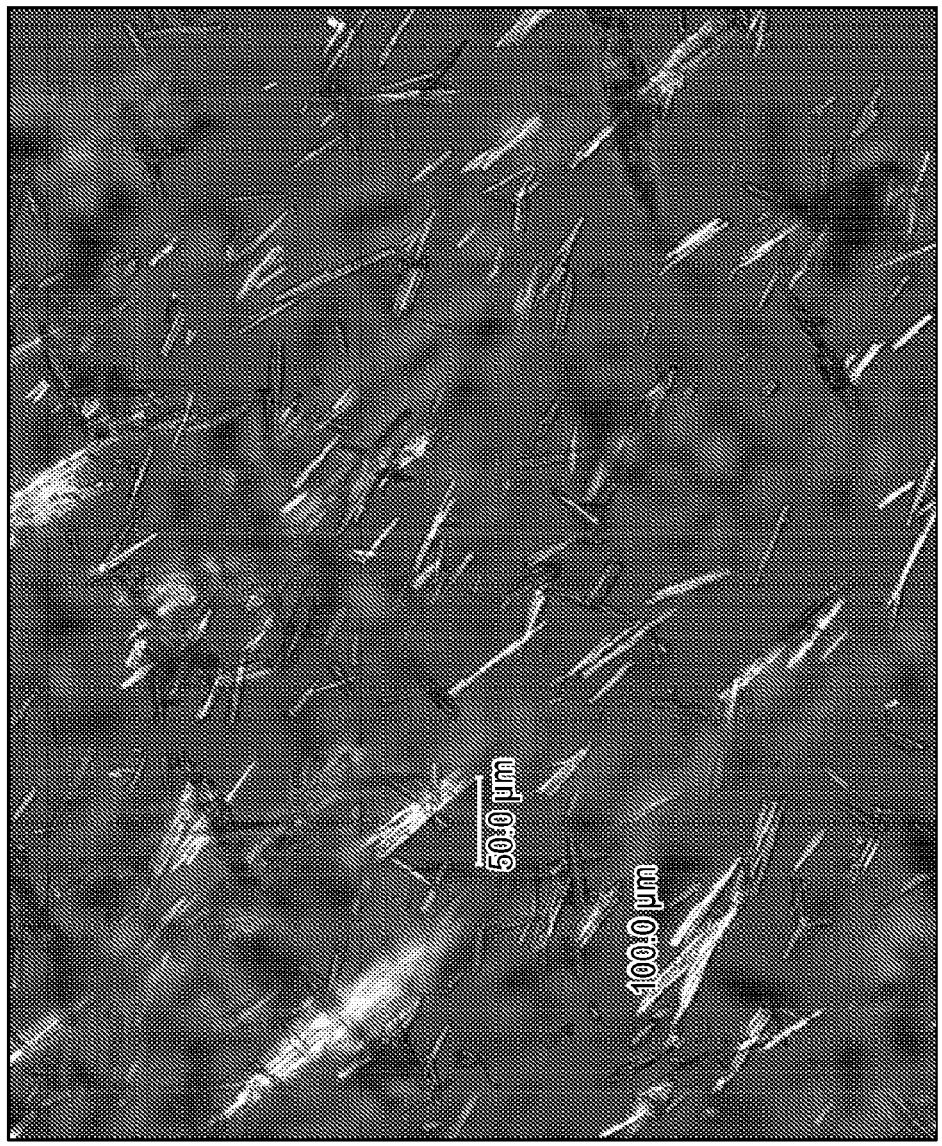
FIG. 26 shows an optical microscopy image of (R)-2-hydroxy-2-methyl-4-(2,4,5-trimethyl-3,6-dioxocyclohexa-1,4-dienyl)butanamide, Pattern B.

Pattern B (THF Solvate, Form IV) was observed during short term slurry in THF at the 50 mg scale and again at the 300 mg scale-up (Examples 3 and 6 respectively). XRPD analysis of the solids were found to afford a unique crystalline pattern, designated as Pattern B (FIG. 25) The crystallinity observed by XRPD was confirmed by the exhibition of birefringence observed by optical microscopy. The morphology of the crystals was determined to be needle shaped with some aggregation as shown in FIG. 26

Figure 27:
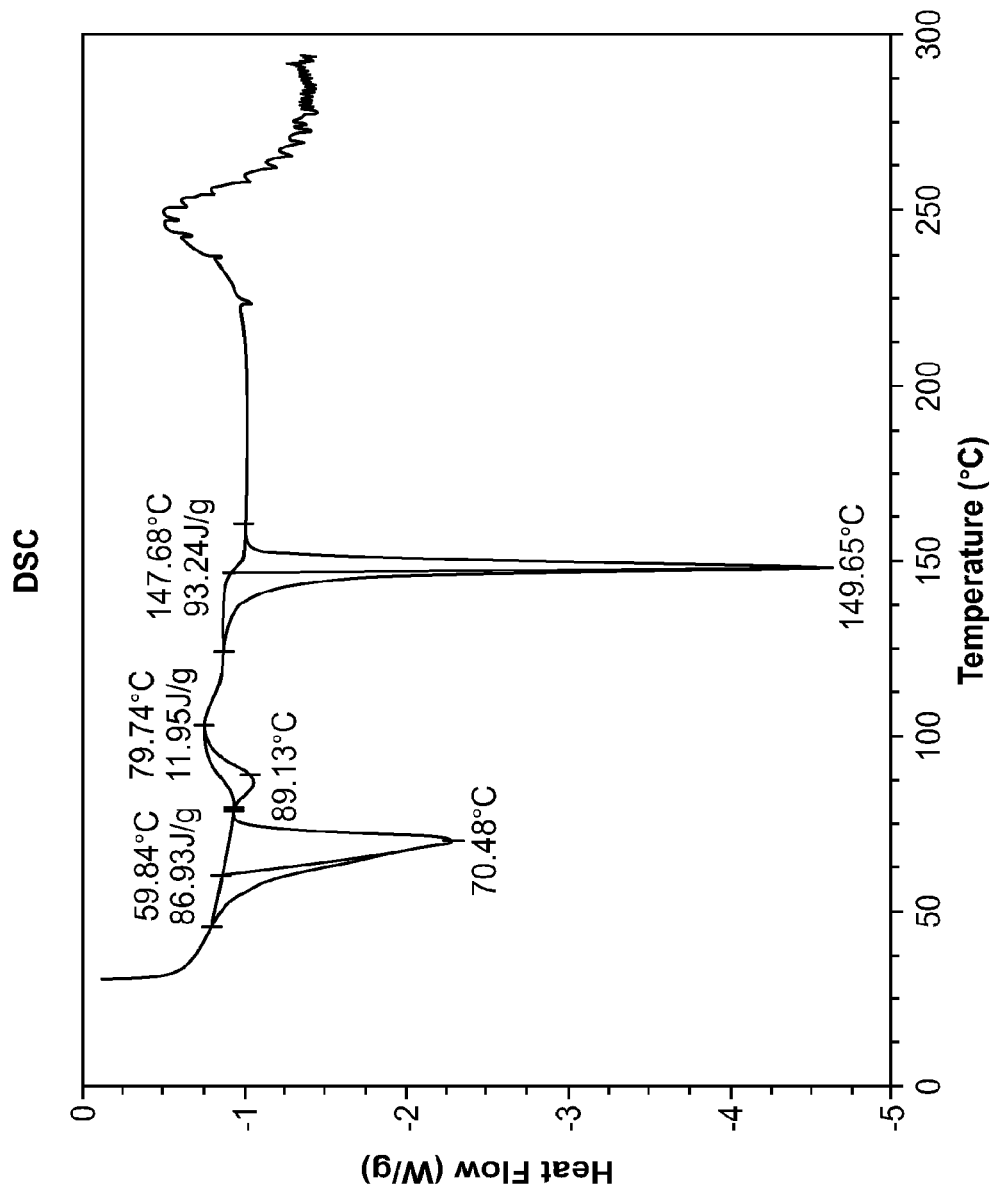
FIG. 27 shows a DSC thermogram of (R)-2-hydroxy-2-methyl-4-(2,4,5-trimethyl-3,6-dioxocyclohexa-1,4-dienyl)butanamide, Pattern B.

Thermal analysis of the 50 mg lot, by DSC showed three endothermic events at peak of 70.5, 89.1° C. and 149.7° C., followed by degradation after 200° C. (FIG. 27).

Figure 28:
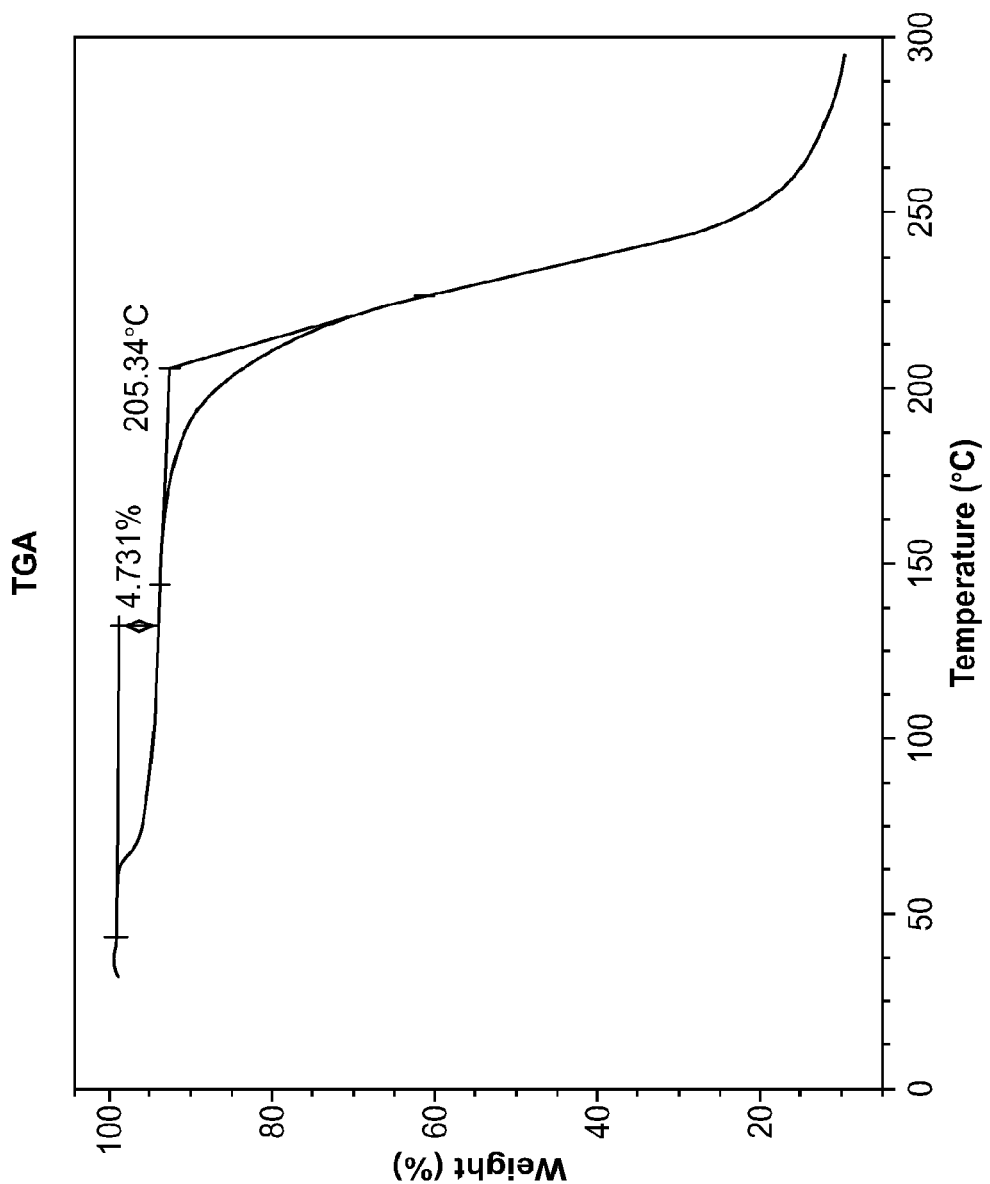
FIG. 28 shows a TGA thermogram of (R)-2-hydroxy-2-methyl-4-(2,4,5-trimethyl-3,6-dioxocyclohexa-1,4-dienyl)butanamide, Pattern B.

TGA analysis of the 300 mg lot, showed a 4.7% weight loss between 25-115° C., likely attributed to the loss of THF, followed by decomposition (FIG. 28). Moisture content was confirmed by Karl Fischer analysis which showed the materials to contain approximately 0.3 wt % water.

Figure 41:
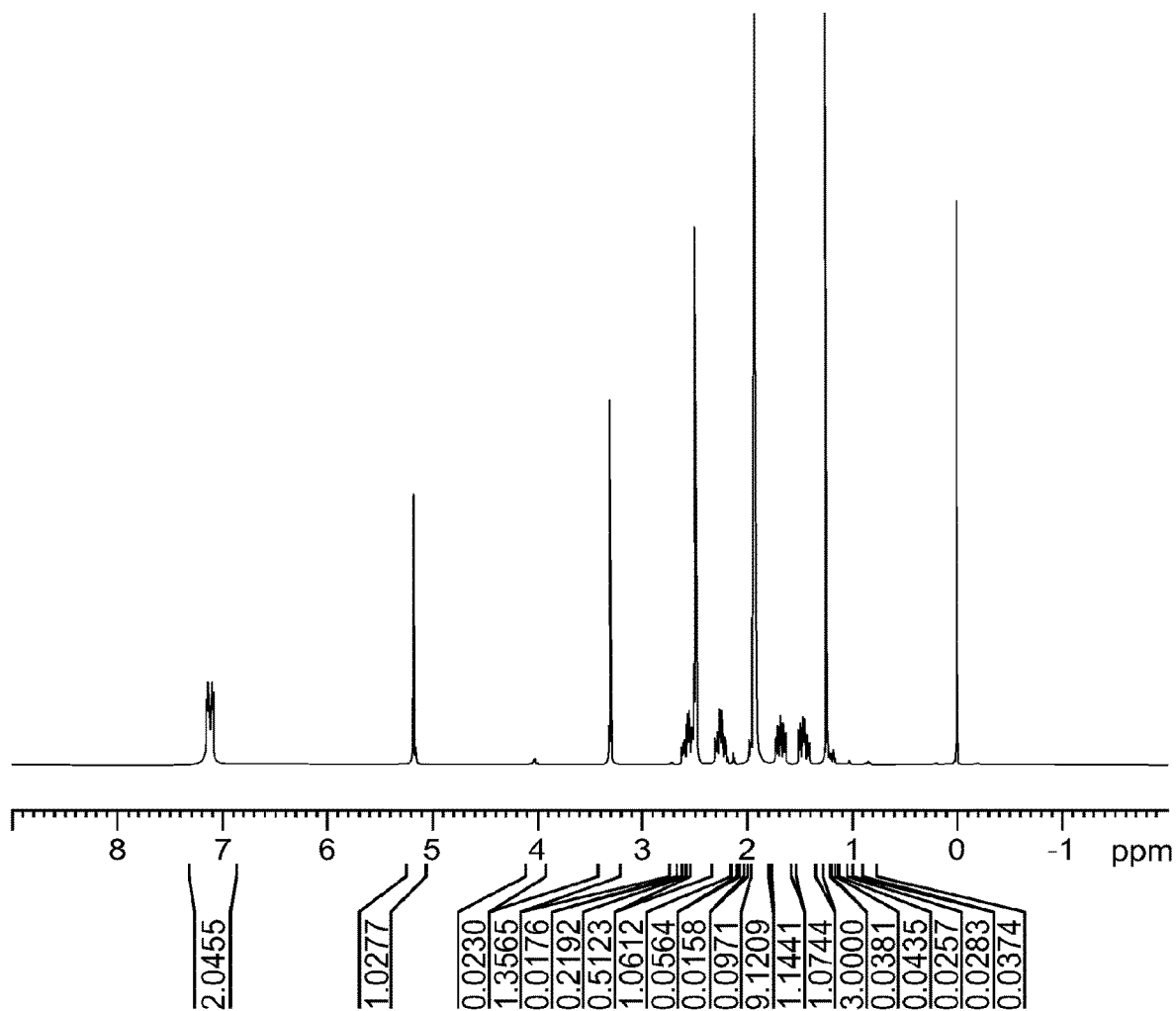
FIG. 41 shows a $^1$H NMR spectrum of (R)-2-hydroxy-2-methyl-4-(2,4,5-trimethyl-3,6-dioxocyclohexa-1,4-dienyl)butanamide, Pattern B.

Further analysis of Pattern B (300 mg lot) by $^1$H NMR showed the material to be consistent with structure of (R)-2-hydroxy-2-methyl-4-(2,4,5-trimethyl-3,6-dioxocyclohexa-1,4-dienyl)butanamide and contain 6.9 wt % residual THF. See FIG. 41.

Figure 29:
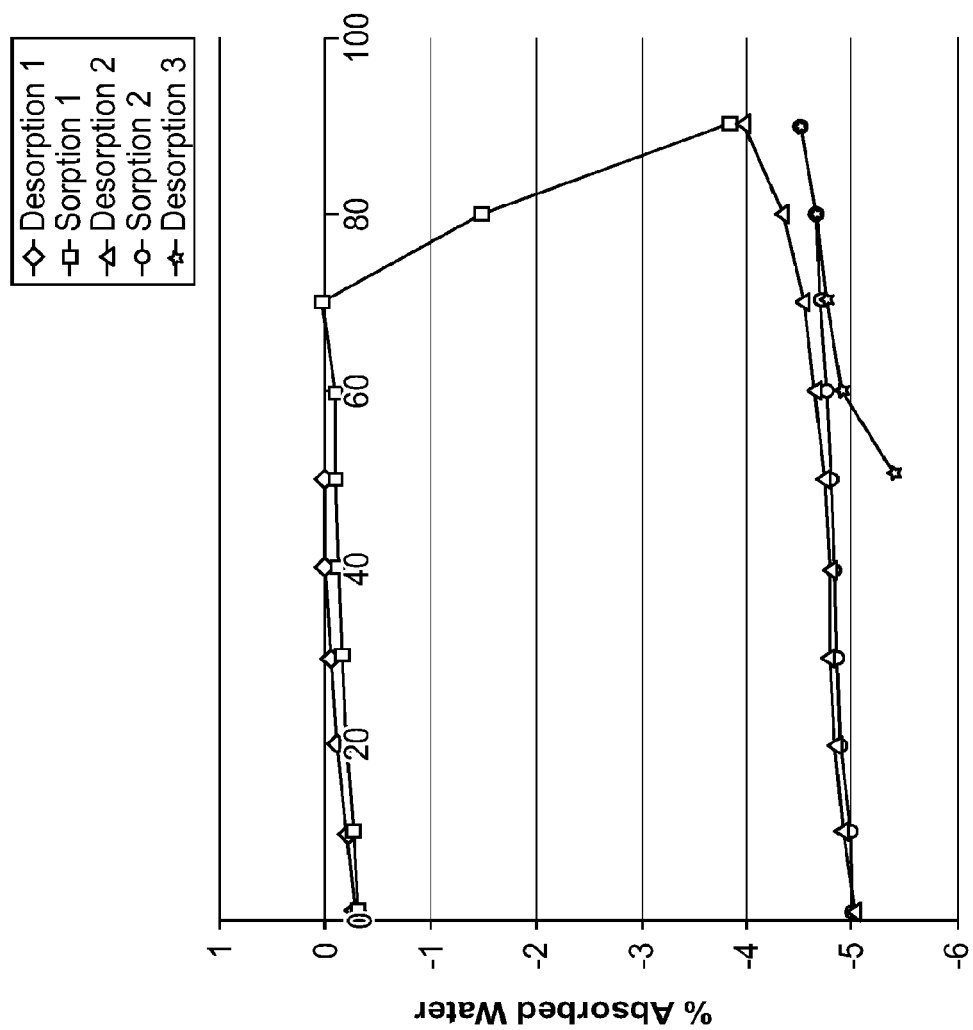
FIG. 29 shows a moisture sorption-desorption plot of (R)-2-hydroxy-2-methyl-4-(2,4,5-trimethyl-3,6-dioxocyclohexa-1,4-dienyl)butanamide Pattern B.

Moisture sorption analysis of Pattern B (300 mg lot) was performed by equilibrating the sample at 25° C. and 50% RH to simulate ambient lab conditions. Humidity then decreased to 0% RH, increased from 0 to 95% RH, reduced from 95 to 0% RH, increased from 0 to 95% RH and then decreased from 95 to 50% RH. Each point represents the estimated asymptotic weight for each humidity or weight. Pattern B was found to be non-hygroscopic, showing weight loss likely due to release of residual THF (FIG. 29). The major weight loss at the beginning was due to loss of solvent. XRPD analysis of sample following moisture sorption analysis was found to be consistent with Pattern A.

Pattern D (2-MeTHF Solvate, Form V)

Figure 30:
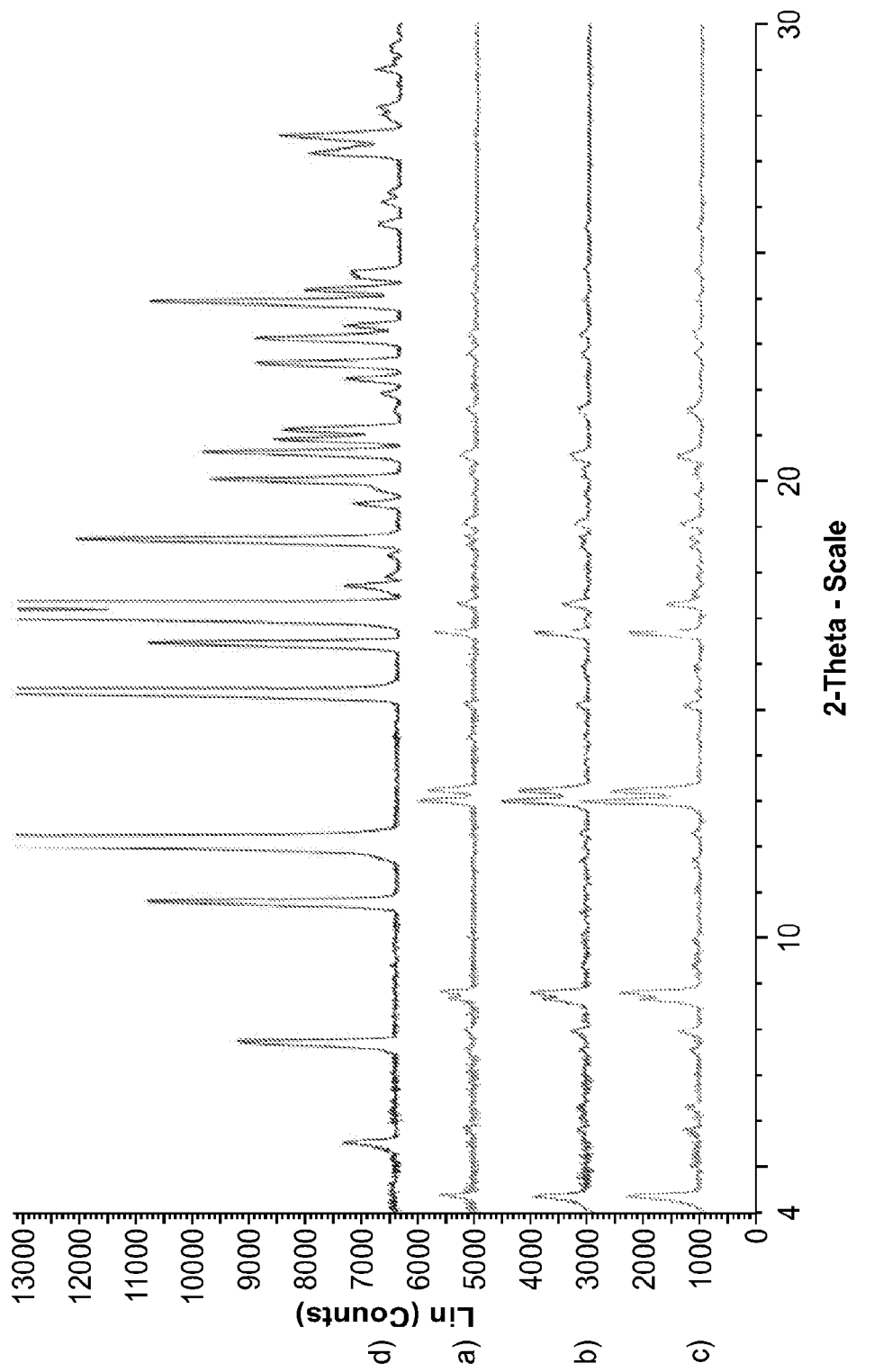
FIG. 30 shows a XRPD stack plot of (R)-2-hydroxy-2-methyl-4-(2,4,5-trimethyl-3,6-dioxocyclohexa-1,4-dienyl)butanamide Pattern D from evaporative crystallization in 2-MeTHF, a) from Example 4, b) Example 5 (fast cooling), c) Example 5 (slow cooling) and d) starting material Pattern A.

Pattern D (2-MeTHF Solvate, Form V) was observed during evaporative crystallizations in 2-MeTHF (Examples 4 and 5). XRPD analysis of the solids were found to afford a unique crystalline pattern, designated as Pattern D (FIG. 30).

Figure 31:
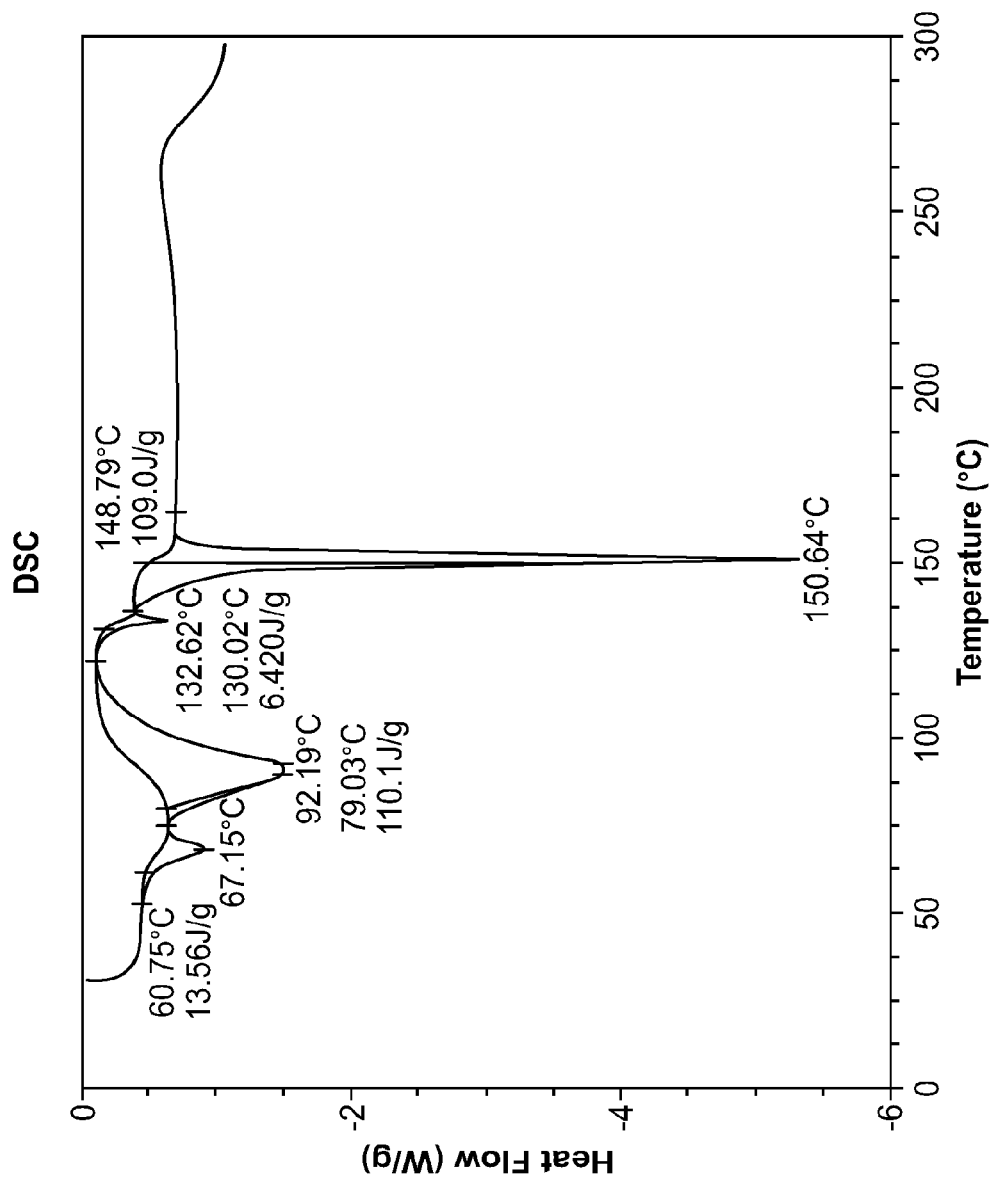
FIG. 31 shows a DSC thermogram of (R)-2-hydroxy-2-methyl-4-(2,4,5-trimethyl-3,6-dioxocyclohexa-1,4-dienyl)butanamide, Pattern D.

Thermal analysis of the Pattern D from Example 5 (slow cooling), by DSC showed four endothermic events at peaks of 67-2, 92.2, 132.6 and 150.6° C., followed by degradation after 220° C. (FIG. 31).

Figure 32:
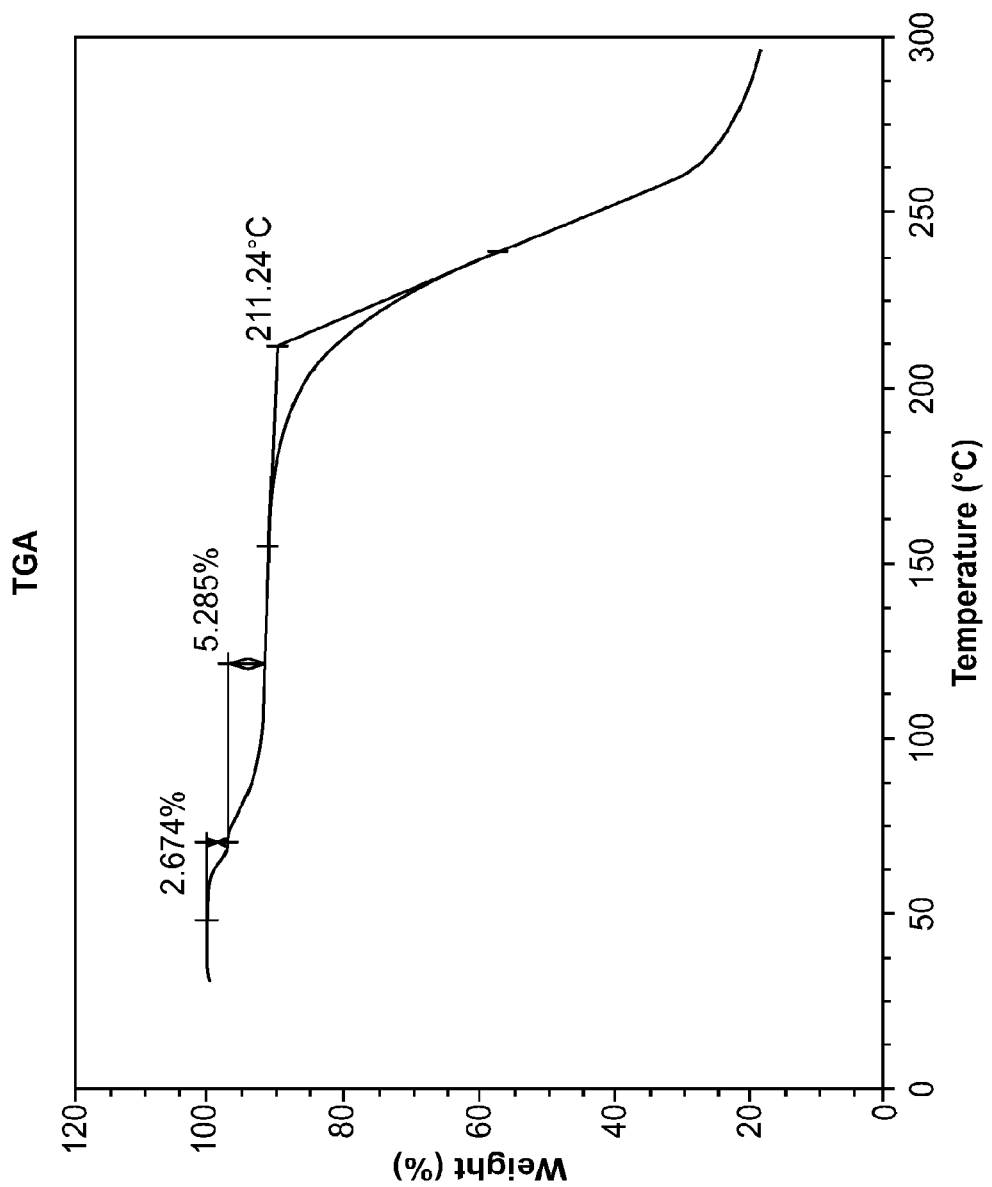
FIG. 32 shows a TGA thermogram of (R)-2-hydroxy-2-methyl-4-(2,4,5-trimethyl-3,6-dioxocyclohexa-1,4-dienyl)butanamide, Pattern D.

TGA analysis of Example 5 slow cooling lot, showed a 2.7% weight loss between 40-60° C. followed by a 5.3% weight loss from 60-115° C., likely attributed to the loss of 2-MeTHF, followed by decomposition (FIG. 32).

Figure 43:
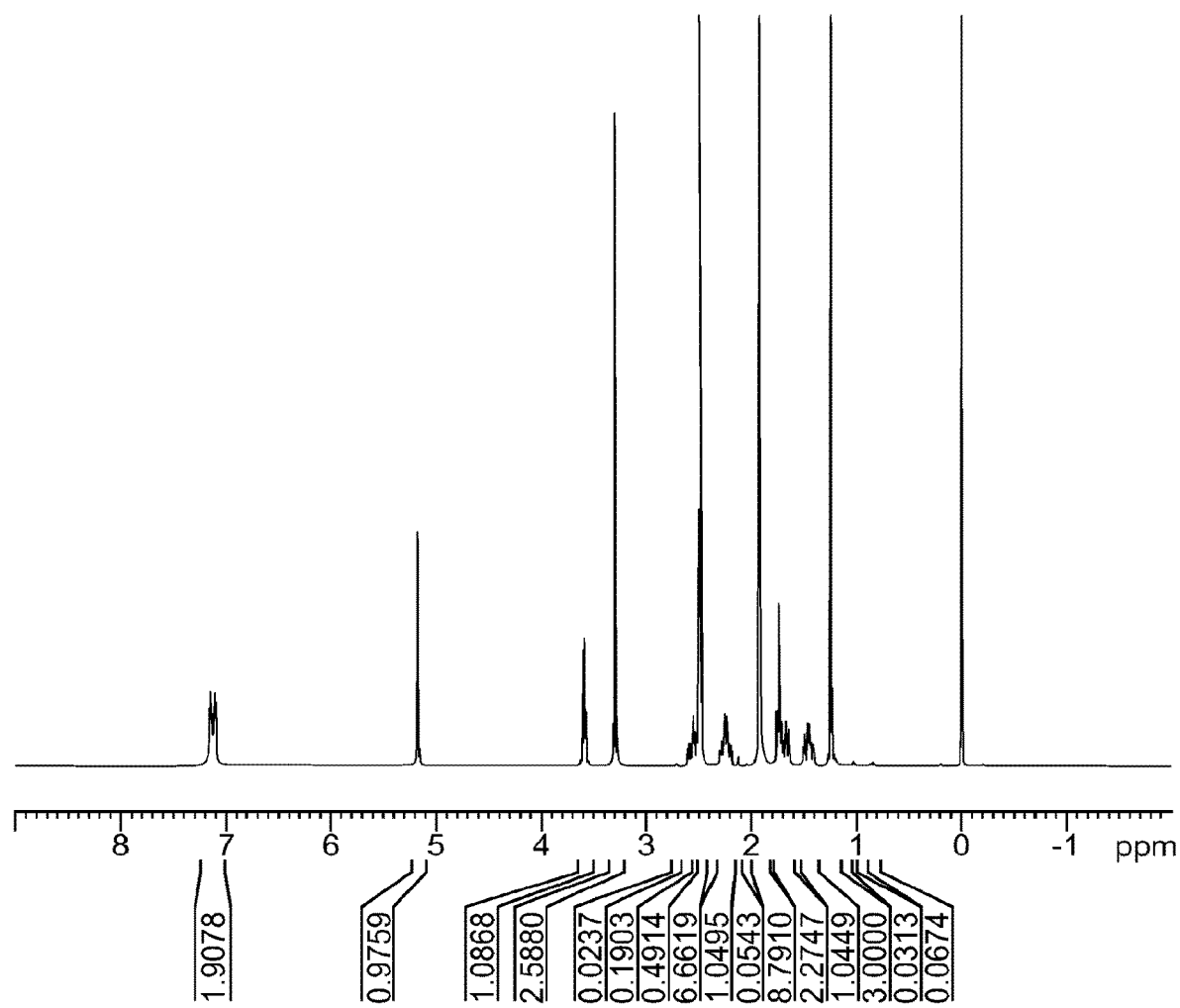
FIG. 43 shows a $^1$H NMR spectrum of (R)-2-hydroxy-2-methyl-4-(2,4,5-trimethyl-3,6-dioxocyclohexa-1,4-dienyl)butanamide, Pattern D.

Further analysis of Pattern D (Example 5 slow cooling lot) by $^1$H NMR showed the material to be consistent with structure of (R)-2-hydroxy-2-methyl-4-(2,4,5-trimethyl-3,6-dioxocyclohexa-1,4-dienyl)butanamide and contain 6.1 wt % residual 2-MeTHF. See FIG. 43.

Pattern F (2-MeTHF Solvate, Form VI)

Figure 33:
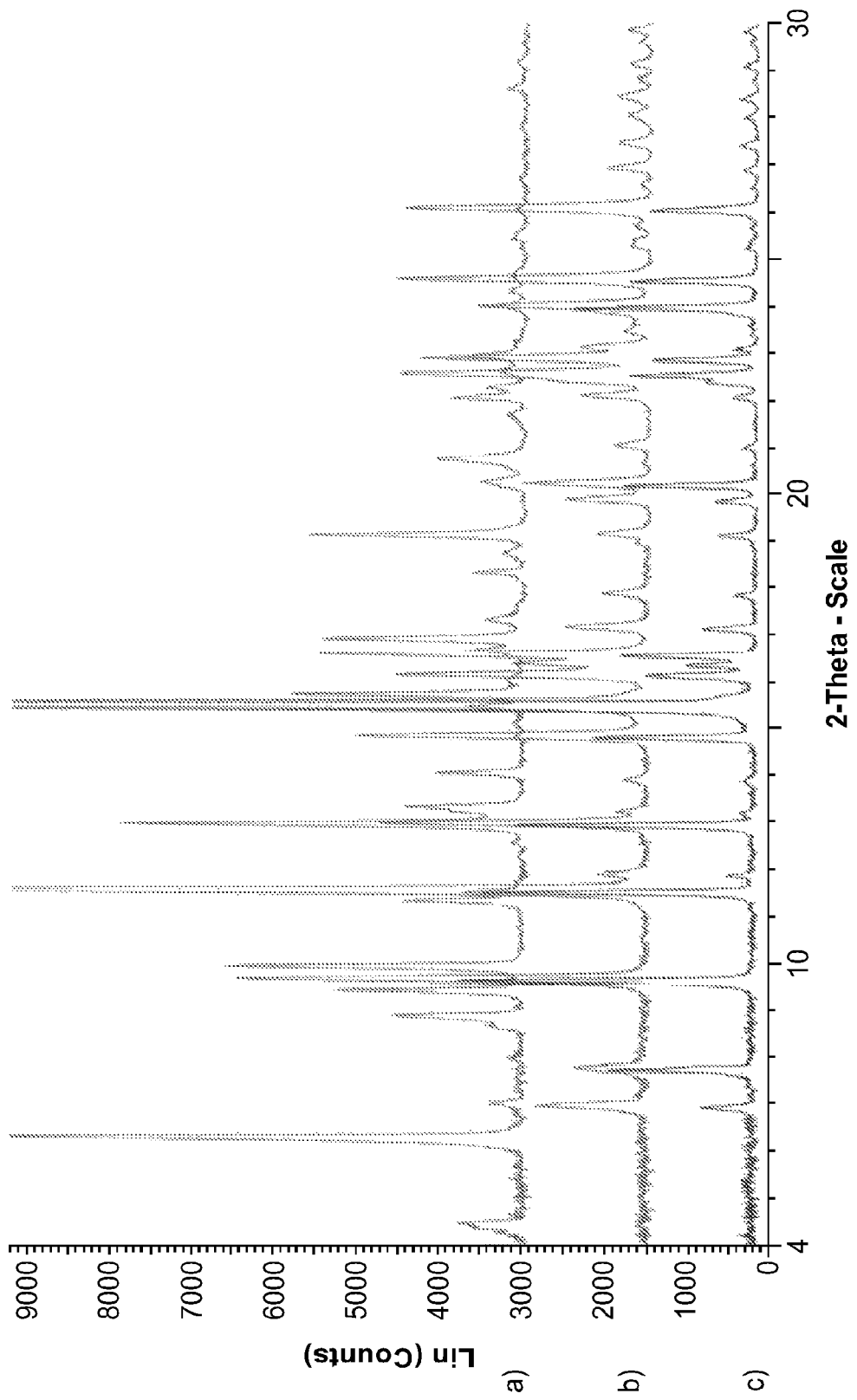
FIG. 33 shows a XRPD stack plot of (R)-2-hydroxy-2-methyl-4-(2,4,5-trimethyl-3,6-dioxocyclohexa-1,4-dienyl)butanamide Pattern F from single solvent crystallization in 2-MeTHF, a) from Example 6, b) following moisture sorption analysis (starting with Pattern F from Example 6) and c) Pattern E.
Figure 34:
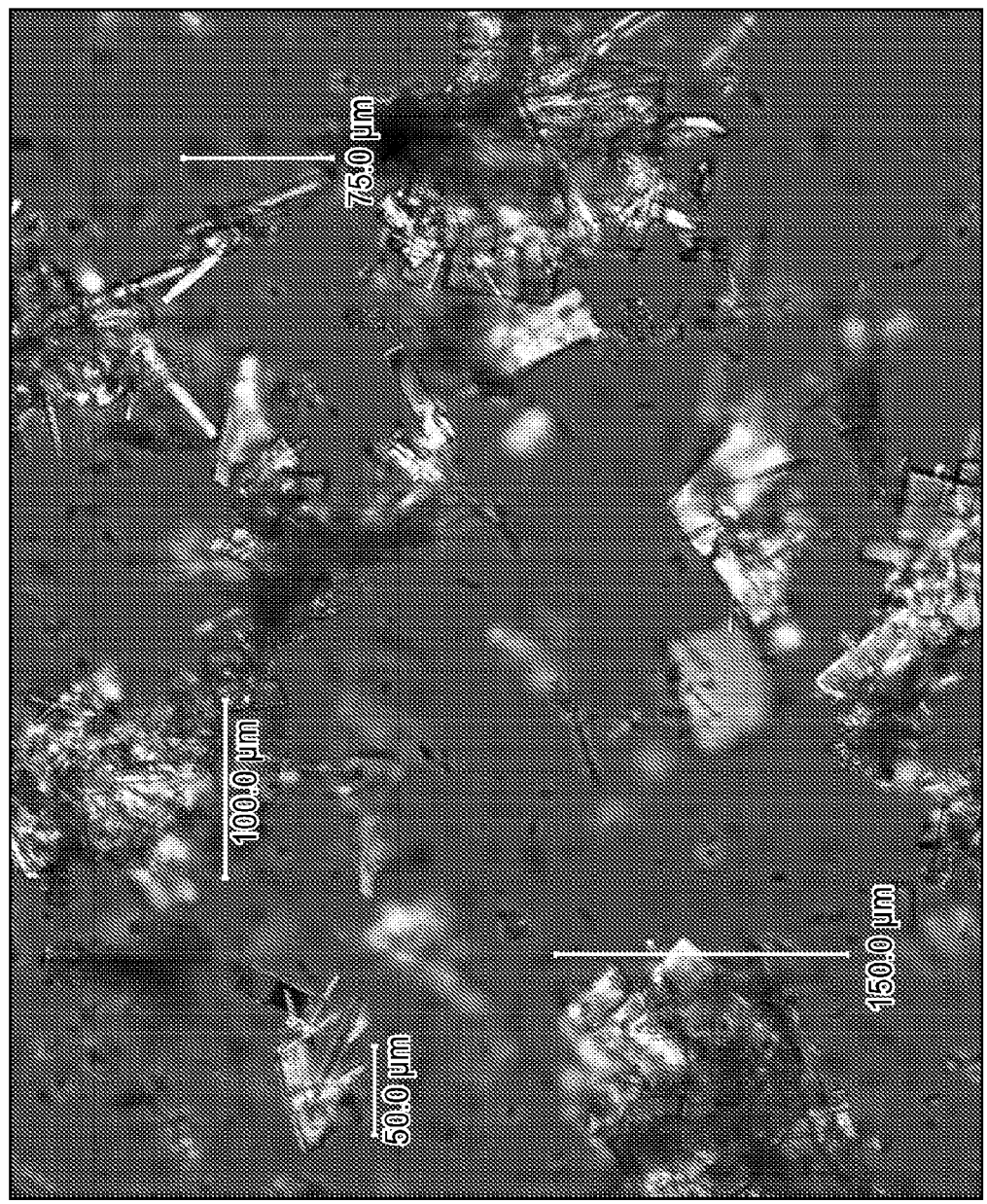
FIG. 34 shows an optical microscopy image of (R)-2-hydroxy-2-methyl-4-(2,4,5-trimethyl-3,6-dioxocyclohexa-1,4-dienyl)butanamide, Pattern F.

Pattern F (2-MeTHF Solvate, Form VI) was observed during single solvent crystallization scale-up experiments 2-MeTHF at the 300 mg scale (Example 6). XRPD analysis of the solids were found to afford a unique crystalline pattern, designated as Pattern F (FIG. 33). The crystallinity observed by XRPD was confirmed by the exhibition of birefringence observed by optical microscopy. The morphology of the crystals was determined to be plate shaped with some aggregation as shown in FIG. 34.

Figure 35:
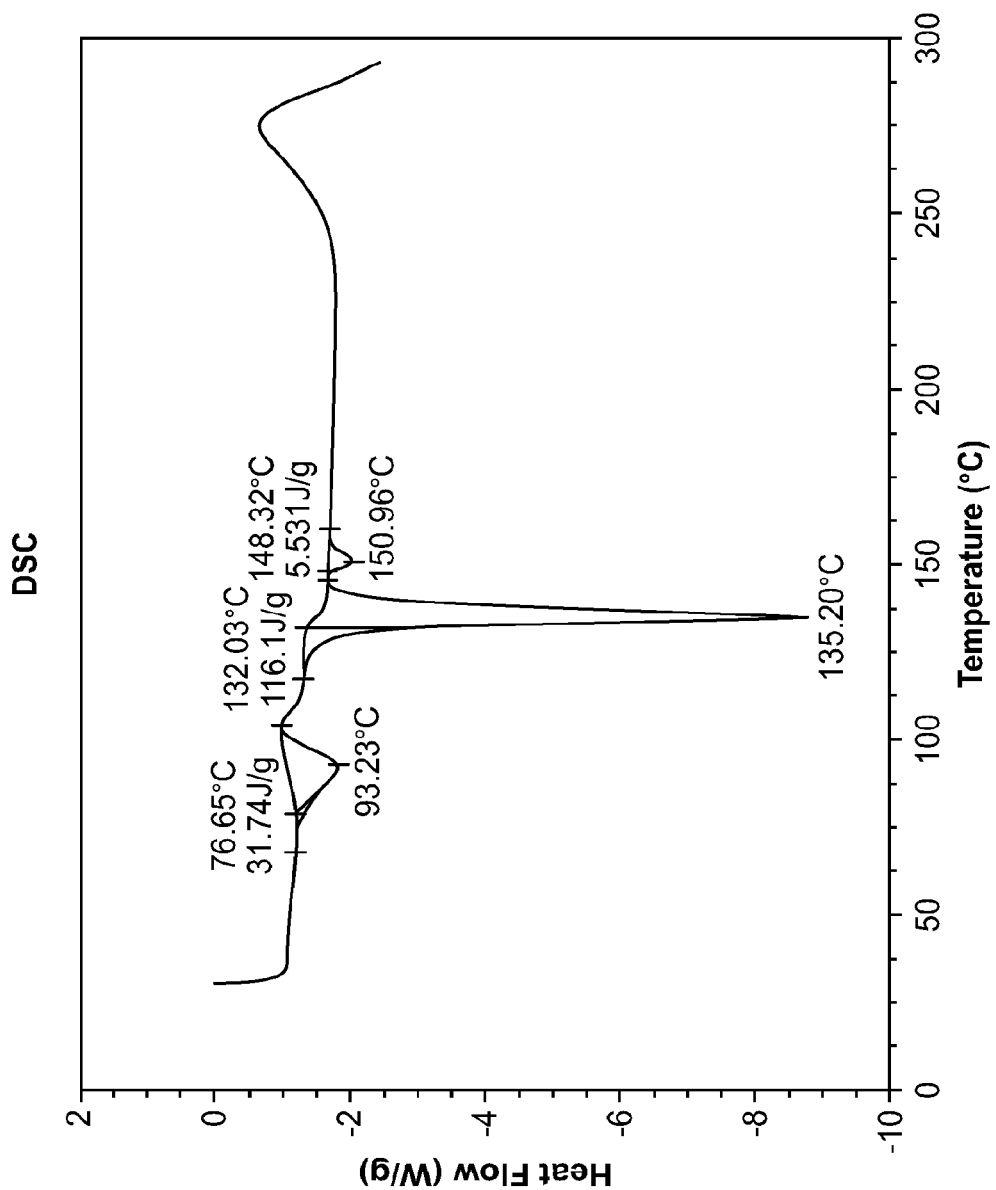
FIG. 35 shows a DSC thermogram of (R)-2-hydroxy-2-methyl-4-(2,4,5-trimethyl-3,6-dioxocyclohexa-1,4-dienyl)butanamide, Pattern F.

Thermal analysis of Pattern F (from Example 6) by DSC showed three endothermic events at peaks of 93.2, 135.2° C. and 151.0° C., followed by degradation after 220° C. (FIG. 35).

Figure 36:
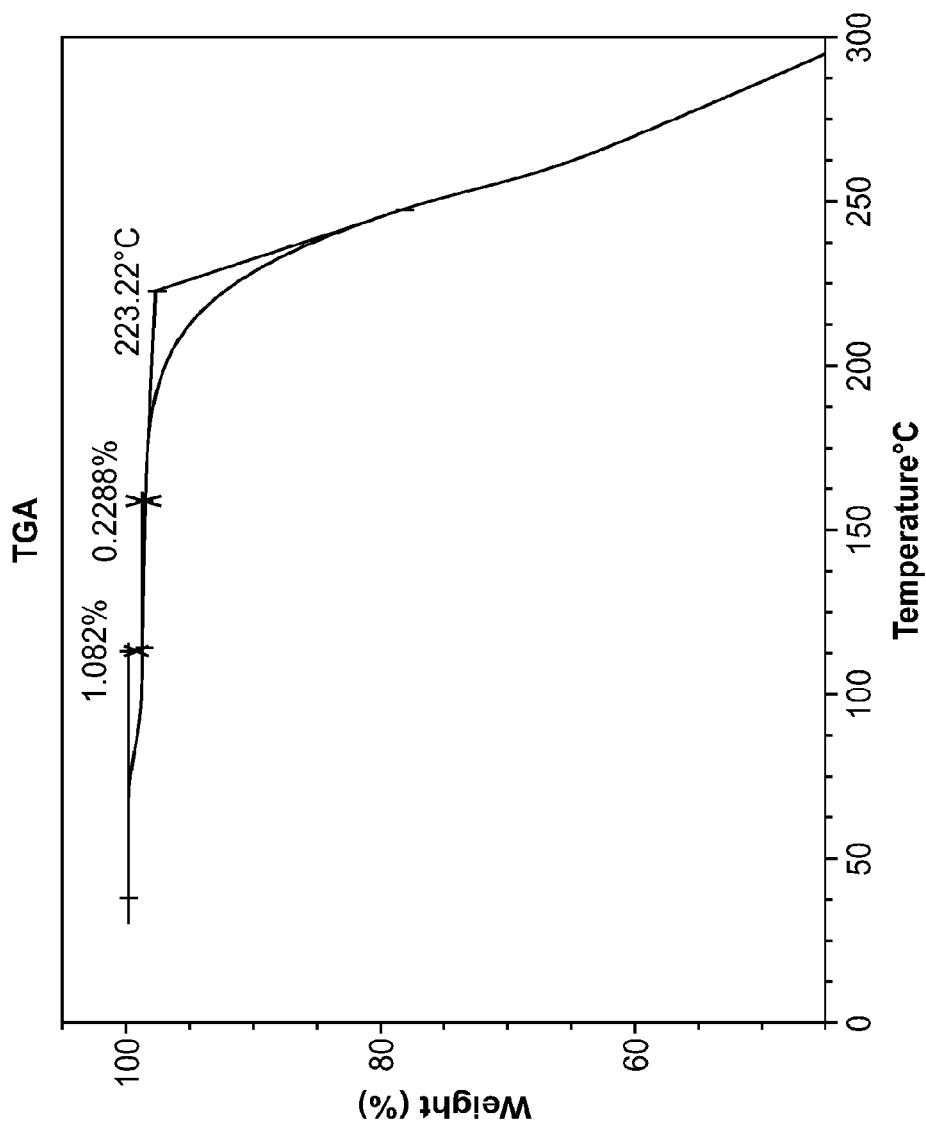
FIG. 36 shows a TGA thermogram of (R)-2-hydroxy-2-methyl-4-(2,4,5-trimethyl-3,6-dioxocyclohexa-1,4-dienyl)butanamide, Pattern F.

TGA analysis of Pattern F (from Example 6), showed a 1.1% weight loss between 30-110° C., followed by a 0.2% weight loss from 110-160° C., likely attributed to the loss of 2-MeTHF, followed by decomposition (FIG. 36). Moisture content was confirmed by Karl Fischer analysis which showed the materials to contain approximately 0.1 wt % water.

Figure 45:
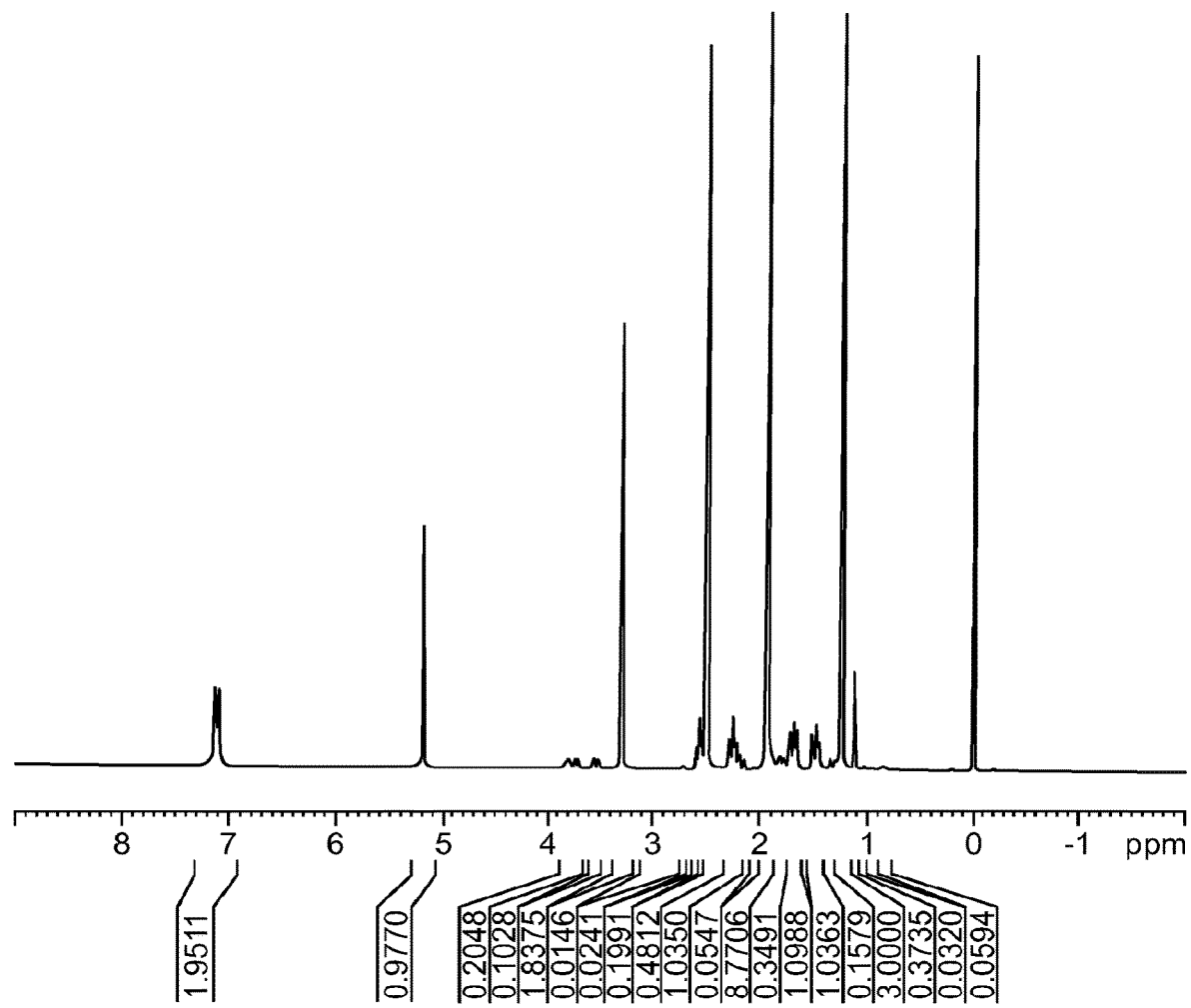
FIG. 45 shows a $^1$H NMR spectrum of (R)-2-hydroxy-2-methyl-4-(2,4,5-trimethyl-3,6-dioxocyclohexa-1,4-dienyl)butanamide, Pattern F.

Further analysis of Pattern F (from Example 6) by $^1$H NMR showed the material to be consistent with structure of (R)-2-hydroxy-2-methyl-4-(2,4,5-trimethyl-3,6-dioxocyclohexa-1,4-dienyl)butanamide and contain 3.9 wt % residual 2-MeTHF. See FIG. 45.

Figure 37:
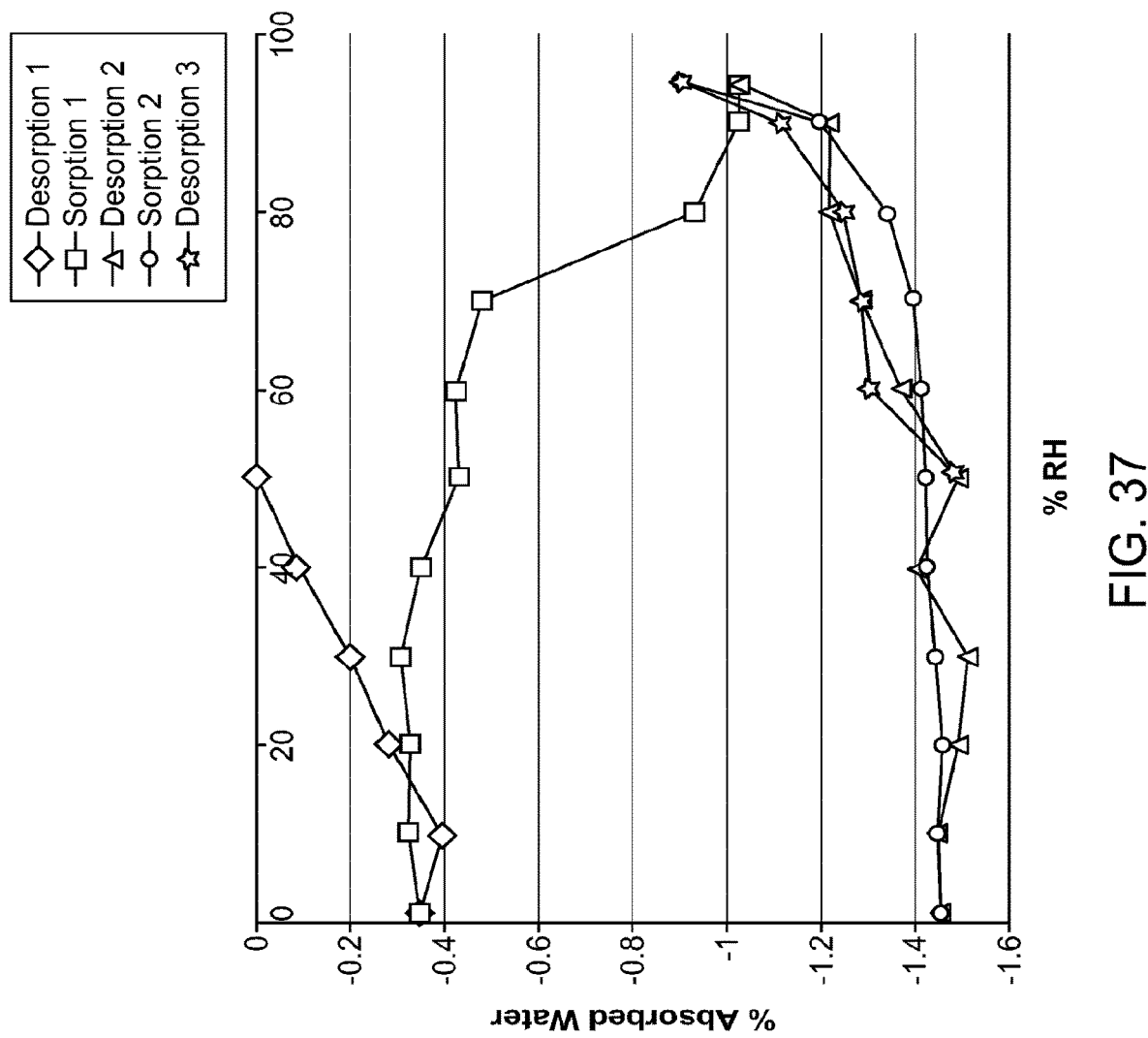
FIG. 37 shows a moisture sorption-desorption plot of (R)-2-hydroxy-2-methyl-4-(2,4,5-trimethyl-3,6-dioxocyclohexa-1,4-dienyl)butanamide, Pattern F.

Moisture sorption analysis of Pattern F (from Example 6) was performed by equilibrating the sample at 25° C. and 50% RH to simulate ambient lab conditions. Humidity was then decreased to 0% RH, increased from 0 to 95% RH, reduced from 95 to 0% RH, increased from 0 to 95% RH and then decreased from 95 to 50% RH. Each point represents the estimated asymptotic weight for each humidity or weight. Pattern F was found to be non-hygroscopic, showing weight loss likely due to release of residual 2-MeTHF (FIG. 37). The major weight loss at the beginning is due to loss of solvent. XRPD analysis of the sample following moisture sorption analysis was found to be consistent with Pattern E (FIG. 15).

Example 12. Screening Compounds of the Invention in Human Dermal Fibroblasts from Friedreich's Ataxia Patients An initial screen was performed to identify compounds effective for the amelioration of redox disorders. Test samples were tested for their ability to rescue FRDA fibroblasts stressed by addition of L-buthionine-(S,R)-sulfoximine (BSO), as described in Jauslin et al., Hum. Mol. Genet. 11(24):3055 (2002), Jauslin et al., FASEB J. 17:1972-4 (2003), and International Patent Application WO 2004/003565. Human dermal fibroblasts from Friedreich's Ataxia patients have been shown to be hypersensitive to inhibition of the de novo synthesis of glutathione (GSH) with L-buthionine-(S,R)-sulfoximine (BSO), a specific inhibitor of GSH synthetase (Jauslin et al., Hum. Mol. Genet. 11(24): 3055 (2002)).

MEM (a medium enriched in amino acids and vitamins, catalog no. 1-31F24-I) and Medium 199 (M199, catalog no. 1-21F22-I) with Earle's Balanced Salts, without phenol red, were purchased from Bioconcept. Fetal Calf Serum was obtained from PAA Laboratories. Basic fibroblast growth factor and epidermal growth factor were purchased from PeproTech. Penicillin-streptomycin-glutamine mix, L-buthionine (S,R)-sulfoximine, and insulin from bovine pancreas were purchased from Sigma. Calcein AM was purchased from Anaspec. Cell culture medium was made by combining 125 ml M199 EBS, 50 ml Fetal Calf Serum, 100 U/ml penicillin, 100 microgram/ml streptomycin, 2 mM glutamine, 10 microgram/ml insulin, 10 ng/ml EGF, and 10 ng/ml bFGF; MEM EBS was added to make the volume up to 500 ml. During the course of the experiments, this solution was stored at +4° C. The cells were obtained from the Coriell Cell Repositories (Camden, N.J.; repository number GM04078) and grown in 10 cm tissue culture plates. Every third day, they were split at a 1:3 ratio.

The test samples were supplied in 1.5 ml glass vials. The compounds were diluted with DMSO, ethanol or PBS to result in a 5 mM stock solution. Once dissolved, they were stored at −20° C.

Test Samples were Screened According to the Following Protocol:

A culture with FRDA fibroblasts was started from a 1 ml vial with approximately 500,000 cells stored in liquid nitrogen. Cells were propagated in 10 cm cell culture dishes by splitting every third day in a ratio of 1:3 until nine plates were available. Once confluent, fibroblasts were harvested. For 54 micro titer plates (96 well-MTP) a total of 14.3 million cells (passage eight) were re-suspended in 480 ml medium, corresponding to 100 microliters medium with 3,000 cells/well. The remaining cells were distributed in 10 cm cell culture plates (500,000 cells/plate) for propagation. The plates were incubated overnight at 37° C. in a atmosphere with 95% humidity and 5% CO2 to allow attachment of the cells to the culture plate.

10% DMSO (242.5 microliters) was added to a well of the microtiter plate. The test compounds were unfrozen, and 7.5 microliters of a 5 mM stock solution was dissolved in the well containing 242.5 microliters of 10% DMSO, resulting in a 150 micromolar master solution. Serial dilutions from the master solution were made. The period between the single dilution steps was kept as short as possible (generally less than 30 seconds). At least 4 hours after attachment into MTP, cells were then treated with the various compound dilutions.

Plates were kept overnight in the cell culture incubator. The next day, a solution containing BSO was added to the wells, in a manner similar to that described in Jauslin et al., Hum. Mol. Genet. 11(24):3055 (2002), Jauslin et al., FASEB J. 17:1972-4 (2003), and International Patent Application WO 2004/003565. Forty-eight hours later, three plates were examined under a phase-contrast microscope to verify that the cells in the negative control (wells E1-H1) were clearly dead. The medium from all plates was discarded, and the remaining liquid was removed by gently tapping the plate inversed onto a paper towel. The plates were washed twice with 100 uL of PBS containing Calcium and Magnesium.

100 microliters of PBS+Ca+Mg containing 1.2 micromolar Calcein AM were then added to each well. The plates were incubated for 30 minutes at 37 C. After that time fluorescence (excitation/emission wavelengths of 485 nm and 525 nm, respectively) was read on a Gemini fluorescence reader. Data was imported into Microsoft Excel (EXCEL is a registered trademark of Microsoft Corporation for a spreadsheet program) and ExcelFit was used to calculate the EC50 concentration for each compound.

The compounds were tested three times, i.e., the experiment was performed three times, the passage number of the cells increasing by one with every repetition.

The solvents (DMSO, ethanol, PBS) neither had a detrimental effect on the viability of non-BSO treated cells nor did they have a beneficial influence on BSO-treated fibroblasts even at the highest concentration tested (1%). None of the compounds showed auto-fluorescence. The viability of non-BSO treated fibroblasts was set as 100%, and the viability of the BSO- and compound-treated cells was calculated as relative to this value.

The following table summarizes the EC50 for (R)-2-hydroxy-2-methyl-4-(2,4,5-trimethyl-3,6-dioxocyclohexa-1,4-dienyl)butanamide.

| Disorder | EC50 |
|---|---|
| Friedrich's Ataxia | +++ |

+++ indicates less than 100 nM

Example 13. Screening (R)-2-hydroxy-2-methyl-4-(2,4,5-trimethyl-3,6-dioxocyclohexa-1,4-dienyl)butanamide in Fibroblasts from Patients Having Various Oxidative Stress Disorders (R)-2-hydroxy-2-methyl-4-(2,4,5-trimethyl-3,6-dioxocyclohexa-1,4-dienyl)butanamide was tested using a screen similar to the one described in Example 12, and substituting FRDA cells with cells from patients having other oxidative stress disorders.

The following table summarizes the EC50 for (R)-2-hydroxy-2-methyl-4-(2,4,5-trimethyl-3,6-dioxocyclohexa-1,4-dienyl)butanamide for various disorders.

| Disorder | Cell Line Tested | EC50 |
|---|---|---|
| Leigh Syndrome | Coriell Cell Repositories (Camden, NJ; repository number GMOI503A) | +++ |
| Leber's Hereditary Optic Neuropathy (LHON) | Coriell Cell Repositories (Camden, NJ; repository number GMO3858) | +++ |
| Parkinson's Disease | Coriell Cell Repositories (Camden, NJ; repository number AG20439) | |
| Huntington's Disease | Coriell Cell Repositories (Camden, NJ; repository number GM 04281) | +++ |
| Rett's Disorder | Coriell Cell Repositories (Camden, NJ; repository number GM-17567) | +++ |
| CoQlO Deficiency | From patients having a CoQ2 mutation | +++ |
| Amyotrophic Lateral Sclerosis C (ALS) | Coriell Cell Repositories (Camden, NJ; repository number ND29523) | +++ |

+++ indicates less than 100 nM; ++ indicates 100-500 nM

Example 14. Screening (R)-2-hydroxy-2-methyl-4-(2,4,5-trimethyl-3,6-dioxocyclohexa-1,4-dienyl)butanamide for Protection from Cisplatin-Induced Ototoxicity The conditionally immortalized auditory HEI-OC1 cells from long-term cultures of transgenic mice Immortomouse™ cochleas as described in Kalinec, G. et al., *Audiol. Nerootol.* 2003; 8, 177-189/. were maintained in high glucose Dulbecco's modified Eagle medium (DMEM) containing 10% FBS under permissive conditions, 33° C., 10% $CO_2$. Cells were pretreated overnight with (R)-2-hydroxy-2-methyl-4-(2,4,5-trimethyl-3,6-dioxocyclohexa-1,4-dienyl)butanamide, and apoptosis was detected by caspase3/7 activity after 24 hours of 50 uM cisplatin incubation. Cells incubated in diluent alone were the controls.

The following table summarizes the EC25 for (R)-2-hydroxy-2-methyl-4-(2,4,5-trimethyl-3,6-dioxocyclohexa-1,4-dienyl)butanamide

| Disorder | EC25 |
|---|---|
| Cisplatin-induced ototoxicity of auditory cells | +++ |

+++ indicates less than 100 micromolar

Example 15. Screening Polymorphic and Amorphous Compositions of the Invention in Fibroblasts from Patients Polymorphic and amorphous compositions of the invention are tested using screens similar to the ones described in Examples 12-14, substituting the polymorphic or amorphous form for (R)-2-hydroxy-2-methyl-4-(2,4,5-trimethyl-3,6-dioxocyclohexa-1,4-dienyl)butanamide. Polymorphic and amorphous compositions of the invention are also tested using screens similar to the ones described in Examples 12-14, and where appropriate substituting the FRDA cells or other cell lines with cells obtained from patients having an oxidative stress disorder described herein (e.g. MERRF, MELAS, KSS, Alzheimer's disease, a pervasive development disorder (such as autism), etc). The compositions are tested for their ability to rescue human dermal fibroblasts from these patients from oxidative stress or for their ability to protect cells from cisplatin-induced toxicity.

Example 16. Administration of Compositions of the Invention

A composition of the invention is presented in a capsule containing 300 mg of (R)-2-hydroxy-2-methyl-4-(2,4,5-trimethyl-3,6-dioxocyclohexa-1,4-dienyl)butanamide in a pharmaceutically acceptable carrier. A capsule is taken orally, once a day.

The disclosures of all publications, patents, patent applications and published patent applications referred to herein by an identifying citation are hereby incorporated herein by reference in their entirety Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A composition comprising a polymorph of an anhydrate, a hydrate, or a solvate of (R)-2-hydroxy-2-methyl-4-(2,4,5-trimethyl-3,6-dioxocyclohexa-1,4-dienyl)butanamide, wherein the composition comprises a polymorph Form I and at least one polymorph selected from the group consisting of Form II, Form III, Form IV, Form V, and Form VI;

wherein a powder X-ray diffraction pattern for polymorph Form I comprises characteristic peaks at least at the following angular positions, wherein the angular positions may vary by ±0.2: 12.06, 15.33, 17.03, and 17.26;

wherein a powder X-ray diffraction pattern for polymorph Form V comprises characteristic peaks at least at the following angular positions, wherein the angular positions may vary by ±0.2: 9.61, 11.49, 12.93, and 15.45;

wherein a powder X-ray diffraction pattern for polymorph Form III comprises characteristic peaks at least at the following angular positions, wherein the angular positions may vary by ±0.2: 9.16, 14.02, 15.23, and 21.10;

wherein a powder X-ray diffraction pattern for polymorph Form II comprises characteristic peaks at least at the following angular positions, wherein the angular positions may vary by ±0.2: 9.63, 10.85, 11.33, and 19.33;

wherein a powder X-ray diffraction pattern for polymorph Form IV comprises characteristic peaks at least at the following angular positions, wherein the angular positions may vary by ±0.2: 4.31, 8.76, 12.97, and 13.20; and wherein a powder X-ray diffraction pattern for polymorph Form VI comprises characteristic peaks at least at the following angular positions, wherein the angular positions may vary by ±0.2: 6.27, 9.91, 12.94, and 15.71.

2. The composition of claim 1, wherein the composition comprises polymorph Form I and Form II.

3. The composition of claim 1, wherein the composition comprises polymorph Form I and Form III.

4. The composition of claim 1, wherein the composition comprises polymorph Form I and Form IV.

5. The composition of claim 1, wherein the composition comprises polymorph Form I and Form V.

6. The composition of claim 1, wherein the composition comprises polymorph Form I and Form VI.

7. A pharmaceutical composition comprising the composition of claim 1 and a pharmaceutically acceptable carrier.

8. A method of treating or suppressing an oxidative stress disorder, modulating one or more energy biomarkers, normalizing one or more energy biomarkers, or enhancing one or more energy biomarkers, comprising
administering to an individual in need thereof a therapeutically effective amount or effective amount of the composition of claim 1.

9. The method of claim 8, wherein the method is a method of treating or suppressing an oxidative stress disorder selected from the group consisting of: a mitochondrial disorder; an inherited mitochondrial disease; Alpers Disease; Barth syndrome; a Beta-oxidation Defect; Carnitine-Acyl-Carnitine Deficiency; Carnitine Deficiency; a Creatine Deficiency Syndrome; Co-Enzyme Q10 Deficiency; Complex I Deficiency; Complex II Deficiency; Complex III Deficiency; Complex IV Deficiency; Complex V Deficiency; COX Deficiency; chronic progressive external ophthalmoplegia (CPEO); CPT I Deficiency; CPT II Deficiency; Friedreich's Ataxia (FA); Glutaric Aciduria Type II; Kearns-Sayre Syndrome (KSS); Lactic Acidosis; Long-Chain Acyl-CoA Dehydrogenase Deficiency (LCAD); LCHAD; Leigh Syndrome; Leigh-like Syndrome; Leber's Hereditary Optic Neuropathy (LHON); Lethal Infantile Cardiomyopathy (LIC); Luft Disease; Multiple Acyl-CoA Dehydrogenase Deficiency (MAD); Medium-Chain Acyl-CoA Dehydrogenase Deficiency (MCAD); Mitochondrial Myopathy, Encephalopathy, Lactacidosis, Stroke (MELAS); Myoclonic Epilepsy with Ragged Red Fibers (MERRF); Mitochondrial Recessive Ataxia Syndrome (MIRAS); Mitochondrial Cytopathy, Mitochondrial DNA Depletion; Mitochondrial Encephalopathy; Mitochondrial Myopathy; Myoneurogastrointestinal Disorder and Encephalopathy (MNGIE); Neuropathy, Ataxia, and Retinitis Pigmentosa (NARP); Pearson Syndrome; Pyruvate Carboxylase Deficiency; Pyruvate Dehydrogenase Deficiency; a Respiratory Chain Disorder; Short-Chain Acyl-CoA Dehydrogenase Deficiency (SCAD); SCHAD; Very Long-Chain Acyl-CoA Dehydrogenase Deficiency (VLCAD); a myopathy; cardiomyopathy; encephalomyopathy; a neurodegenerative disease; Parkinson's disease; Alzheimer's disease; amyotrophic lateral sclerosis (ALS); a motor neuron disease; a neurological disease; epilepsy; an age-associated disease; macular degeneration; diabetes; metabolic syndrome; cancer; brain cancer; a genetic disease; Huntington's Disease; a mood disorder; schizophrenia; bipolar disorder; a pervasive developmental disorder; autistic disorder; Asperger's syndrome; childhood disintegrative disorder (CDD); Rett's disorder; PDD-not otherwise specified (PDD-NOS); a cerebrovascular accident; stroke; a vision impairment; optic neuropathy; dominant inherited juvenile optic atrophy; optic neuropathy caused by a toxic agent; glaucoma; Stargardt's macular dystrophy; diabetic retinopathy; diabetic maculopathy; retinopathy of prematurity; ischemic reperfusion-related retinal injury; oxygen poisoning; a haemoglobinopathy; thalassemia; sickle cell anemia; seizures; ischemia; renal tubular acidosis; attention deficit/hyperactivity disorder (ADHD); a neurodegenerative disorder resulting in hearing or balance impairment; Dominant Optic Atrophy (DOA); Maternally inherited diabetes and deafness (MIDD); chronic fatigue; contrast-induced kidney damage; contrast-induced retinopathy damage; Abetalipoproteinemia; retinitis pigmentosum; Wolfram's disease; Tourette syndrome; cobalamin c defect; methylmalonic aciduria; glioblastoma; Down's syndrome; acute tubular necrosis; a muscular dystrophy; a leukodystrophy; Progressive Supranuclear Palsy; spinal muscular atrophy; hearing loss; noise induced hearing loss; traumatic brain injury; Juvenile Huntington's Disease; Multiple Sclerosis; NGLY1; Multiple System Atrophy; Adrenoleukodystrophy; and Adrenomyeloneuropathy.

10. The method of claim 9, wherein the oxidative stress disorder is cancer.

11. The method of claim 9, wherein the oxidative stress disorder is an age-associated disease.

12. The method of claim 9, wherein the oxidative stress disorder is a muscular dystrophy.

13. The method of claim 9, wherein the oxidative stress disorder is amyotrophic lateral sclerosis (ALS).

* * * * *